(12) United States Patent
van Ooyen et al.

(10) Patent No.: US 9,721,418 B2
(45) Date of Patent: *Aug. 1, 2017

(54) VENDING MACHINE CONTAINER LABELING AND DISPENSING METHOD

(71) Applicant: MEDAVAIL, INC., San Francisco, CA (US)

(72) Inventors: Wes van Ooyen, Burlington (CA); Derek Bessette, Milton (CA); Duane Lindner, Bradford (CA)

(73) Assignee: MEDAVAIL, INC., San Francisco, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 14/274,943

(22) Filed: May 12, 2014

(65) Prior Publication Data

US 2015/0019008 A1    Jan. 15, 2015

Related U.S. Application Data

(63) Continuation of application No. 13/173,869, filed on Jun. 30, 2011, now Pat. No. 8,738,177.

(60) Provisional application No. 61/360,509, filed on Jul. 1, 2010.

(51) Int. Cl.
| | |
|---|---|
| G07F 11/00 | (2006.01) |
| G06F 19/00 | (2011.01) |
| G07F 17/00 | (2006.01) |
| G07F 11/44 | (2006.01) |
| G07F 11/58 | (2006.01) |
| B65C 9/46 | (2006.01) |
| B65C 9/00 | (2006.01) |

(52) U.S. Cl.
CPC .......... *G07F 11/00* (2013.01); *G06F 19/3462* (2013.01); *G07F 11/44* (2013.01); *G07F 11/58* (2013.01); *G07F 17/0092* (2013.01); *B65C 9/46* (2013.01); *B65C 2009/0003* (2013.01)

(58) Field of Classification Search
CPC ..................... G06F 19/3462; G07F 17/0092
USPC ................... 700/235, 232, 236, 242–244
See application file for complete search history.

(56) References Cited

U.S. PATENT DOCUMENTS

| | | | | |
|---|---|---|---|---|
| 5,674,347 A | * | 10/1997 | Edwards | ............... B65B 7/2807 156/351 |
| 8,215,540 B2 | * | 7/2012 | Szesko | ................ G06F 19/3462 235/375 |
| 8,738,177 B2 | * | 5/2014 | van Ooyen | ......... G06F 19/3462 700/235 |
| 9,224,120 B2 | * | 12/2015 | Grabiner | ............... G06F 19/327 |

(Continued)

*Primary Examiner* — Michael K Collins
(74) *Attorney, Agent, or Firm* — Desandro Law Group PLLC; Bradley K. DeSandro

(57) ABSTRACT

A vending machine, in communication with a remote station, delivers a labeled container to a user from storage holding containers of different sizes and shapes and containing different products such as medicaments. A control system is operable to select a specific unlabeled container from among the other containers in storage, and to move the selected unlabeled container to a labeling module where a label is applied after the position of the label and/or the selected unlabeled container are/is adjusted so as to result in the label being applied at a desired position and angular orientation with respect to the selected unlabeled container. The control system is further operable to move the labeled container to a delivery zone accessible to the user.

15 Claims, 62 Drawing Sheets

(56) References Cited

U.S. PATENT DOCUMENTS

| | | | |
|---|---|---|---|
| 2006/0037706 A1* | 2/2006 | Putzer | B65C 9/06 |
| | | | 156/360 |
| 2006/0283145 A1* | 12/2006 | Weisgerber | B07C 5/3404 |
| | | | 53/167 |
| 2009/0050267 A1* | 2/2009 | Conlon | B65C 1/045 |
| | | | 156/312 |
| 2009/0173779 A1* | 7/2009 | Szesko | G06F 19/3462 |
| | | | 235/375 |
| 2010/0051187 A1* | 3/2010 | Willick | G07F 11/44 |
| | | | 156/238 |
| 2010/0071830 A1* | 3/2010 | Putzer | B65C 9/40 |
| | | | 156/64 |
| 2010/0089997 A1* | 4/2010 | Carson | G07F 9/026 |
| | | | 235/375 |
| 2015/0019008 A1* | 1/2015 | van Ooyen | G06F 19/3462 |
| | | | 700/235 |

* cited by examiner (Rx Label)

ABC Medical Clinic
123 Main Street, Smalltown, Ontario. L0L 1X0

DD#: 1248A     1-800-321-1111
Rx#: 9048591     Refills: 0
Smith, John     656-333
Take one tablet every day by mouth for pain.
Dr. I.M. Canadian     50 TAB     30-May-2006
TYLENOL-3 325mg TAB (Receipt)

--RECEIPT--

Smith, John     656-333

TYLENOL-3 325mg TAB     $ 9.80

Etc
Etc

*Fig. 5*

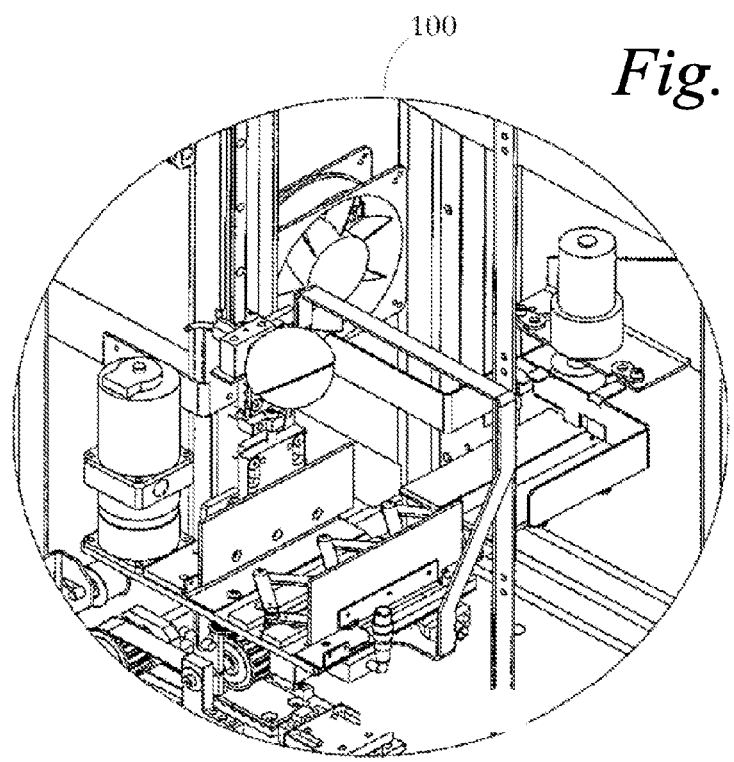
*Fig. 11B*
FIG. 3B
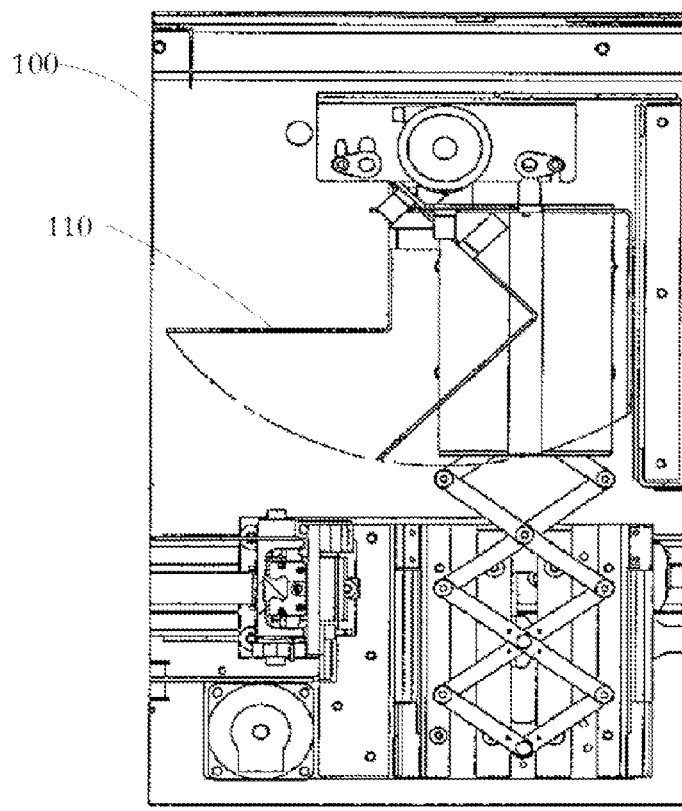
*Fig. 11C*

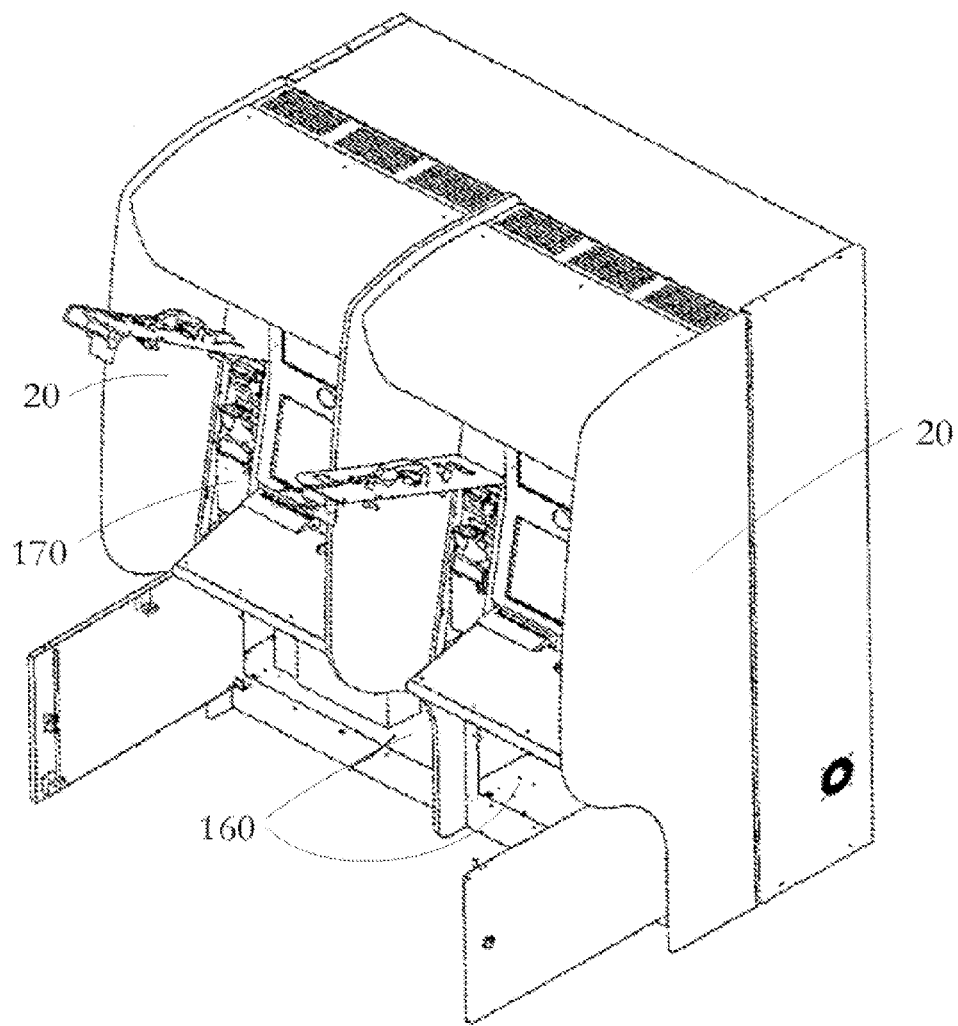
Fig. 13B1

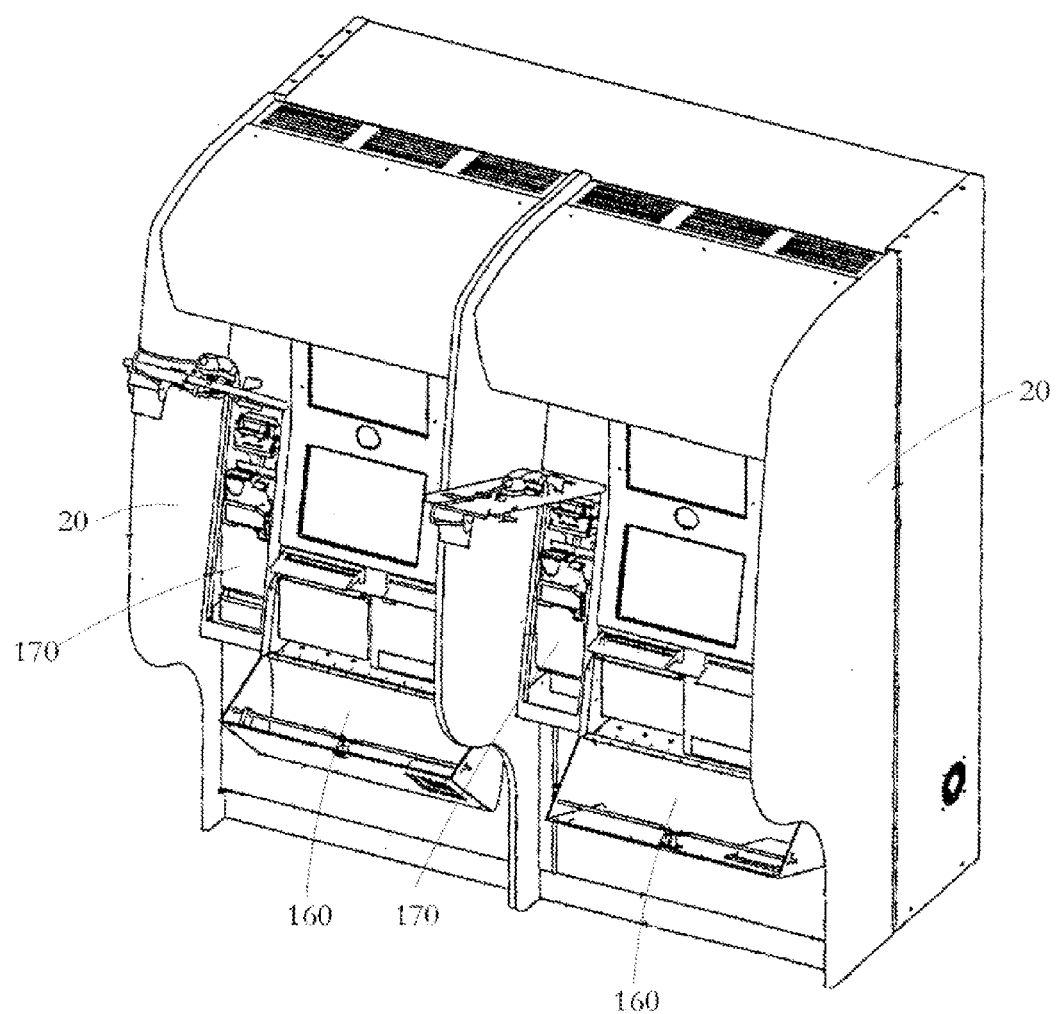
Fig. 13B2

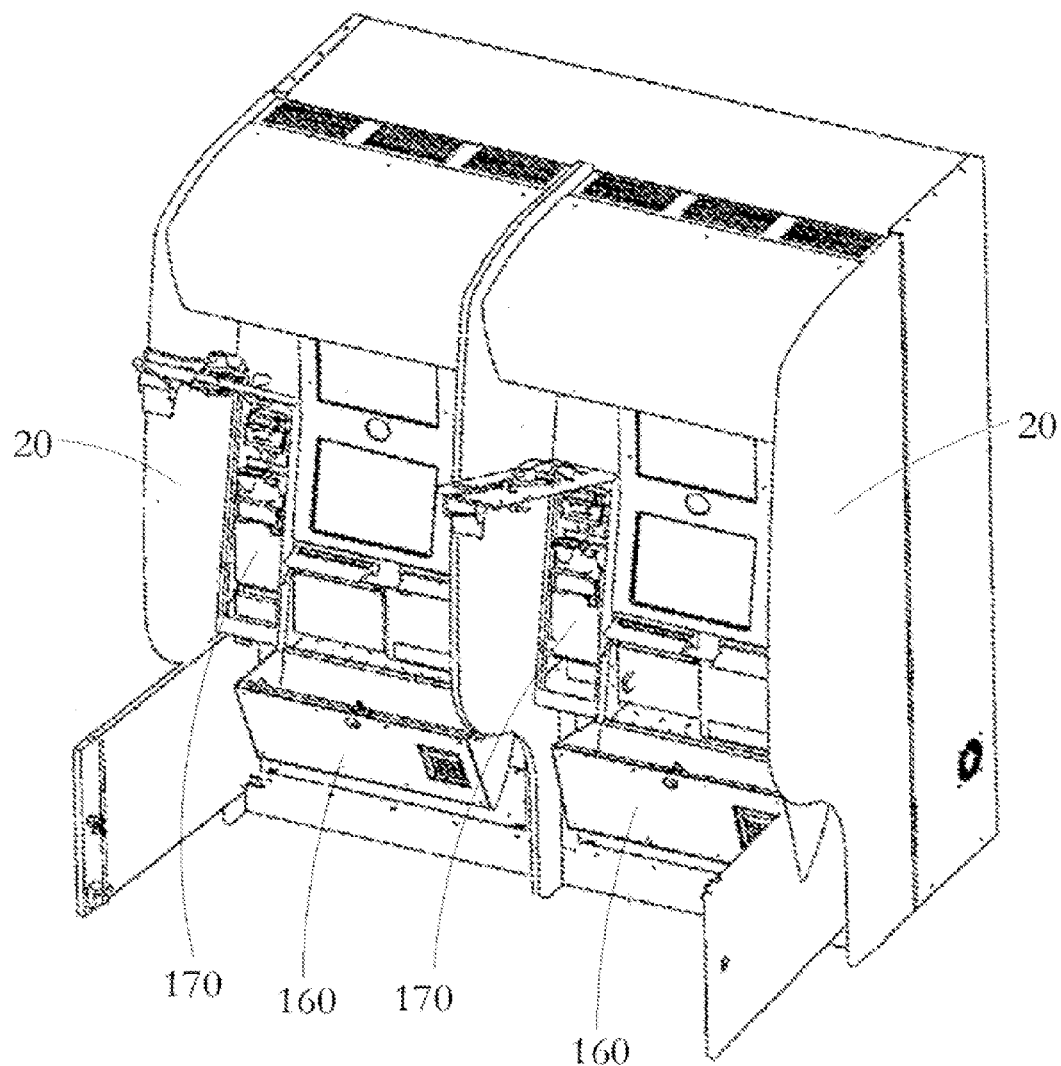
Fig. 13B3

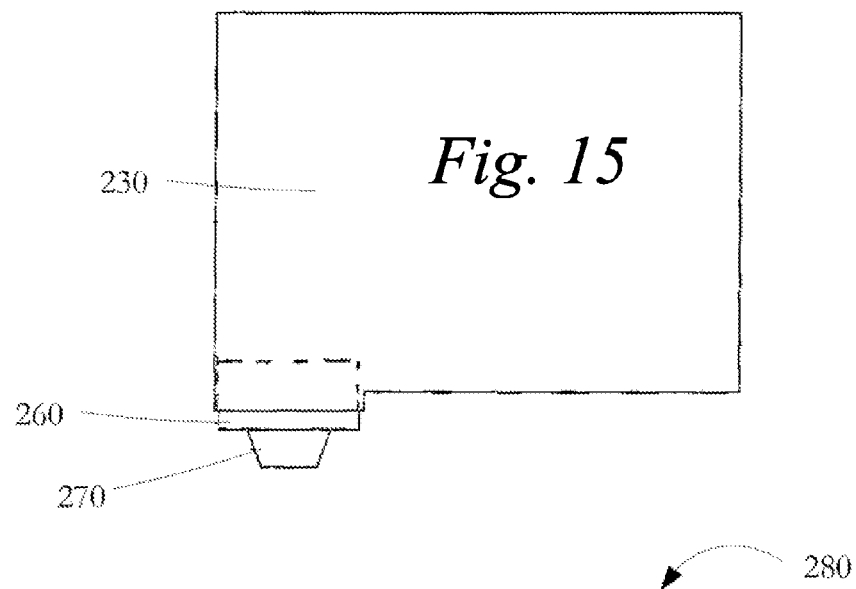
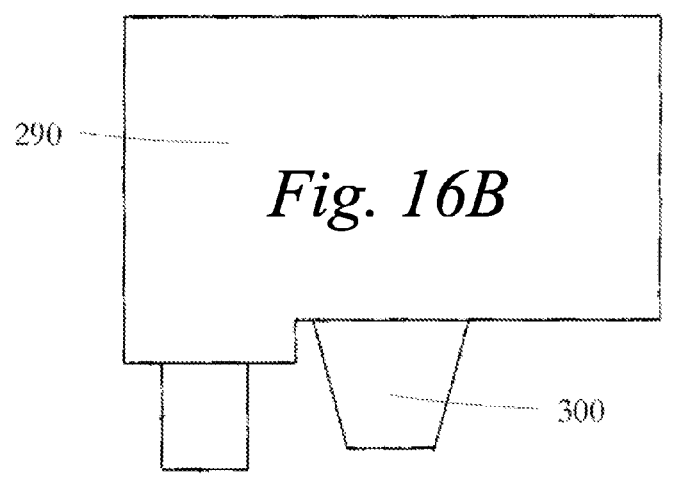
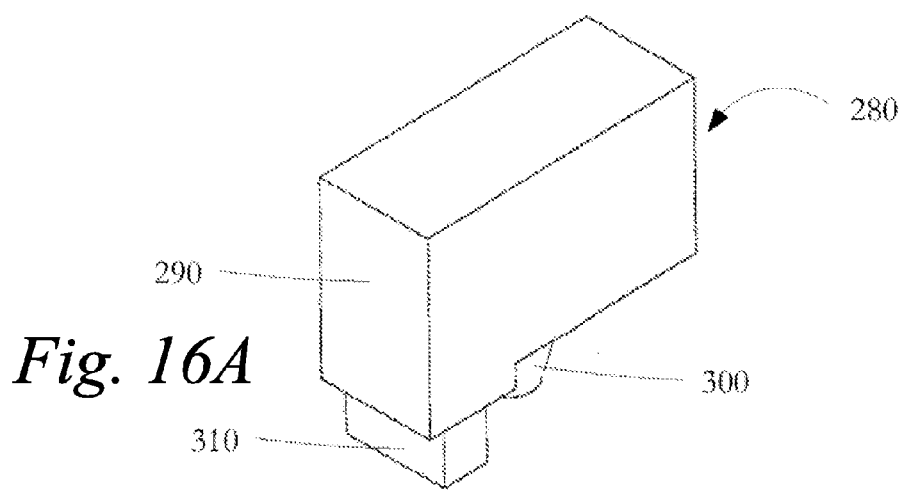

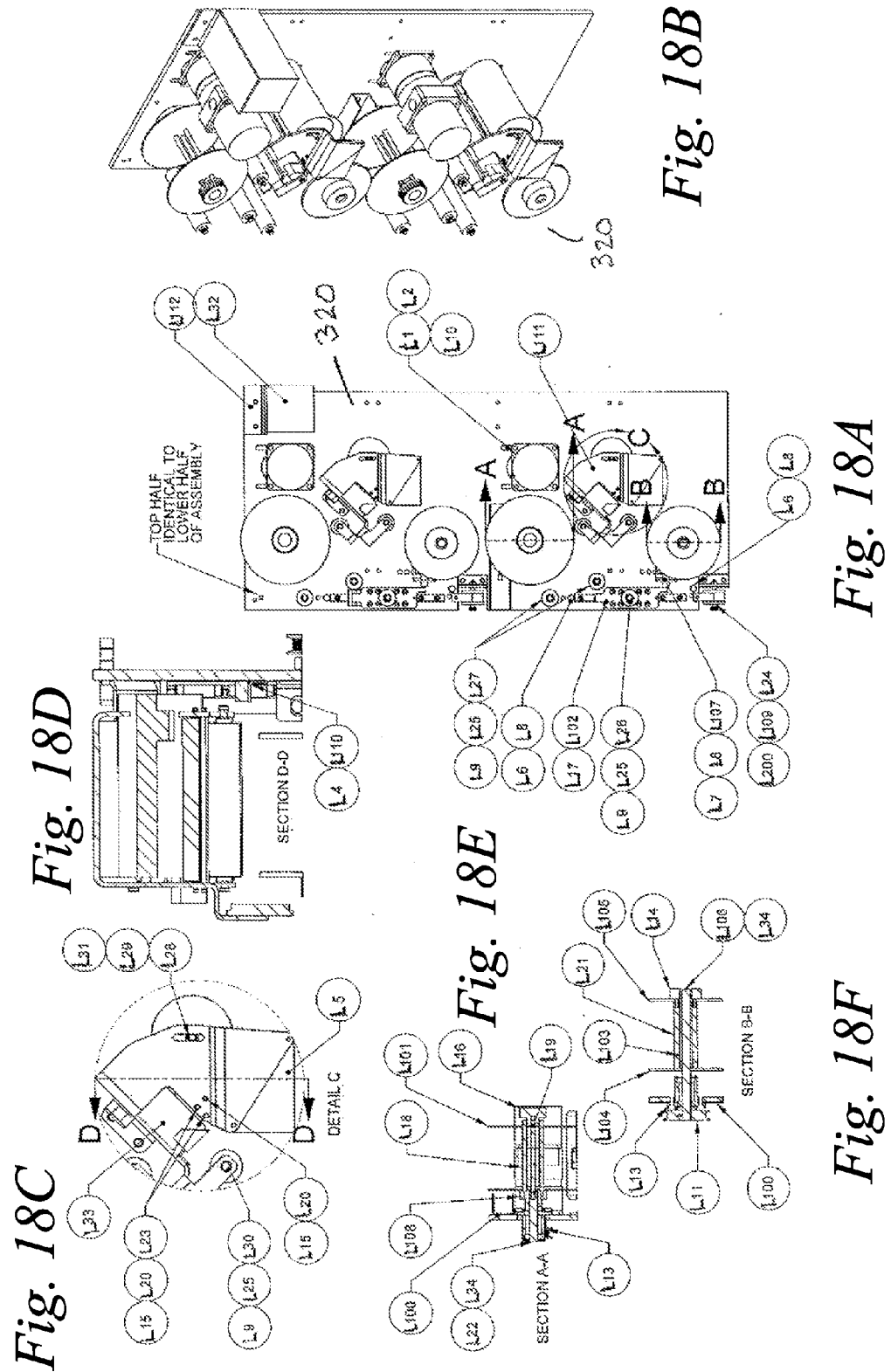

*Fig. 22A*
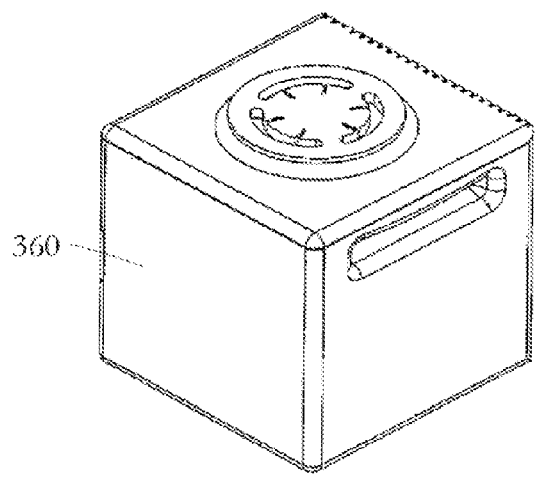
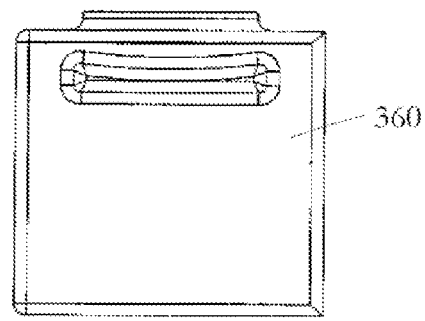
*Fig. 22B*
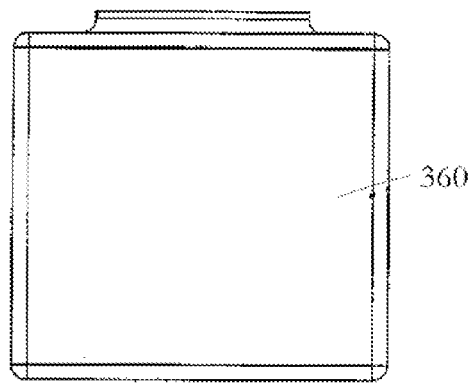 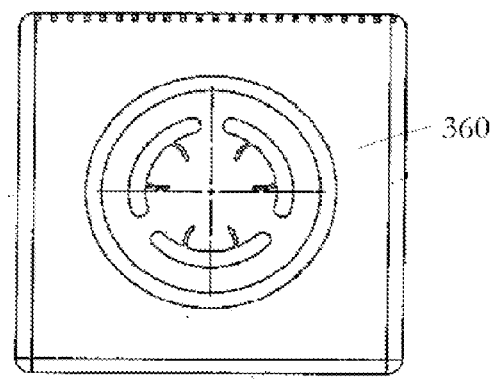
*Fig. 22C*          *Fig. 22D*

Fig. 26
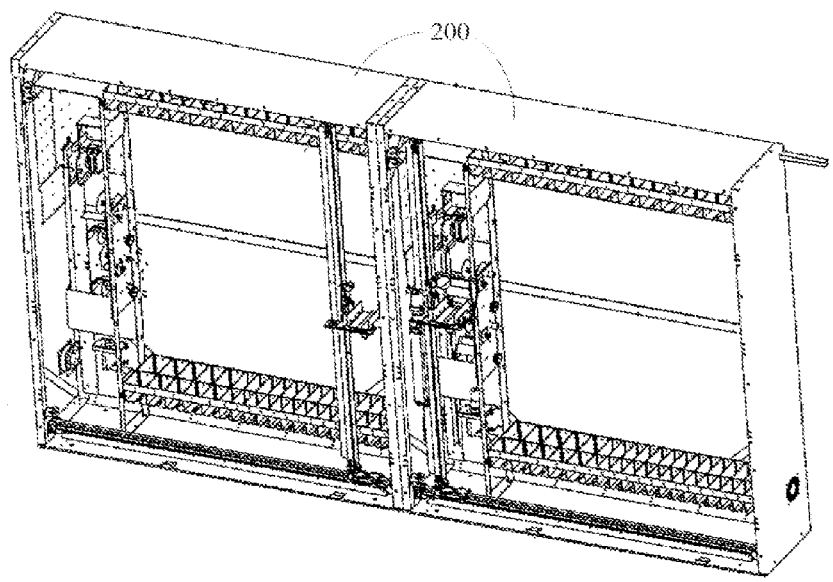
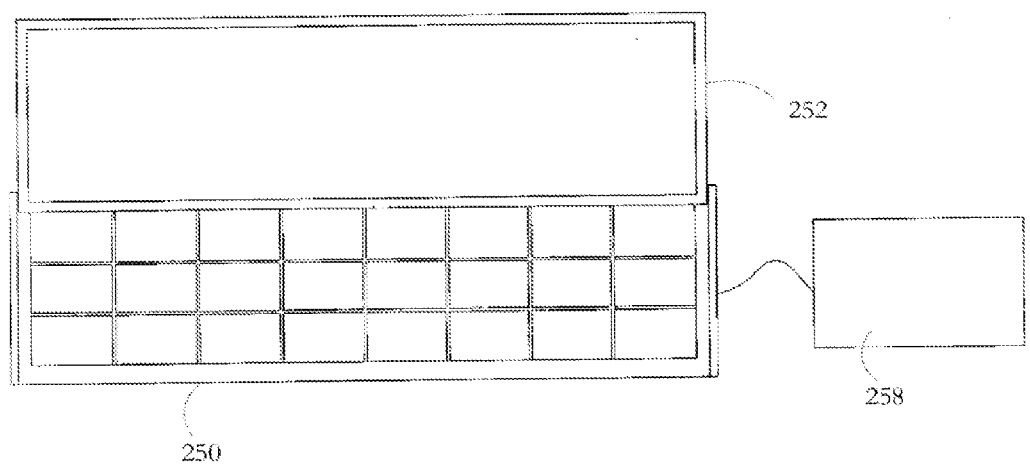
Fig. 27A

*Fig. 32A*
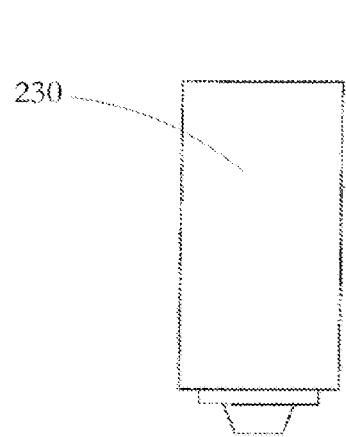
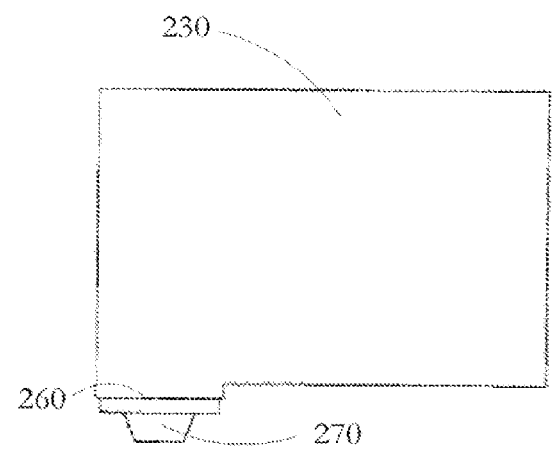
*Fig. 32B*

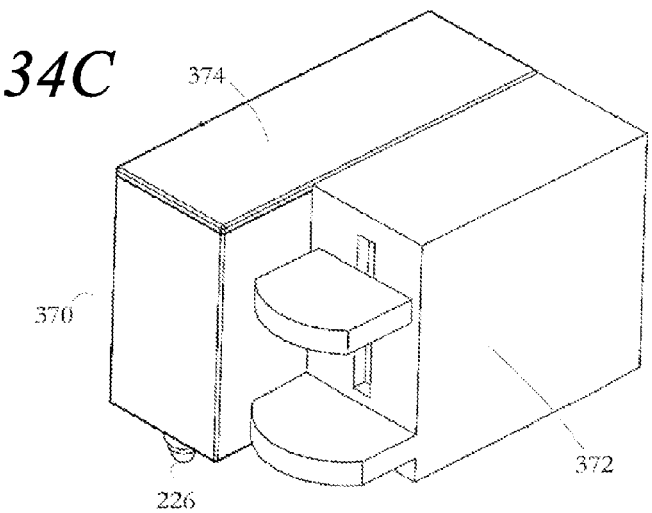
Fig. 34C
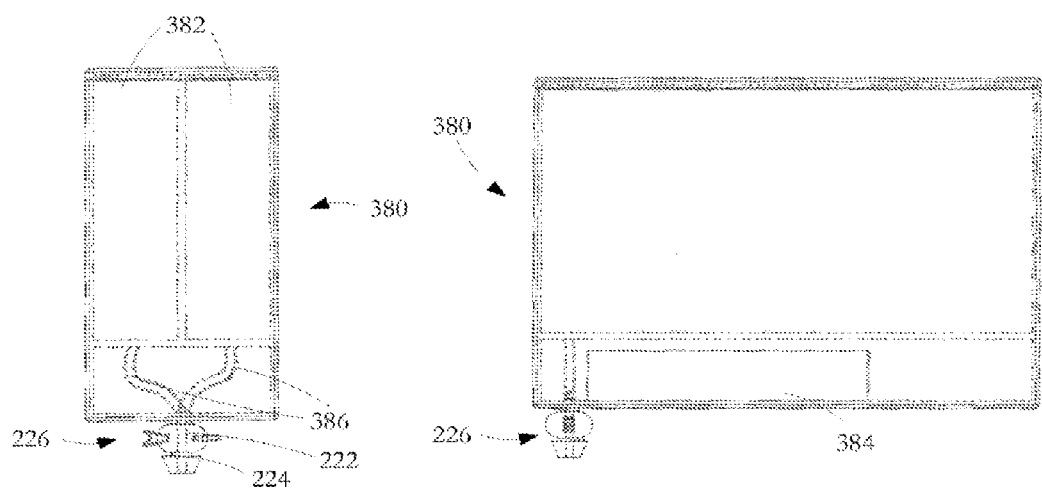
Fig. 35A
Fig. 35B

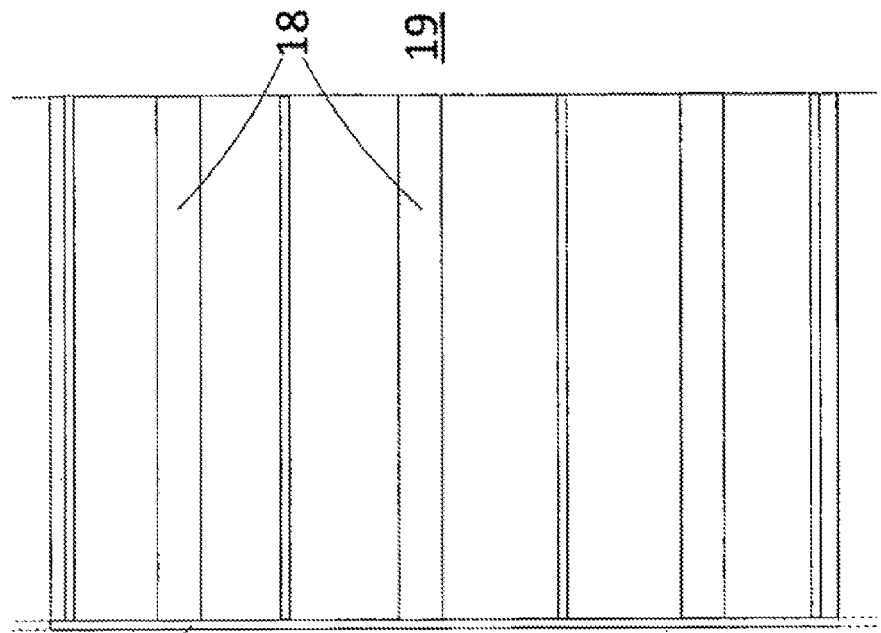
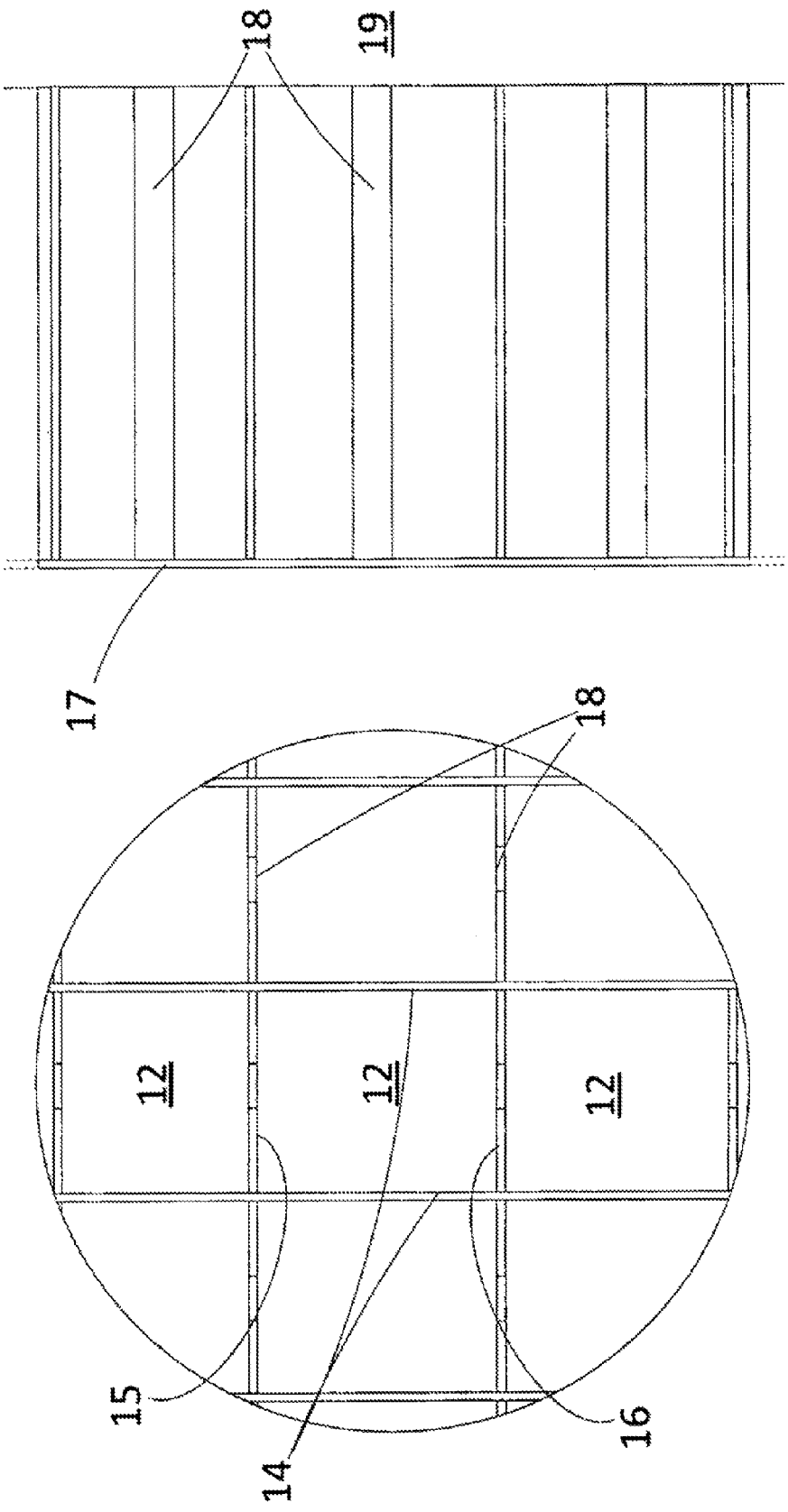

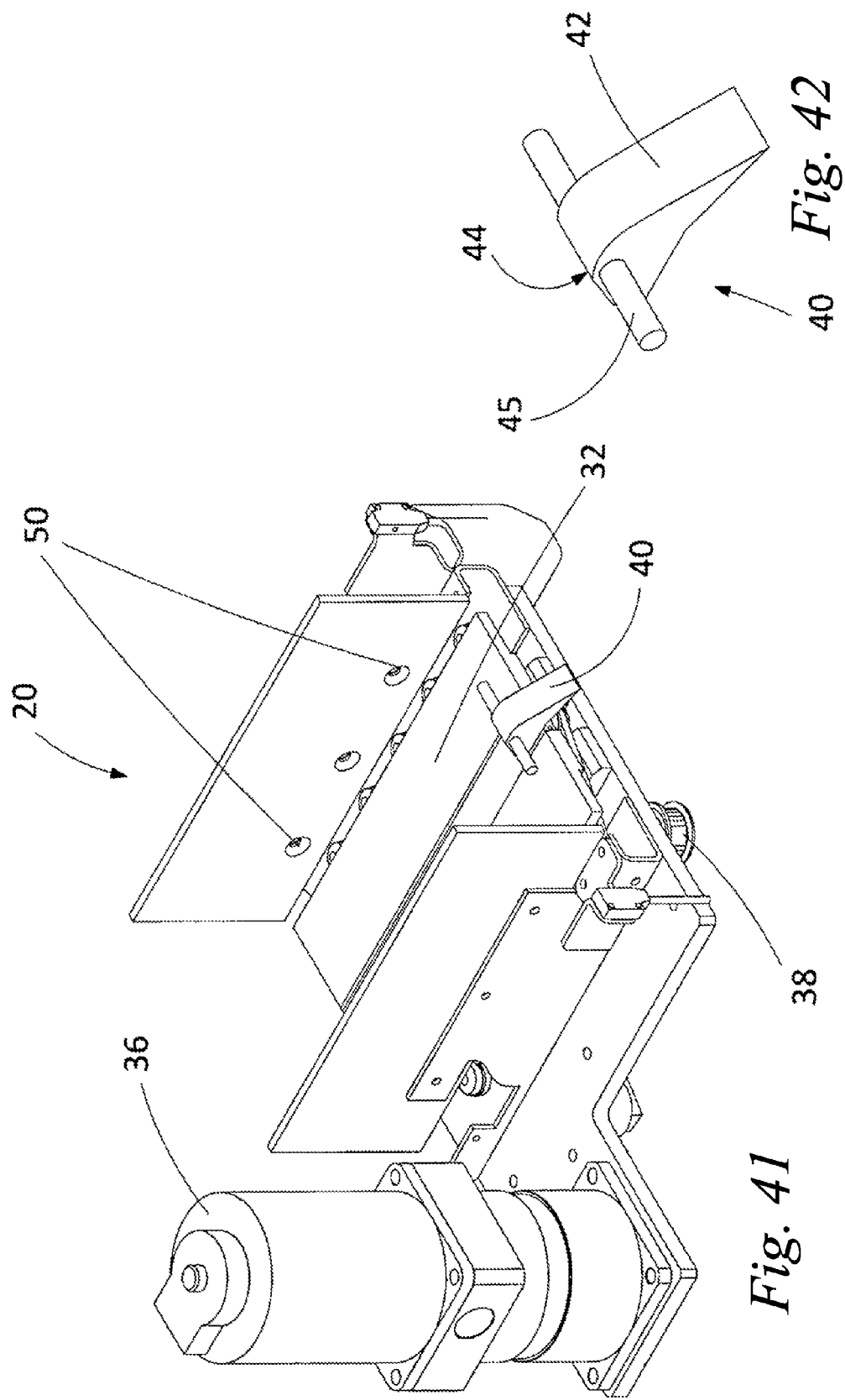

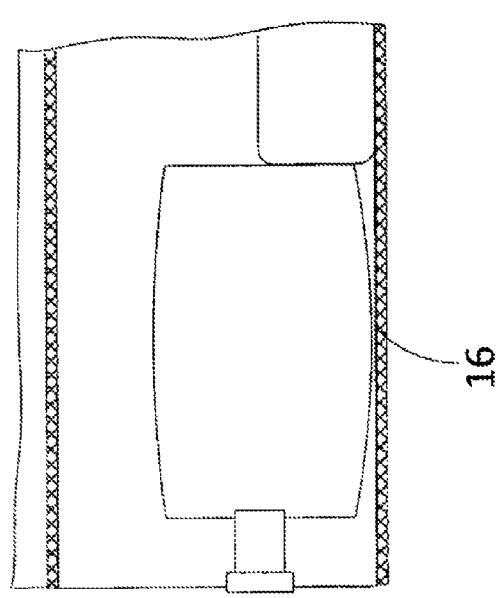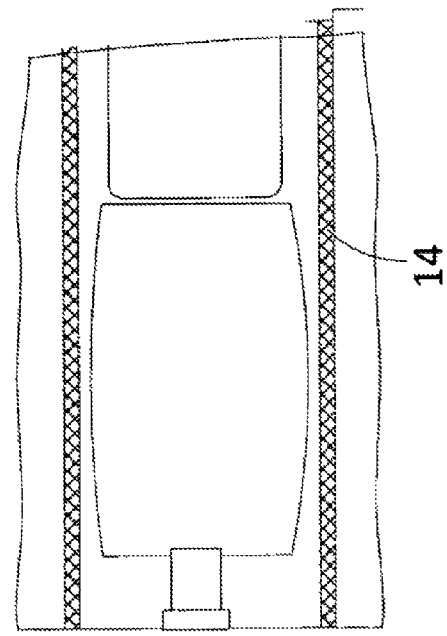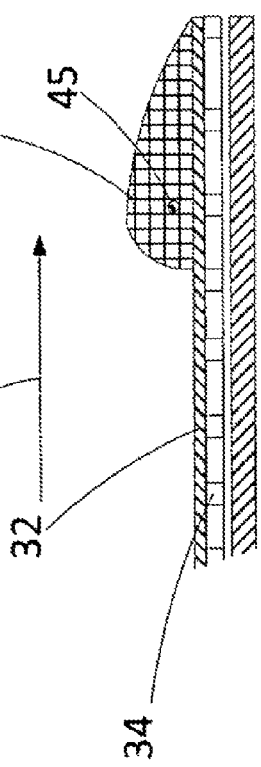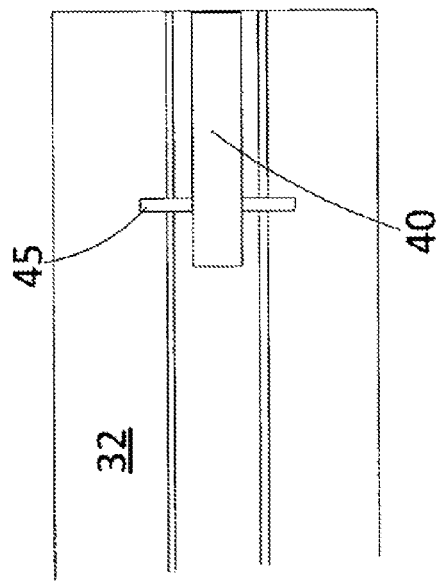
Fig. 44
Fig. 45

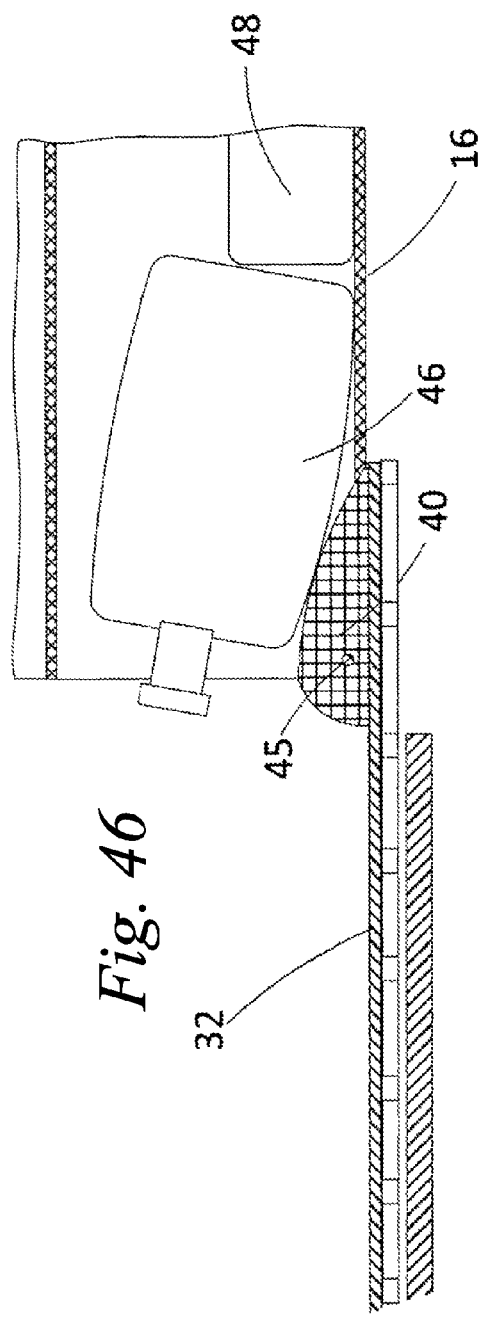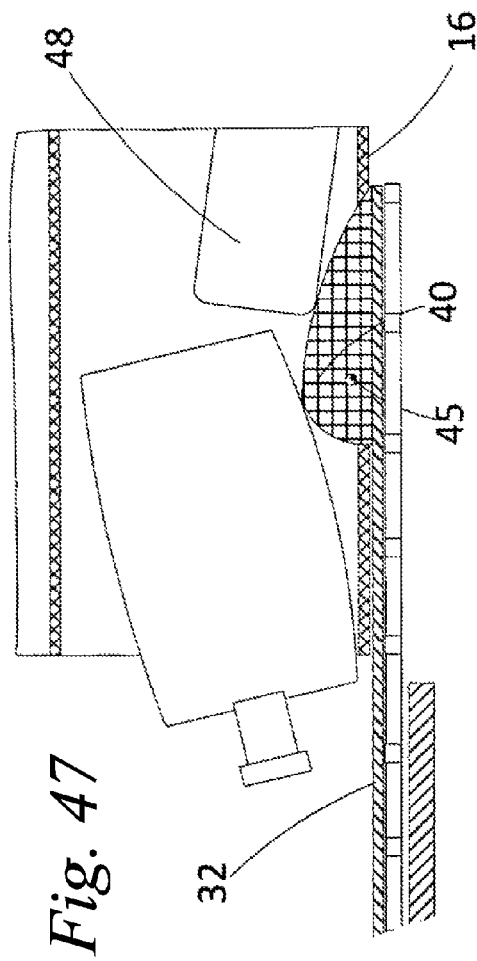

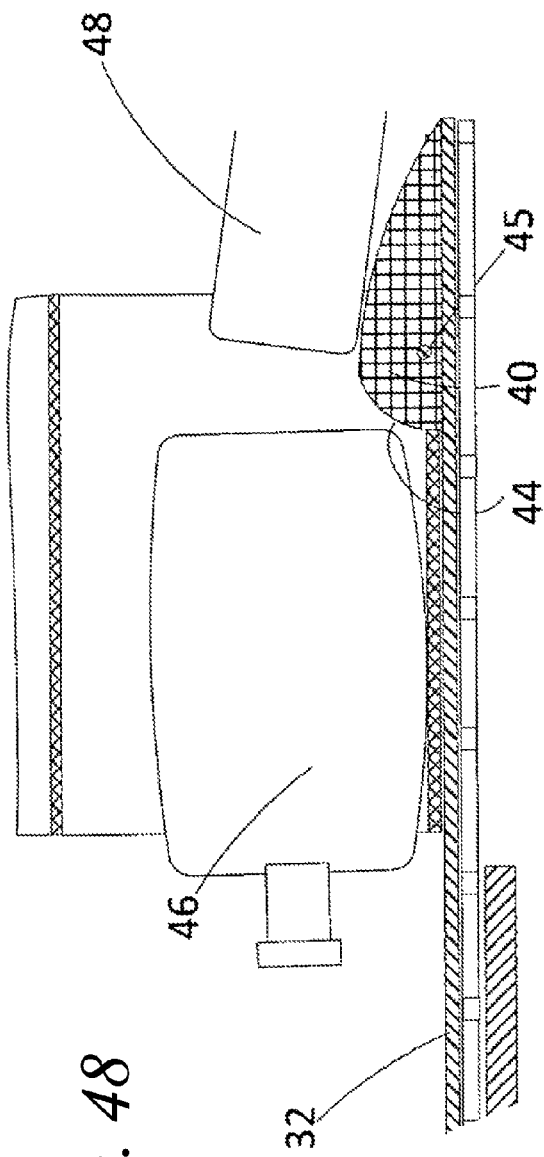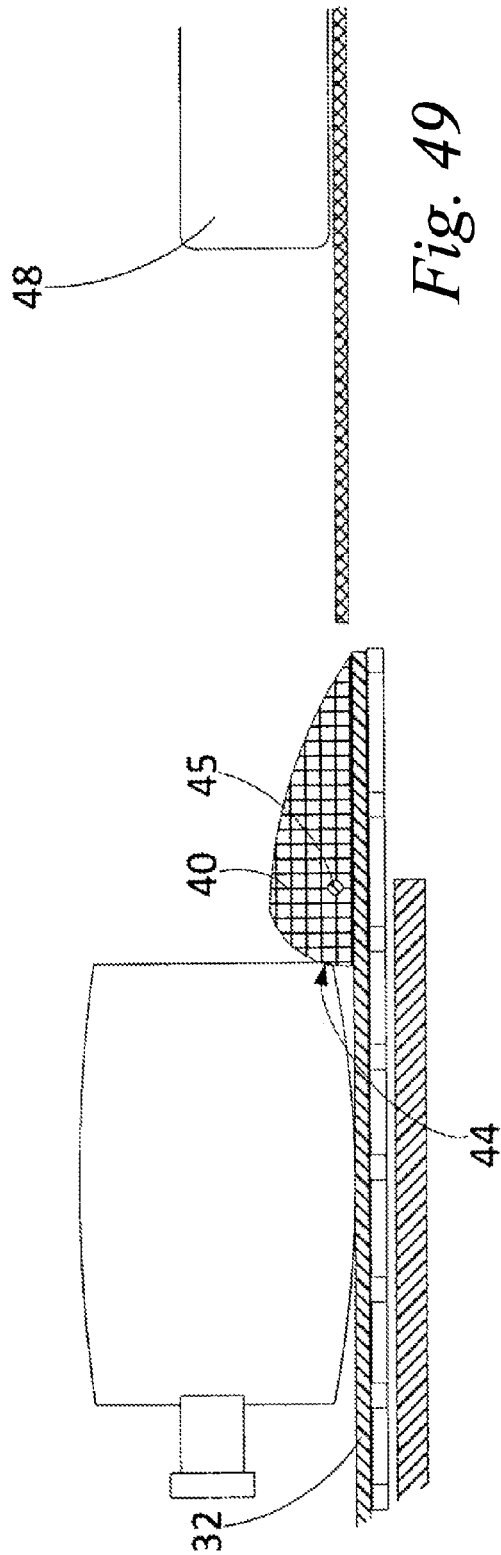

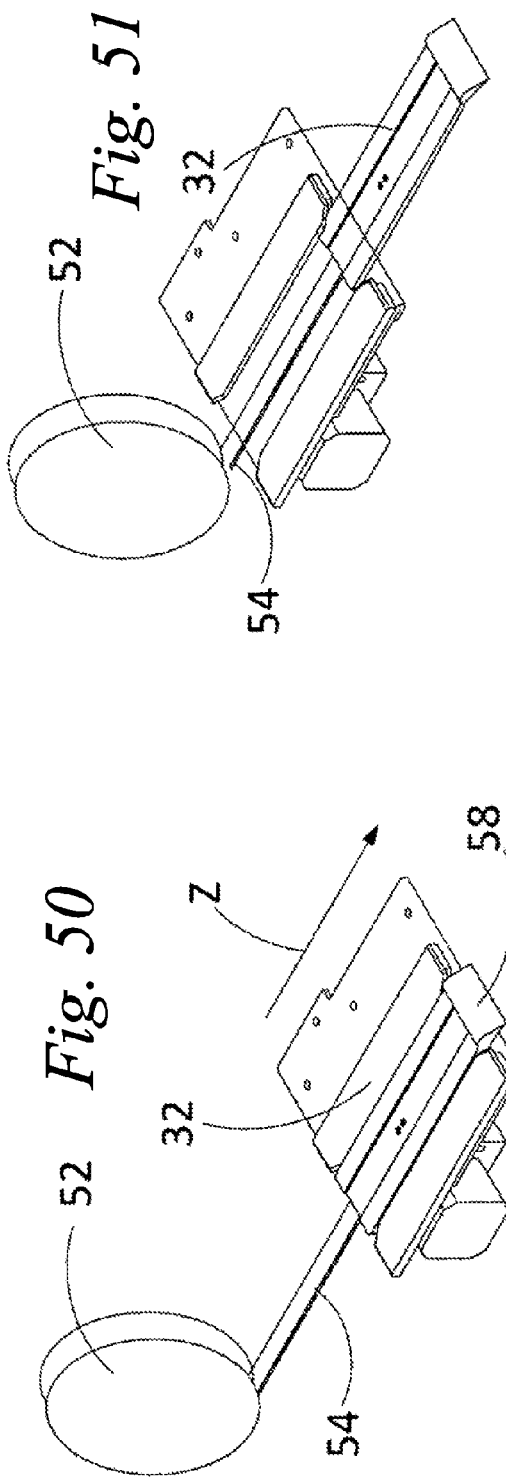
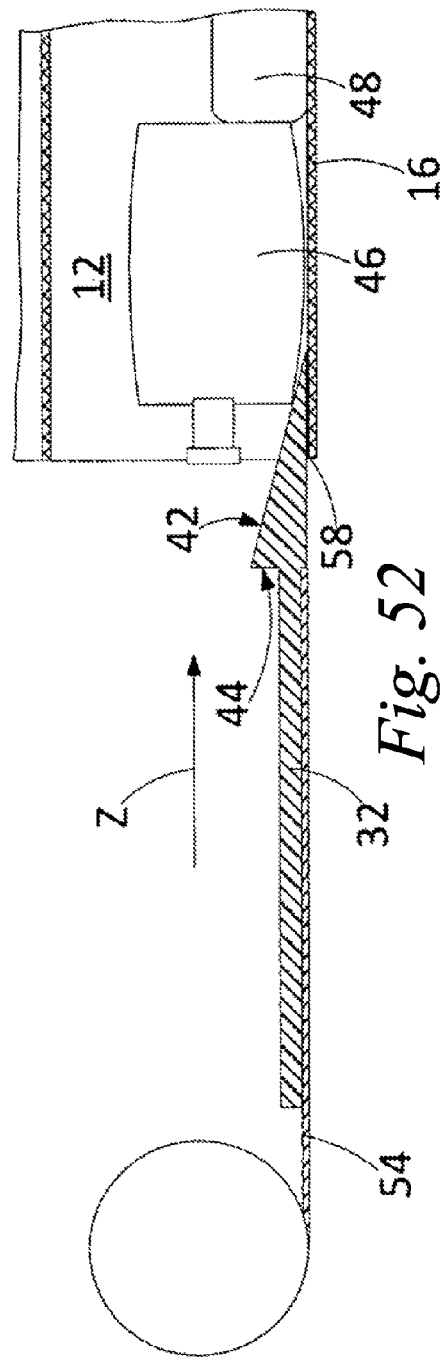

VENDING MACHINE CONTAINER LABELING AND DISPENSING METHOD

CROSS-REFERENCE TO RELATED APPLICATIONS

This application is a continuation of U.S. patent application Ser. No. 13/173,869, filed on Jun. 30, 2011, titled "Vending Machine for Storage, Labeling and Dispensing of a Container," and claims priority to, and the benefit of, U.S. Provisional Application Ser. No. 61/360,509, titled "METHOD AND APPARATUS FOR LABELING," filed on Jul. 1, 2010, which is incorporated herein by reference.

FIELD

Implementations disclosed herein relate to dispensing drugs, and further relate to an automated apparatus for delivering a medicament to a patient/user, the apparatus being adapted to be sited at a location remote from but connected to a pharmacy support station and for videoconferencing by the user to pharmacy support staff at the pharmacy support station, the apparatus including a pick head arrangement for picking, loading and labeling packaged drugs that are dispensed from the apparatus to the user under control of the pharmacy support staff.

BACKGROUND

In this specification, the term "medicament" encompasses drugs and any and all other materials dispensed subject to presentation of a prescription.

The traditional means of dispensing medication involves a doctor meeting with a patient and prescribing drugs or medications based on a particular diagnosis. A prescription is then hand written or printed, and generally must be signed. The doctor generally updates the patient's 10 paper file, and the patient takes their prescription to a pharmacy to be filled.

Under this traditional system of dispensing medication, various problems arise. For example, a pharmacy can encounter a problem with a prescription because of the illegibility of the handwriting, which requires a call back to the doctor for clarification. There is also a potential problem where the wrong prescription is filled if the pharmacy does not do the call back to clarify a prescription. Further, potential adverse drug interactions are dependant on the doctor manually researching or knowing the interactions in order to recognize the possible issues and alter a prescription on that basis. Under the current system, there is no notification of patient compliance or drug substitution, nor is there notification of so-called 'double doctoring' or 'multi-pharmacying.'

In recent years, two major advancements have occurred in the field of medicament dispensing. The first is electronic prescription capturing methods, systems and apparatus, which improve the overall accuracy and patient record keeping associated with prescribing drugs. The second is the arrival of automated apparatus, typically configured as kiosks, which automatically dispense medication and are located for convenient patient access (for example, in doctors' offices and medical clinics) and are networked into a central computer system for inventory control and management. In this regard, reference may be made to PCT Application No. PCT/CA2007/001220, published on 17 Jan. 2008 under Publication No. WO 2008/006203 (hereinafter, the "PCT Application"), titled "Method, System and Computer Program For Dispensing Drugs," which is specifically incorporated by reference herein.

More specifically, the PCT Application describes a system having a server computer, a database of patient information linked to the server computer, a computer input means linked to the server computer operable to generate the script for a drug prescribed to a user, and an automated apparatus for dispensing medicaments (referred to in the PCT Application as a robotic prescription dispensary) operable to recognize a human and/or machine readable description in the script, enabling cross referencing between the description and the patient information to validate dispensing the drug to the user on the basis of the input script. A doctor in a clinic can use the computer input means (for example, a tablet computer) linked to the server to input the appropriate prescription information, or accept certain prescription information from the database as being applicable in the particular case for a particular patient. Further, the doctor's tablet computer may display the patient information, e.g., drug history, insurance coverage, etc., and a printer module can print the script as a paper print-out. The server computer and database enable storing, compiling and retrieval of relevant patient information, for example, the patient's personal information such as name and address, as well as health-relevant information such as diagnostic history and drug history. Access to the database can be provided to both the doctor and the automated apparatus for dispensing medicaments via the server, via a secure connection, or via a link between the system and a clinic's existing clinic management system or patient database.

The PCT Application further describes a method for dispensing drugs including generating a script for a drug prescribed to a user, whereby the script includes data elements in the form of a human readable description of the drug and the user and/or a machine readable description of the drug and the user. The script is input to automated apparatus for dispensing medicaments (identified in the PCT Application as a robotic prescription dispensary) which is operable to do the following: (i) recognize the human and/or machine readable description; (ii) authorize dispensing the drug to the user based on a validation means; and, (iii) dispense the drug to the user. The automated apparatus for dispensing medicaments is linked to the server computer enabling cross-referencing between the machine readable description and the patient information to validate dispensing the drug to the user on the basis of the machine readable description.

The described apparatus also includes a user interface, a teleconferencing or videoconferencing means enabling communication between the user and a human validation agent, and a scanning means for capturing an image of the script so that it, if needed, it can be viewed by a human validation agent, such as a licensed pharmacist communicating in the system and with the apparatus from a remote location to the apparatus, to approve a prescription. The user interface of the dispensary apparatus provides detailed and clear instructions to guide the user.

An authentication means confirms the identity of the patient, for example, by prompting for a personal identification number or by biometric means or by associating certain questions to answers provided by the patient that identify the patient to the apparatus, and cross-referencing this information with the patient information stored on the networked database. Once the patient is recognized, the dispensary apparatus prompts the user for a script and the apparatus processes the user-input script either by the above-mentioned human validation agent or by processing the machine readable description (which may be a bar code). This information can be verified with the server and the database. The apparatus may also interface with the server to adjudicate an insurance claim and determine the amount payable by the patient. The patient either accepts or rejects the transaction. If the transaction is accepted, the apparatus interfaces with the server to transact a payment, for example, by prompting the patient for credit card information. Prescription labels and receipts are printed. The apparatus confirms that the drug is correct and drops it into a dispensing area for retrieval by the user while retaining the script in a lock box, and verifies that the purchased drug product has been retrieved. Further, the apparatus may also print and/or provide to the user educational materials relevant to the particular prescribed drugs it dispenses to the user.

The PCT Application further describes that an automated apparatus for dispensing medicaments may, for example, be located in a doctor's office or clinic, and electronically linked to a computer input means used by a doctor prescribing a drug to a patient, for example, either directly or via a server so that a patient can obtain prescribed drugs without having to attend a pharmacy or drug store.

To date, however, the utility of such known medicament dispensary apparatus has been restricted by the limited variety of medications that may be remotely stored or robotically dispensed by them. Therefore, patients, especially those requiring nonstandard dosing, multiple medications, medications requiring special storage or some form of pre-dispense preparation, are often faced with their medication requirements not being able to be fulfilled at such a known apparatus, thereby requiring a trip to a pharmacy for the balance of the prescription and negating the utility of such a dispensary apparatus.

In such a medicament dispensary, it is desirable that the first script ratio is high; i.e. that as many users as possible who present prescriptions with a view to obtaining medicaments will be able to fill their prescription at the kiosk without requiring a trip to the pharmacy.

The first script coverage ratio really depends on how much variation there is in the population of prescriptions that will be presented at the kiosk and it depends on the range of medicaments available at the kiosk. With regard to range of medicaments, the ratio can be increased by increasing the number of different medicaments that can be dispensed at the kiosk. For example, if there are pills for suppressing headaches and there are pills of a different nature for easing rheumatic pain, then the first script coverage ratio is higher than if there were only either one or the other of the head ache pills and the rheumatic pain pills. Similarly, if there are a variety of medicament delivery mode capabilities such as pill delivery and liquid delivery, then the first script ratio is likely to be higher than if there were just one medicament delivery mode capability. Also if there are a variety of amount dispensing capabilities, such as the capability to dispense any number of pills between 1 and 50, then the first script ratio is likely to be higher than if there were just a single pill dispensing capability fixed at, say, 20 pills.

Clearly, if a kiosk is equipped to dispense every conceivable medicament, has every conceivable delivery mode capability and has every conceivable amount dispensing capability, the first script ratio may approach 100%. However, increasing the kiosk capabilities in this way may yield diminishing returns if the expense and complexity of product and operation are also markedly increased. Additionally, adding these capabilities in such a way as to add significantly to the kiosk volume or footprint may present further expense and logistical problems in the sense of readily obtaining convenient and competitively priced sites for such kiosks.

Medicament packages to be dispensed at the robotically controlled dispensing kiosk may be prepackaged pill boxes, bottles or the like having a range of sizes, shapes, weight, weight distribution and surface condition, all of which may create handling problems for a robotic system. Drug companies frequently change packaging, so control algorithms may become ineffective if a control algorithm is based on the product packaging. A control algorithm that prescribes a handling method based solely on pre-recorded product package information (weight, size, etc) is prone to error. To reduce package handling problems, uniform style and shape of outer-packaging can be applied to medicament products, although this is not preferred as it adds additional handling and expense, may introduce other errors, and results in extra packaging materials. Ideally, the control algorithms and the package handling hardware utilized throughout a package picking process should be as flexible as possible commensurate with other demands of the dispensary kiosk.

In known medicament dispensary kiosks for dispensing bottles or packages of drugs or other medicament packages, the packages are typically stacked in a row column rack of bins. To pick a package from a bin, a pick head is driven in X and Y directions to a desired XY position corresponding to the selected bin. A platform forming part of the pick head is then moved in the Z direction to pick the package from the selected bin.

In a prior implementation of a pick head as described in co-pending Canadian Patent Application Serial No. 2,639,239, filed on Aug. 29, 2008, titled "Automated Modular Apparatus For Dispensing Medicaments," with a pick head at a desired XY position and a platform adjacent the target bin, the platform is moved to a position underlying a slot formed in a lower wall of the target bin. In the package pick action, after the platform is driven a sufficient distance rearwardly in the Z direction, the platform is raised so that an upwardly extending hook on the platform is brought to a position immediately behind the package to be picked. The package to be picked is then hooked out of the selected bin by driving the platform forwardly out of the rack of bins.

Once the picked package is on the platform, further investigation is made to ensure the package is really the one whose selection is desired. Typically, this might include checking a bar code affixed to the package and/or examining physical characteristics of the package such as its shape or weight. The platform, with the package supported upon it, is then moved to a rest position on the pick head whereupon the pick head is driven to another part of the apparatus as part of the dispensing procedure.

Within a medicament storage kiosk of the type described in the co-pending Canadian patent application 2,639,239, it is desirable to have the pick head and its operation occupy a small space so that as much rack space as possible can be used for the storage of medicaments. In the pick operation described previously, the raising of the platform once it has been driven under a bin means that a layer of space under each row of bins must be reserved. In addition, the 3-part platform movement—platform moves rearwardly, platform moves upwardly, platform moves forwardly—is a relatively complex procedure.

It would be valuable if at least a part of the layers of space under each row of bins which are reserved as the platform lifting space could be used for further storage. It would be valuable also if a simpler procedure could be implemented for picking packages from the bins.

As described in the PCT Application, and in co-pending U.S. Provisional Application Ser. No. 61/170,642, filed on Apr. 19, 2009, titled "Automated Apparatus for Dispensing Medicaments," which is specifically incorporated by reference herein, a medicament dispensary kiosk may be located in a doctor's office or clinic. The interaction between a patient and the kiosk user interface coupled with access to the various networked functionalities means that a patient can obtain prescribed medicaments without having to attend a pharmacy or drug store. The described medicament dispensary apparatus delivers medicament packages to users. Such packages may take the form of bottles, boxes, shrink wrap foil containers, etc., and therefore can be of a range of shapes and sizes.

For medicament dispensing kiosks, each package of dispensed medicament may need has to be labeled. Medicament package labels are typically of a standard shape and size to enable them to be passed through a printer, and must contain critical patient and medication information in conformance with industry standards and offering little scope for variation in shape, size or materials. Such labels are typically applied by running pressure sensitive adhesive back coated labels on a peal-away carrier through a label printer and transferring the printed label to the medicament container such as a bottle or box. Known label transfer methods have used sponges, vacuum, sponges and vacuum in combination, transfer media, transfer roller and pressure pads. There is a need for reliable accurate placement and adhesion of standard flat labels to dispensed medicament products.

In view of these and other user requirements or preferences in the marketplace, an improved automated apparatus for interactively dispensing a labeled medicament package to a user is desirable.

SUMMARY

Implementations disclosed herein provide a method, system and apparatus for dispensing drugs quickly, conveniently, securely, and accurately and at less cost than traditional pharmacy-based dispensing systems.

In one aspect of implementations disclosed herein, a method, system and apparatus for dispensing drugs enables doctors to prescribe drugs to patients by generating a script. The script is a unique identifier having one or more data elements. The unique script in turn allows a patient to fill their prescription via a robotic prescription dispenser. The robotic prescription dispenser recognizes the one or more data elements, and the drugs are dispensed on that basis.

Preferably, the script has two data components: (i) human readable descriptions for a pharmacist to dispense the prescribed drugs; and (ii) machine readable descriptions for the robotic prescription dispenser to dispense the prescribed drugs. The two components allow the patient choice when filling their prescription.

According to another aspect of implementations disclosed herein, the robotic prescription dispenser is located in the doctor's office or clinic and is electronically linked to the doctor, either directly or via a server. As a result, implementations disclosed herein advantageously allows a patient to obtain prescribed drugs without having to attend a pharmacy or drug store. According to an implementation disclosed herein, the doctor uses a computer input means (for example, a tablet computer) which is linked to a server to input the appropriate prescription information, or accept certain prescription information as being applicable in the particular case. The doctor enters the prescription into the tablet computer which displays the patient information, e.g., drug history, insurance coverage, etc. To the extent that an implementation disclosed herein enables access to personal information, the system incorporates known technology for maintaining privacy.

In a particular implementation disclosed herein, a printer module is provided to print the script as a paper print-out having text and a machine readable bar code or the like. Alternatively, the prescription information can be loaded on a smart card or the like.

In a particular aspect of an implementation disclosed herein, the system includes a database for storing, compiling and enabling retrieval of relevant patient information, for example, the patient's personal information such as name and address, as well as health-relevant information such as diagnostic history and drug history. Access to the database is provided to both the doctor and the robotic prescription dispenser via the server, via a secure connection.

A patient seeking to fill a prescription provides the script to the robotic prescription dispenser, the robotic prescription dispenser having a user interface. At each step, the user interface provides detailed and clear instructions to guide the patient. An authentication means confirms the identity of the patient, for example, by prompting for a personal identification number or by biometric means or by associating certain questions to answers provided by the patient that identify the patient to the robotic prescription dispenser. Once the patient is recognized, the robotic prescription dispenser will prompt the patient for the script.

The robotic prescription dispenser processes the script, and optionally verifies information with the server and the database. In a particular implementation, the robotic prescription dispenser interfaces with the server to adjudicate any insurance claim and to determine the amount payable to the patient. The patient either accepts or rejects the transaction. If the transaction is accepted, the robotic prescription dispenser will interface with the server to transact a payment, for example, by prompting the patient for credit card information. Prescription labels and receipts are printed. The robotic prescription dispenser confirms that the medication is correct and drops it into a dispensing area while retaining the script in a lock box. The robotic prescription dispenser machine verifies that the medication has been retrieved. The robotic prescription dispenser optionally prints or provides educational materials to the patient relevant to the particular prescription drugs being dispensed.

Preferably, radio frequency identification ("RFID") device technology is implemented to track and control the dispensing of medication throughout the supply chain, including inside the robotic prescription dispenser.

Another particular aspect disclosed herein is an RFID based drug prescription or "RFID prescription". Specifically, the RFID prescription consists of an RFID that includes a unique serial number identifying a prescription, and certain other information required for processing a prescription. This information, in one particular implementation of an implementation disclosed herein, includes data required for authentication purposes in the context of a PKI (Public Key Infrastructure) means of authentication.

Preferably, the robotic prescription dispenser is in the form of a kiosk.

In a further aspect of an implementation disclosed herein, the robotic prescription dispenser includes an inventory level control means.

In a yet further aspect, an implementation disclosed herein enables a substantially automated prescription repeat service that can be offered through the mail, as an example. This is provided, for example, by integrating the described system with a system used by a mail order pharmacy to process repeat prescriptions of drugs.

According to one aspect of an implementation disclosed herein, there is provided an apparatus for delivering medicaments to users, the apparatus includes a drug vault having a pre-packaged product storage container for containing inventory pre-packaged medicament product, a bulk product storage container for containing inventory medicament in bulk form, and a control system operable to effect at least a part of a process to dispense bulk form inventory medicament from the bulk product storage container, to pack as a dispensed packaged medicament product the dispensed bulk form medicament, and to pick, label, and deliver medicament products to a delivery zone.

Preferably, at least a part of the control system is commonly deployed in handling both the pre-packaged medicament products and the dispensed bulk medicament products whereby to limit the volume and footprint of the apparatus. Preferably, the control system includes a medicament packaging module operable to dispense and package the bulk form inventory medicament as a dispensed medicament product that is one of a bottle, a box and a foil package. The apparatus can further include a metering mechanism operable to meter a selected amount of the inventory medicament in bulk form and to deliver the selected amount from the bulk product storage container.

The inventory medicament product can be stored in bulk form as individually dispensable items, with the metering mechanism operable to meter the selected amount of the inventory medicament in bulk form as a metered plurality of individually dispensable items. The metering mechanism can further include a singulator successively to take items from the individually dispensable items in bulk form and to deliver the taken items for packing, and a counter to count the number of items taken from the individually dispensable items in bulk form and delivered for packing. Typically, the individually dispensable items are one or more of pills, lozenges and capsules.

The inventory medicament product in bulk form may alternatively or additionally be stored in a bulk product storage container as a liquid. With such an arrangement, an alternative or additional metering mechanism is included that is operable to meter the inventory medicament in bulk form as a metered volume of the liquid. For liquid medicament, the bulk storage container is preferably within a refrigerated zone whereby liquid medicament stored therein is maintained at a lowered temperature to prevent heat-induced deterioration thereof.

The apparatus may further including a treatment mechanism operable to alter the inventory medicament product in bulk form from an inventory state to a dispensing state prior to the inventory medicament product in bulk form being dispensed and packaged as the dispensed packaged medicament product. For example, the treatment mechanism can be operable to effect at least one of mixing, agitating and diluting of the inventory medicament product in bulk form.

Preferably, the apparatus includes a user-interface module configured to receive prescription information input from a user, a control module to interpret the prescription information and to issue commands to the control system on the basis of the received prescription information, thereby to cause the control system to select between picking and delivering the pre-packaged medicament product to a delivery zone, and picking and delivering the dispensed medicament product to the delivery zone. The apparatus may have a network interface for connection of the apparatus into a network, the network interface operable to transmit state of the apparatus information onto the network and operable to receive command information from the network for control of the control system.

The drug vault may be configured for secure storage of the medicaments, and be connected to the user-interface module, with the user-interface forming a front end of the apparatus and the drug vault forming a back end of the apparatus.

The apparatus may include a product labeling module configured for storing a stock of labels and for labeling a medicament product to be dispensed by the apparatus, the product labeling module operable to suspend a label from the stock of labels, and having an applicator for applying the label to the medicament product, the control system operable to transport the medicament product to the suspended label, and to align a front edge of the label with a predetermined contact start point on the medicament product.

The apparatus may have a validation unit operable within the network to validate the medicament products, the control system configurable to present medicament products to the validation unit for validation of the delivered products. For example, the validation unit may be operable effect one or more of weighing the medicament product presented thereto, monitoring a bar code on the medicament product presented thereto, and recording an image of the medicament product presented thereto.

Preferably, the automated apparatus communicates with a remote server linking the apparatus to a computer network, the apparatus having an identification unit to read and recognize a script for a prescribed medicament for a user of the apparatus. The apparatus is preferably configured for receiving through the computer network information regarding the user, the medicament and/or other apparatus of the network.

The control system can be configured for communicating in the network and may have means for accessing the user-interface module and the drug vault module, the accessing means has a plurality of sensors for providing positional feedback information to the control system for controlling the accessing means, picking the medicament from the drug vault module and delivering the medicament to the user-interface module for delivery to the user. The user-interface module and the drug vault module are preferably dimensionally compatible for interconnectability of multiple user-interface modules and drug vault modules in multiple combinations.

Preferably, the control system includes a state based machine configured to use a state table having states for controlling the control system, the states being associated with the positional feedback information provided by the sensors and based on behaviors to be applied by the accessing means to pick the medicament from inventory in the drug vault module. The control system may apply the behaviors according to increasing levels of aggressiveness to achieve success in picking the medicament from inventory, wherein the success is primarily defined to require no jamming of the control system.

The network may be a neural network having a dynamic knowledge base of information, including learned information, pertaining to medicaments in inventory in the apparatus and on-going behaviors, and their results, of control systems in the network used for picking medicaments from inventory, and the computer-controlled control system may use the knowledgebase information for controlling the accessing means.

The user-interface module is preferably configured for staged security level access by a human operator whereby a first level security access is restricted to access pre-selected components of the front end user-interface module only and a second level security access includes access according to the first level security access and access to the control system and the drug vault module including the inventory thereof.

The drug vault may include a refrigerated storage module for storing medicaments in inventory in a controlled refrigerated environment, the refrigerated storage module having one or more temperatures sensors for monitoring the refrigerated environment and the apparatus communicates information from the temperature sensor(s) through the network for centralized action.

A secure transfer container can be provided for secure transfer of medicament product therein from a medicament distribution center to the automated apparatus. The secure transfer container can be configured for receipt by the control system and self-loading by the control system of the medicament product from the secure transfer container to placement of the medicament product into inventory in the drug vault module. The secure transfer container is configured to restrict access to the medicament product therein to only the distribution center and the control system whereby a common carrier may be used for transporting the secure transfer container. The secure transfer container may be insulated and refrigerated, and have a solid state cooling device and means for temperature monitoring and configured for powering by means of an external power supply.

According to another aspect of an implementation disclosed herein, there is provided a method of configuring a medicament dispensing kiosk for a predetermined population of issued prescriptions, the method including storing at the medicament dispensing kiosk a first plurality of medicaments selected from a first larger set of medicaments, installing at the medicament dispensing kiosk a second plurality of medicament delivery mode capabilities selected from a second larger set of medicament delivery mode capabilities, and selecting a first combination of the first plurality of medicaments and the second plurality of medicament delivery mode capabilities to have at least a first predetermined fraction of the predetermined population of issued prescriptions fillable by the first combination.

The method of configuring may further include installing at the medicament dispensing kiosk a third plurality of amount dispensing capabilities selected from a third larger set of amount dispensing capabilities, the method can include selecting a second combination of the first plurality of medicaments, the second plurality of medicament delivery mode capabilities, and the third plurality of amount dispensing capabilities to have at least a second predetermined fraction of the predetermined population of issued prescriptions fillable by the second combination of the first plurality of medicaments, the second plurality of medicament delivery mode capabilities and the third plurality of medicament amount dispensing capabilities.

According to one aspect of an implementation disclosed herein, there is provided a storage apparatus having a rack of storage bins, a pick head including a platform, a pick head drive unit to drive the pick head to an access location corresponding to a selected bin, and a platform drive unit to drive the platform into and out of the rack from the access location, the platform having a cam formation for lifting a package stored in the selected bin when the platform reaches an actuation position in the course of the platform entry, the platform having an engagement means to engage the selected package when the platform reaches a withdrawal position in the course of platform entry, the engagement means, in the course of the platform exit, acting to drag the package out of the selected bin.

According to another aspect of an implementation disclosed herein, there is provided a method for picking a package stored in a selected bin of a rack of storage bins, the method including operating a pick head drive unit to drive a pick head to an access location corresponding to the selected bin, operating the platform drive unit to drive the platform into and out of the rack from the access location, by means of a cam formation on the platform lifting a package stored in the selected bin when the platform reaches an actuation position in the course of the platform entry, by means of an engagement means on the platform engaging the selected package when the platform reaches a withdrawal position in the course of platform entry, and by means of the engagement between the engagement means and the package dragging the package out of the selected bin in the course of the platform exit from the rack.

According to one aspect of an implementation disclosed herein, there is provided a method of applying a label having an adherent coating to a package having a front and sides to stick the label to the package, the method including bringing the label and the package together so that the label contacts the package to establish a tacking contact at a predetermined position of the label relative to the package, and effecting a relative movement of a conformable tamp block against the label and package to apply the label to the package, the tamp block having a first element articulated to a second element, a first part of the movement of the tamp block effective to sandwich a first area of the label between the first element of the tamp block and the front of the package, a second part of the movement effective to articulate the second element relative to the first element to a position adjacent a side of the package and to deform the second element against a second area of the label to fold the second area against a side of the package and to sandwich the second area between the second element of the tamp block and the side of the package.

Preferably, in the second part of the movement, deformation of the second element is constrained by a constraining member whereby to direct the movement of the second element against the second area of the label. The constraining member can be fixed to the tamp block or can alternatively be mounted to an external frame. The tamp block can be of a general of U form, the first element of the tamp block being a cross piece of the U and the second element of the tamp block being uprights of the U. Preferably the first part of the movement and the second part of the movement occur successively as a single unidirectional movement of an actuator mechanism attached to the tamp block.

The method can further include bringing the label to the package from a reel of labels self adhering to a liner by passing the liner around a roller, the label having a stiffness greater than a stiffness of the liner, whereby, on passage of the liner around the roller, the difference in stiffness acts to overcome adherence between the label and the liner and to release the label from the liner. Preferably the stiffness of the label is sufficient to suspend the label in a predetermined position in the course of the release, to permit the bringing of the label and the package together so that the label contacts the package to establish the tacking contact at the predetermined position of the label relative to the package.

According to another aspect of an implementation disclosed herein, there is provided apparatus for applying a label having an adherent coating to a package having a front and sides to stick the label to the package, the apparatus including a supply reel of label stock having labels adhering to a liner, first transport mechanism to bring labels to a printing zone and to a labeling zone and to bring containers to the labeling zone, the transport mechanism operable to bring a package and a label together so that the label contacts the package to establish a tacking contact at a predetermined position of the label relative to the package, the apparatus further including a second transport mechanism to effect a relative movement of a conformable tamp block against the label and package to apply the label to the package, the tamp block having a first element articulated to a second element for sandwiching a first area of the label between the first element of the tamp block and the front of the package, the tamp block having a second element movable relative to the first element for location adjacent a side of the package, the second element deformable to sandwich a second area of the label between the second element of the tamp block and a side of the package.

Preferably, the apparatus includes a constraining member to direct movement and deformation of the second element to apply pressure to the second area of the label sandwiched between the tamp block and the side of the package, with the constraining fixed to a stationary frame and also attached to the conformable tamp block. The first transport mechanism can be operable to bring the label to the package from a reel of labels self adhering to a liner by passing the liner around a roller, the roller adapted for operation with a label having a stiffness greater than a stiffness of the liner, whereby, on passage of the liner around the roller, the difference in stiffness acts to overcome adherence between the label and the liner to release the label from the liner. The first transport mechanism can be further operable to bring the label to a labeling zone and to suspend the label in a predetermined position in the course of the release, to permit the bringing of the package to the label to establish the tacking contact at the predetermined position of the label relative to the package.

According to one aspect of an implementation disclosed herein, there is provided an apparatus for delivering a medicament to a user from a vault holding packages of drugs. A control system in the apparatus is operable to pick and a package to a labeling module, where a label is applied having an adherent coating to the package and the label is detached from a web of backed labels using a suction device. The label is suspended by the suction device and the position and orientation of a package to be labeled with the label is monitored. The suction device is moved translationally and to alter its orientation so that a drive mechanism for driving the label and the package together results in the label being applied to the package at a desired position and angular orientation. The control system is operable to move the labeled package to a delivery zone.

Also disclosed is a method of applying the label having an adherent coating to the package to stick the label to the package. In disclosed implementations, a suction device is brought to a backed label and establishes a suction grip on the backed label, moving the backing while retaining the suction grip on the label to separate the label from the backing, repositioning the suction device to change a position parameter of the label from a first value to a second value, and bringing the label and the package together to stick the label to the package while retaining the second value of the position parameter. Preferably, the position parameter is at least one of position along a first axis, position along a second axis, and angular orientation, and the bringing of the label and the package together to stick the label to the package is on an axis substantially orthogonal to a plane containing the first and second axes.

According to another aspect of an implementation disclosed herein, an apparatus applies a label having an adherent coating to a package to stick the label to the package. The apparatus has a suction device and a first control mechanism for controlling the suction device, a store of backed labels and a second control mechanism for controlling the backed labels, and a third control mechanism for controlling the position of a package to be labeled, at least one of the first and second control mechanisms operable to bring the suction device and one of the backed labels together, the suction device operable to establish a suction grip on the one of the backed labels, at least one of the first and second control mechanisms operable to separate the suction gripped label from the backing, the first control mechanism operable to permit repositioning of the suction device to change a position parameter of the suction gripped label from a first value to a second value, and at least one of the first and third control means operable to bring the suction gripped label and the package together to stick the label to the package.

The apparatus can further include a package monitoring module for monitoring position of the package, the package monitoring module preferably having an output to the first control mechanism and an output to the third control mechanism. In a preferred implementation, the output to the first control mechanism is used to adjust relative positioning of the label and the package along a first axis and to adjust the suction device angular orientation, and the output to the third control mechanism is used to adjust relative positioning of the label and the package along a second axis.

The package monitoring module can further monitor characteristics of the package and have an output to control logic for generating inputs to the first and third control mechanisms, the control logic having an input from a memory module storing required label positioning data.

The package monitoring module can further include a machine vision module for generating an image of at least one of the unlabeled package, the label and the labeled package at one or more locations in the course of a labeling procedure. The machine vision module can include camera sub-systems and an image analysis module with the machine vision module forming one node in a communication network. The network can include a remote node having a viewing module for manual viewing of images generated at the machine vision module.

The second control mechanism can include a label reel, a take-up reel and a tensioning device. The suction device is preferably co-mounted with a tamping assembly including a deformable tamp block for pressing the label against the package.

BRIEF DESCRIPTION OF THE DRAWINGS

Implementations discussed herein will become more apparent from the detailed description set forth below when taken in conjunction with the drawings.

FIG. 5 is an example of a combination prescription label and receipt generated by the kiosk implementation disclosed herein;

FIGS. 11A-C illustrate an example of a control system of an apparatus implementation disclosed herein, with robot accessible waste container for placement and storage of suspect or damaged drug product, wherein FIG. 11A is a side sectional view of an example of a back end drug vault module with a control system therein, FIG. 11B is an exploded view of the control system portion of FIG. 11A and FIG. 11C is a sectional view of the control system of FIG. 11A;

FIGS. 13A through 13B are perspective views of front end user-interface modules of an embodiment the automated apparatus disclosed herein, as per FIG. 9, FIG. 13A shows a first level of access security for which the front of the apparatus remains closed so as to require software controlled function access in order to load inventory, with no physical access into the apparatus being provided;

FIGS. 13B1 through 13B3 show a second level of access security for which the front of the apparatus can be opened via controlled access to gain access to user interface components of the apparatus and to service the apparatus components accessible at this security level;

FIG. 13C shows a third level of access security for which the back end drug vault module of the apparatus, containing medicaments, is opened;

FIG. 15 illustrates an example of a pill counter module integrated into a bulk storage container for pill/capsule product, for counting pills to be dispensed by the apparatus implementation disclosed herein;

FIGS. 16A-B illustrate an example of a packaging module of the automated apparatus implementation disclosed herein, for packaging drugs to be dispensed to a user in bottles or foil packs, wherein FIG. 16A is a perspective view and FIG. 16B is a front view thereof;

FIGS. 17A-17B illustrate an example of a drug storage module of the automated apparatus implementation disclosed herein, showing multiple, standard slots for housing bulk storage cassettes therein, and an exemplary bulk storage cassette in one such slot, for retrieval by a robot of the apparatus and transfer to a packaging module, wherein FIG. 17A is a perspective view thereof and FIG. 17B is an exploded view of portion A of FIG. 17A;

FIGS. 18A-F illustrate a package labeling module of the automated apparatus implementation disclosed herein, wherein FIG. 18A illustrates a top view of a labeling assembly thereof, FIG. 18B illustrates a perspective view of the labeling assembly of FIG. 18A, FIG. 18C is an exploded view of section "C" of FIG. 18A, FIG. 18D is a sectional view taken at line "DD" of FIG. 18C, FIG. 18E is a sectional view taken at line "A-A" of FIG. 18A and FIG. 18F is a sectional view taken at line "B-B" of FIG. 18A;

FIGS. 21A-B illustrate an automatic self-loading of a delivered secure transfer container to the automated apparatus implementation disclosed herein, wherein FIG. 21A shows a control system receiving a secure transfer container and FIG. 21B is a view FIG. 21A;

FIGS. 22A-D illustrate an example of a secure transfer container for use with the automated apparatus implementation disclosed herein, wherein FIG. 22A is a perspective view, FIG. 22B is a right side view, FIG. 22C is left side view and FIG. 22D is a top view thereof;

FIGS. 23A-D illustrate a multiple slot, storage container rack comprising multiple, standard slots for housing bulk storage containers therein, showing one slot thereof containing five bulk storage containers with each container storing a different drug product, wherein FIG. 23A is perspective view, FIG. 23B is a top view, FIG. 23C is a side view and FIG. 23D is an end view;

FIG. 26 illustrates an exemplary sub-assembly of two inter-connected back end drug vault modules of the automated apparatus implementation disclosed herein, each module configured for modular construction of the apparatus;

FIG. 27A illustrates a front view of an example of a refrigerated storage module of the automated apparatus disclosed herein with cooling device, insulated sliding door, locking unit and air purge means provided by a dehumidifier and pressure control unit.

FIGS. 30A-B illustrate an example of a refrigerated secure transfer container for use with the automated apparatus implementation disclosed herein, wherein FIG. 30A shows a front view and FIG. 30B shows a side view thereof;

FIGS. 31A-C illustrate an example of a bulk storage container for prepackaged product of the automated apparatus implementation disclosed herein (one such container shown installed in the apparatus in FIG. 9), wherein FIG. 31A shows a perspective view, FIG. 31B shows a side view and 31C shows a front view thereof;

FIGS. 32A-B illustrate one example of a bulk storage container for storing pills and/or capsules therein, and having a pill/capsule counter integrated into the bulk storage container, wherein FIG. 32A is a front view and FIG. 32B is a side view thereof;

FIGS. 32C-H illustrate another example of a bulk storage container for storing pills and/or capsules therein, and having a pill/capsule dispenser and counter associated with the bulk storage container, wherein FIG. 32C is a view from above, FIG. 32D is a perspective view from above and one side, FIG. 32E is a view taken on the line B-B of FIG. 32H, FIG. 32F is a front view, FIG. 32G is a side view and FIG. 32H is a vertical sectional view on the line A-A of FIG. 32F;

FIGS. 33A-B illustrate an example of a bulk storage container for storing liquid medication, and having an integrated liquid pouring unit, wherein FIG. 33A is a front view and FIG. 33B is a side view thereof;

FIGS. 34A-C illustrate an example of a reconstitution bulk storage container for both storing a liquid medication and reconstituting that medication with another liquid prior to dispensing, wherein FIG. 34A is a front view, FIG. 34B is a side view and FIG. 34C is a perspective view thereof;

FIGS. 35A-B illustrate an example of a mixing bulk storage container for storing multiple different liquids and mixing them together prior to dispensing, wherein FIG. 35A is a front view and FIG. 35B is a side view thereof;

FIGS. 36A-B illustrate an example of a compounding bulk storage container for storing multiple different liquids and compounding and mixing them, for geometric reduction with a carrier, prior to dispensing, wherein FIG. 36A is a front view and FIG. 36B is a side view thereof;

FIG. 39 shows a detail from the front of a rack of bins forming part of the storage apparatus of FIG. 37;

FIG. 40 shows a top view of the detail of FIG. 39;

FIG. 41 is a perspective view of one embodiment of pick head for use in picking items from a storage bin;

FIG. 42 is scrap view of a part of the platform of FIG. 41;

FIG. 44 is a longitudinal sectional view through part of the pick head and adjacent storage bin according to an implementation disclosed herein;

FIG. 45 is a top view corresponding to FIG. 44;

FIG. 46 is a longitudinal sectional view corresponding to the view of FIG. 44, but showing a platform forming part of the pick head in a rearward position;

FIG. 47 is a longitudinal sectional view corresponding to the view of FIG. 33, but showing the platform in a more rearward position;

FIG. 48 is a longitudinal sectional view corresponding to the view of FIG. 44, but showing the platform in a package drop position;

FIG. 49 is a longitudinal sectional view corresponding to the view of FIG. 44 but showing the pick head and picked package retrieved from a bin rack;

FIG. 50 is a perspective view of a pick head according to another implementation disclosed, the arrangement shown with a platform forming part of the pick head in an unextended condition;

FIG. 51 is a perspective view corresponding to FIG. 50 but showing the platform in an extended condition;

FIG. 52 is a longitudinal sectional view corresponding to the views of FIGS. 50 and 51;

DETAILED DESCRIPTION

Vending Kiosk

Figure 1:
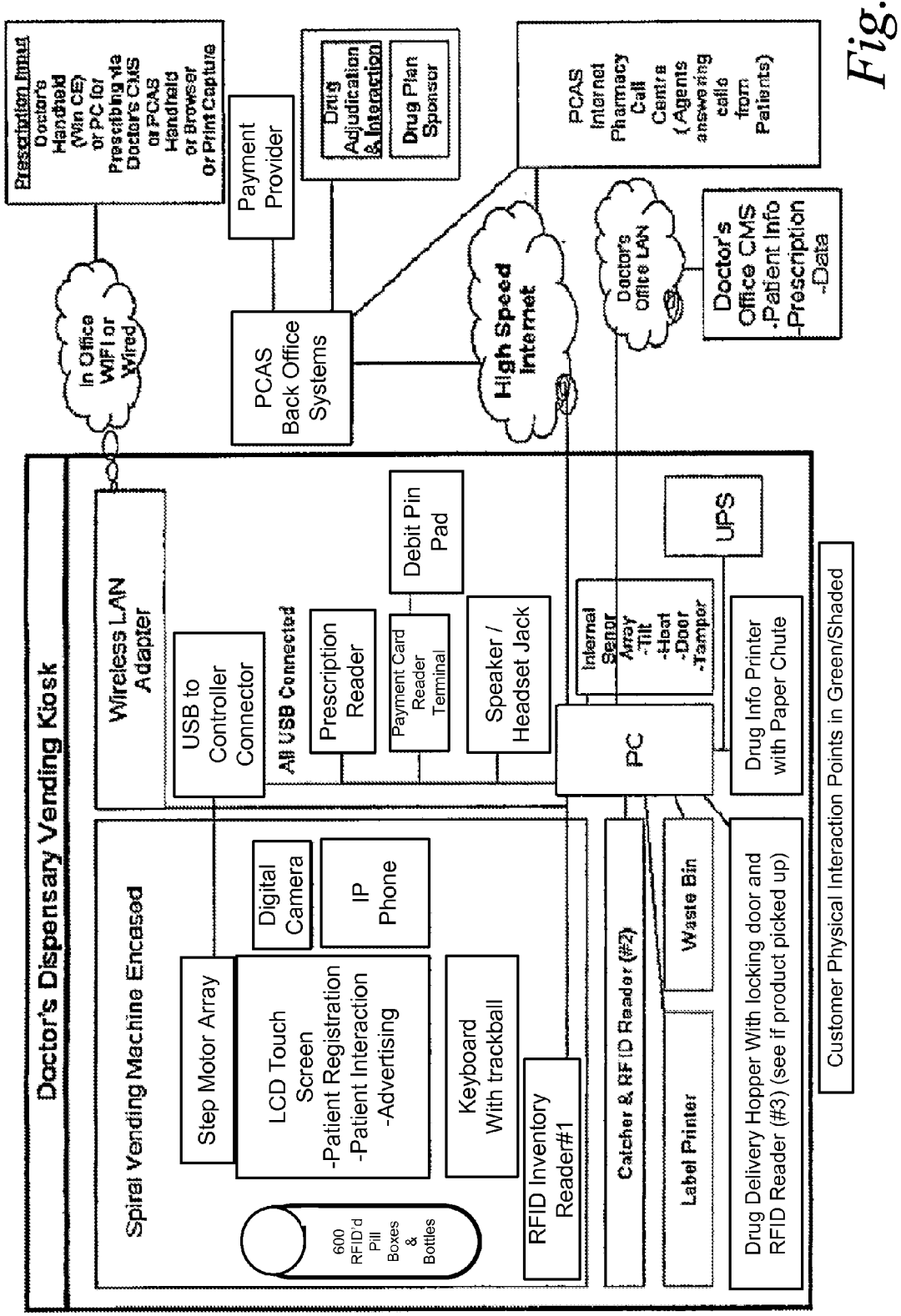
FIGS. 1 and 6-8 illustrates a schematic of an implementation disclosed herein.

One particular implementation of an apparatus disclosed herein is illustrated in FIG. 1. This implementation, referred to as a vending kiosk, is a robotic prescription dispenser. The casing of the kiosk is preferably formed of steel having a nylon powder coating with sleek finish. Lighted LED band accents can be provided around each component to identify the process steps. Hinges are preferably on the inside only, given that a secure body and foundation are required, and the base is preferably bolted to a concrete floor from four corners. Hardware devices should be mounted internally securely. Jacks located on the back provide for LAN, Wi-Fi and power. For the application control software, by way of example, a Microsoft WINDOWS™ based PC running custom designed application and controller software with off-the-shelf driver software can be used. The kiosk stepper motors are connected to the PC via a USB microcontroller. There is also a locking dispensing door mechanism. There is provided a prescription bar code reader that reads standard bar codes from printed prescriptions. Preferably, the reader can accommodate 8.5"×11" inch sheets as well as smaller printed prescriptions. A payment terminal will allow for various methods of payment, including debit and credit cards.

The kiosk preferably includes three RFID readers: one for product verification before labeling, one for inventory of the whole machine at once, and one for checking if product was collected from a bin. The catcher and RFID reader are arranged to catch the drug product, orient it, and then label it reliably. This system is generally required to support boxes and pill bottles. Similarly, a label printer must apply a label to both bottle and box reliably, and is preferably fault tolerant. A drug delivery hopper is ideally provided at a reasonable height to allow access for most users. Preferably there is a light inside. An RFID reader placed in the hopper determines if a product is not picked up by a user. The hopper is also subject to a lock, controllable from the PC, and that is tamper resistant and sturdy. If the RFID read of a bottle does not equal the prescribed drug, then the drug goes to a waste bin for collection by servicing. The kiosk software will automatically issue the error to the call centre, and an agent will decide to lock the machine and/or take over a session and speak to the consumer. It is generally required that the drug information printer print the drug information sheet from the adjudication database; and that the printer itself be sturdy, and notify the PC of ink status, jam and paper out conditions required. The printer is preferably mounted securely, and has a relatively large paper capacity (e.g., at least 500 sheets). A 15" or 17" touch screen is provided, for example, for the input, allowing a large text size and potential advertising space. A keyboard is also provided with a trackball for further input.

A camera is provided for security and for call centre interaction. Similarly, an internet-protocol phone is provided for call centre interaction, facilitating the system for blind patients. Alternatively, a speech output device may be implemented for instructing the patients via computer generated voice. An uninterruptible power supply (or "UPS") provides for a graceful shutdown in the event of a power failure (once a transaction is completed). A speaker and headset jack will be controlled by the kiosk application software. If the headset is connected then the speaker is off, and vice versa. A wireless LAN adapter is preferably provided to connect to the doctor's handheld and maybe office LAN. Cable connectors on the back of the machine include the power cord for the unit (e.g., need one cord out from UPS and internal power bar or UPS multiple plugs). A network cable female jack is provided connecting to high speed internet service. A network cable female jack is provided for LAN connection to the doctor's office, or handheld etc. Further, a male coaxial cable jack is provided for an antenna for Wi-Fi transceiver.

In a particular implementation of an implementation disclosed herein, the kiosk incorporates biometrics technology for authenticating the identity of a user of the kiosk. In another implementation disclosed herein, a system (including the kiosk) incorporates triage functionality that enables a user to be streamlined prior to a visit with a doctor. In a particular implementation disclosed herein, the kiosk is linked to a clinic management system that incorporates triage functionality. The kiosk doubles as a gateway for accessing medical services provided through the clinic in a more efficient way. The patient benefits by ensuing that s/he accesses the most appropriate medical services given his/her problem. The medical system overall benefits from more efficient allocation of available resources, based on the triage related considerations.

Another aspect disclosed herein integrates with a portable medical record to provide an economic model for financing improved electronic access to medical information, and improved technology tools for providing medical services.

Doctors Dispensary System

According to another implementation disclosed herein, a "Doctors' Dispensary System" is a collection of technologies that allows a doctor to create a prescription for a patient which can be used at a secure kiosk to dispense medication automatically.

Figure 2:
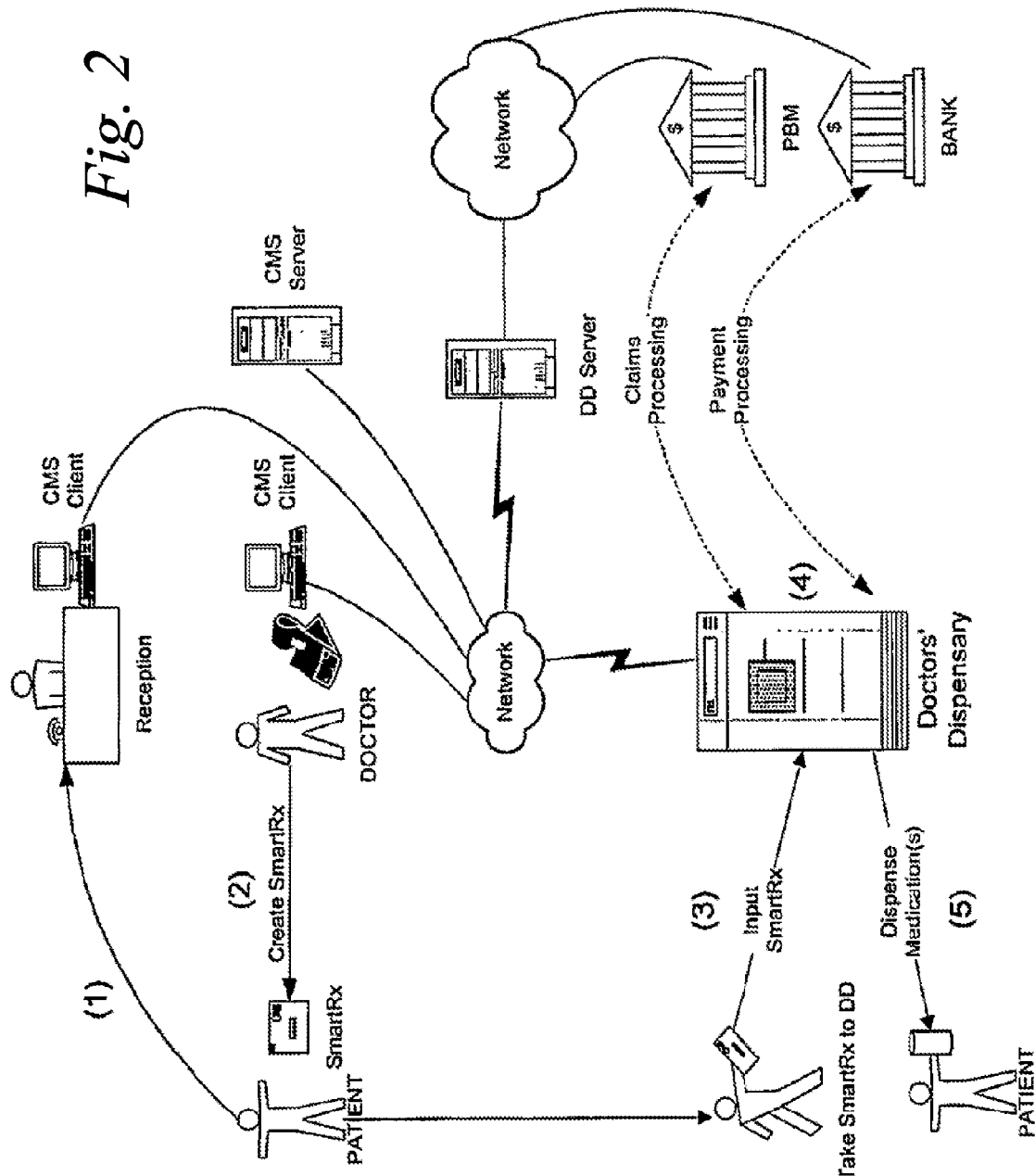
FIG. 2 illustrates conceptual diagram of a system and method in accordance with an implementation disclosed herein, referred to as Doctors Dispensary System.

As illustrated conceptually in FIG. 2, the Doctors' Dispensary ("DD") System enables a method that includes the following steps (not all of which are essential to the invention):

1. A patient provides drug plan information to a clinic's administrative staff before an appointment with their doctor;

2. In the appointment, the doctor creates a prescription script, or "SmartRx", for the patient;

3. The patient inputs a credit card and SmartRx into a DD kiosk;

4. The DD kiosk processes the claim and payment via an on-site DD server; and

5. The DD kiosk dispenses the medication(s) to patient.

Each of these aspects disclosed herein is discussed more fully below.

1. Acquisition o(Patient Drug Plan Information

The clinic's administrative staff collects or confirms the patient's drug plan information. To do this, the patient, who is already profiled in a clinic management system ("CMS"), checks in at clinic front desk for their doctor's appointment. The administrative staff queries the patient for drug plan information. A pamphlet or website should be provided to assist the administrative staff in capturing the correct drug plan information for the patient. A drug plan may assign unique ID numbers for each member of a family. The status of the drug plan number is then validated. The patient will be informed by the administrative staff if the drug plan is expired. This is done at this time since it can only be corrected at this point in time.

2. Creation of SmartRx

Figure 3:
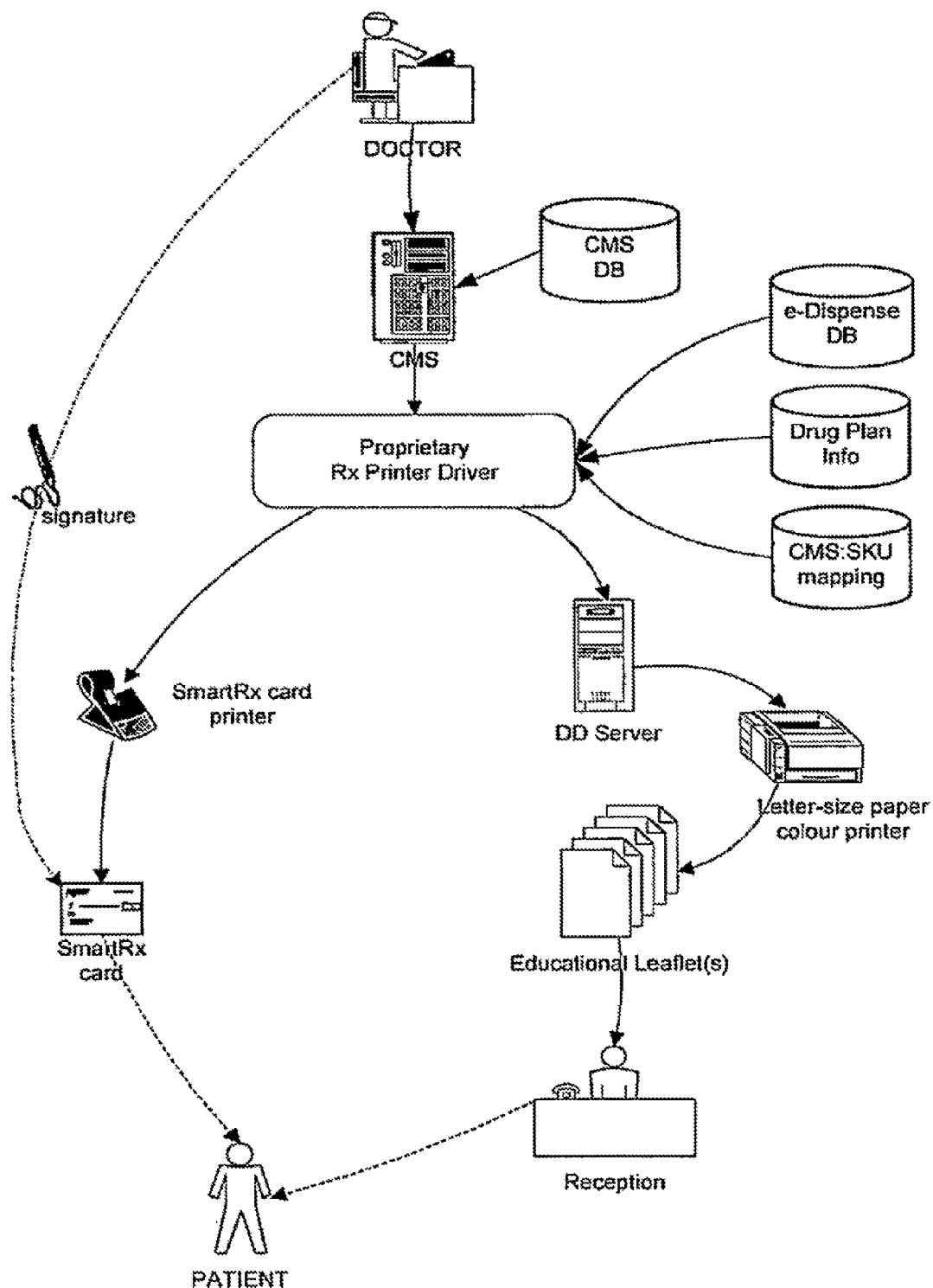
FIG. 3 illustrates to the creation of a SmartRx in accordance an implementation disclosed herein.

As illustrated in FIG. 3, the doctor prescribes medication by creating a SmartRx and by giving it to the patient. To do this, the patient goes to the doctor for the appointment and the doctor makes a diagnosis and selects a particular medication(s) to prescribe. The doctor uses the CMS to enter the prescription and prints it.

Preferably, the stock keeping units ("SKU") to dispense will be pre-determined Generally, a doctor will create a SmartRx (that can be used at the machine) only if the data in the prescription matches (or partially matches) an entry in the CMS SKU mapping. What needs to be determined is if there is an appropriate SKU in the kiosk that could be used for either: (i) a complete first filling of the prescription; or (ii) a partial filling of the prescription. This is because each of the SKUs are preferably pre-filled to a specific amount. The theoretical balance of the prescription needs to be calculated, based on the initial SKU to dispense, and encoded onto the SmartRx as well, the balance with either: (i) number of refills/repeats, or (ii) completion of a partial filling, or (iii) a combination of both. This balance needs to be communicated to the Mail Order system when the SmartRx is filled.

A proprietary DD printer driver (otherwise referred to as an "Rx printer module") installed on the CMS scans the printout data to determine the nature of the print job. The Rx printer module can be either a peripheral of the CMS, or a shared network printer. A prescription, when detected, invokes the creation of the SmartRx. Otherwise, non-prescription data is passed through to the default specified printer. It should be understood that particular implementations disclosed herein integrate with the CMS such that the CMS and its resources support the operation of the system described herein.

The Rx printer module checks the existence and availability of each medication in the server database. Medications not available in the DD system are passed through to the default specified printer. For each medication in the prescription, the Rx printer module prints a "SmartRx" to the SmartRx card printer with two data components: (i) human readable Rx (printed in black ink) with all data elements required for any pharmacist to dispense the medication; and (ii) machine readable 'token'. This token represents all the prescriptions that have been prescribed by the doctor to the patient. This means that the SmartRx has to be big enough to contain the details of all medications prescribed. This could be up to three (3) prescriptions on the SmartRx, for example.

The Rx printer module also creates a print job on the server, to print any necessary educational materials (e.g., on a local printer) pertaining to the medication (e.g., one page per medication) to a local printer on standard size paper. This printer is a peripheral of the local server, and accessible by the clinic support staff. The doctor signs the SmartRx and gives it to patient. The doctor also counsels the patient about the medication and its usage, telling the patient that they can pick up educational materials specifically about that medication from the staff at the front desk. The doctor also explains that. SmartRx can be used at DD kiosk located nearby and that the staff can assist them should they wish to use it and need assistance. The doctor makes it clear that the SmartRx is also operable to fill the prescription at a traditional pharmacy.

3. Using Kiosk to Dispense Medication

Figure 4:
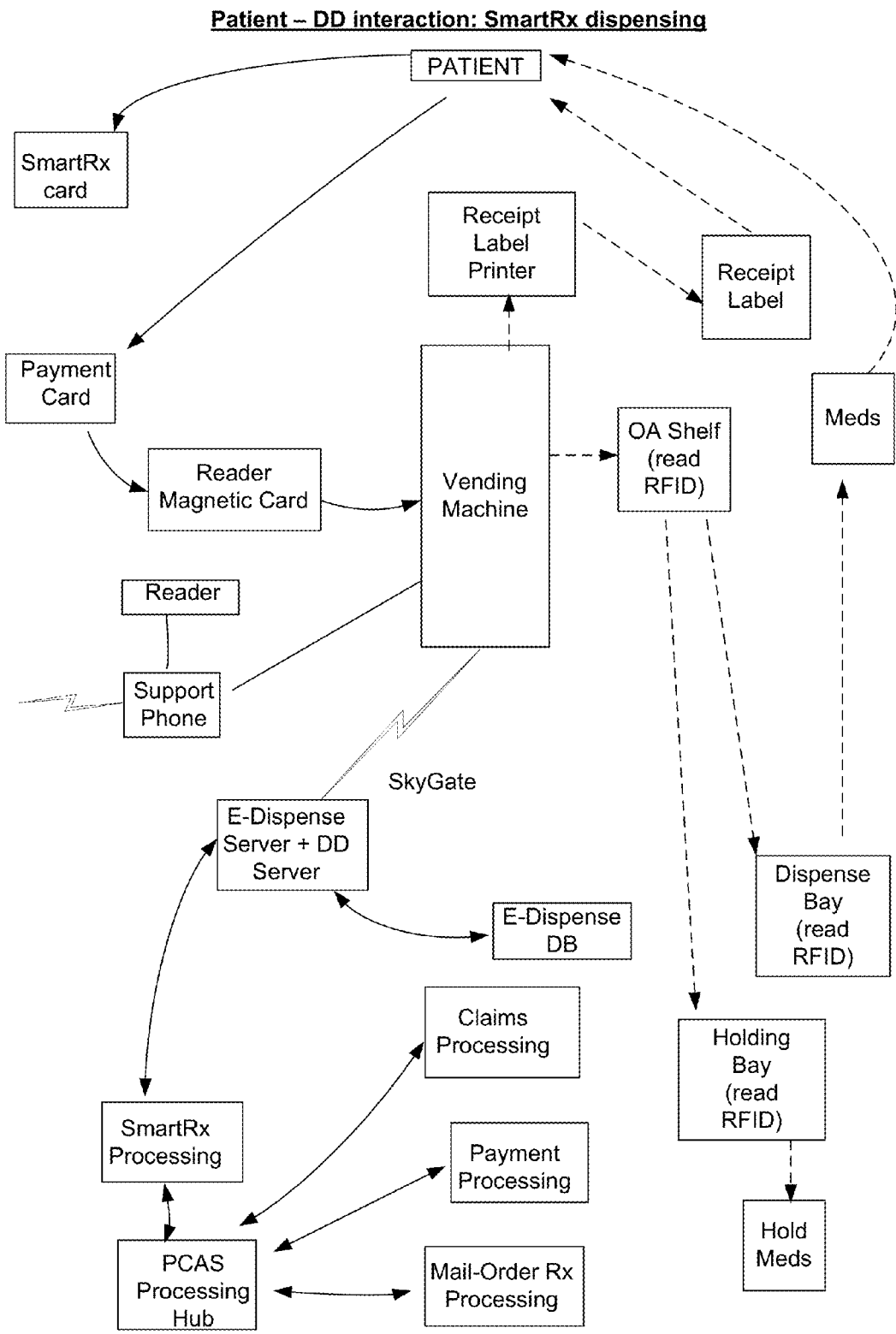
FIG. 4 illustrates the interaction between a patient and a kiosk in accordance with an implementation disclosed herein.
Figure 6:
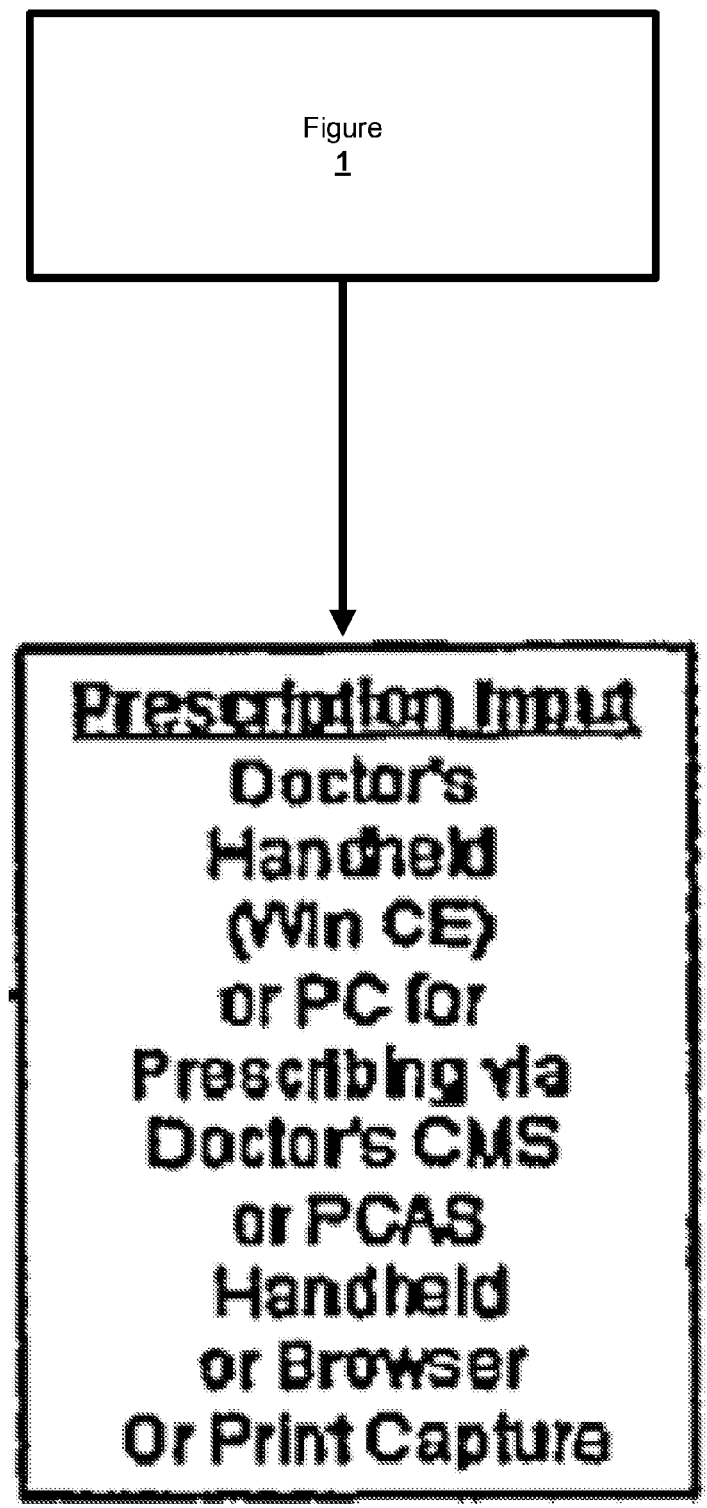

The patient interacts with the kiosk to get their medication, as illustrated in FIG. 4. The prescription is paid for by a drug plan, debit or credit card, or any combination. The patient receives the medication and instructions. It should be understood that the patient may obtain one or more prescriptions per visit.

In particular, a patient takes their SmartRx to a DD kiosk. The kiosk screen prompts for the credit card to begin a transaction. The kiosk features a user interface that is easy to interpret and easy to use. The patient inserts their credit card (for example), and the credit card is read and validated by machine. The patient is prompted to retrieve the credit card, and takes back the card. The kiosk screen prompts the patient to insert the SmartRx next. The patient feeds in SmartRx, and it is read by the machine. At this point the information from the credit/debit card, drug benefits card and the SmartRx have been retained.

The kiosk processes the SmartRx data and displays that it is processing. During processing, the SmartRx data is decrypted and verified to ensure that it has not been tampered with. There is also a check to ensure that the prescription has not been already filled. If it has, then a notification is sent and the SmartRx is rejected. This is operable by virtue of the fact that the data elements associated with the SmartRx include unique data elements.

The DD system interfaces with a server to adjudicate an insurance claim, if any, and determines the amount payable by the patient. The transaction is preferably transacted via a proxy to the server.

The kiosk screen displays the amount payable, and the patient is prompted to accept or cancel the transaction. If the patient accepts the transaction, the DD system interfaces with server to transact the payment. The transaction is completed with the relevant financial institution. This transaction is transacted via a proxy to the server.

The kiosk screen displays that the payment has been approved. The kiosk pushes the relevant medication off of the shelf and onto a "QA Shelf". The DD reads a radio-frequency identification ("RFID") tag on the medication on the "QA Shelf" to confirm that the medication dispensed is the medication on the prescription. The DD confirms that the medication is correct and drops it into a dispensing bay at the bottom of the DD kiosk. The DD then "eats" the SmartRx paper ticket, retaining it in a lock box similar to a cash box. The DD updates inventory to reflect that the particular medication has been dispensed.

Preferably, the DD kiosk also prints a combination prescription label and receipt, an example of which is illustrated in FIG. 5.

The DD then unlocks a dispensary door, and the kiosk screen advises the patient to retrieve the medication. The DD flashes light in (or near) the dispensary bay and makes an audible sound in (or near) the dispensary bay to retrieve the medication. The DD confirms that the medication is dispensed by sensing the RFID from the bottle is gone. The DD locks the dispensary door, and updates the database to reflect successful pickup. The DD advises the patient to affix the label to the medication container. The DD also advises the patient to pick up educational material from the reception desk if they have not already done so.

Note that if the patient leaves the medication or receipt in the DD, within 30 seconds of the medication dropping into the machine bottom, a reminder beep/sound and a reminder to the patient to retrieve the medication is displayed. If the patient does not retrieve the medication, this is repeated, or the DD re-locks the dispensary door and sounds an alarm or otherwise signals for attention from a staff member. The medication is put aside for the patient. The patient is contacted and arrangements made to ensure that medications are provided to the patient.

In the event that a payment is declined by the financial institution, the message "transaction declined" is displayed to the patient. The SmartRx is returned to the user, and a "Declined" receipt is printed.

If the transaction is cancelled by the patient after seeing the amount payable, the message "transaction cancelled" is displayed to the patient, and the SmartRx is returned to the user.

If the patient goes to pickup their educational materials printout but it did not print or it is missing, then a clinic staff member opens an admin interface, selects 'Reprint Education Material by RX#', enters the RX# from SmartRx or from container (if they have already been to machine), and provides the printout to the patient.

If the QA Shelf detects an incorrect container, i.e. the QA shelf reader detects an RFID it was not expecting, then it kicks the container into a holding/reject bin. The message "internal dispensing error" is displayed to the patient, and staff will be notified.

In a particular aspect of the present information, the kiosk disclosed herein is operable to obtain specific and up to date information regarding a particular drug, while maintaining the privacy of the patient.

4. Critical Failure Scenarios

In the event that a medication is placed in a container where the label does not match the medication, this is an error that occurs at either distribution centre or the manufacturer. This cannot be fixed other than having the ability to broadcast a product recall for that medication.

In the event that there is a kiosk stocking error, e.g., the medication was placed on the wrong shelf/row, the RFID reader on the "QA Shelf" will detect this error when the machine attempts to dispense the container. If a CMS medication to DD SKU mapping is incorrect, this is attributable to human error since the mapping table should be created, reviewed, and scrutinized by multiple people. Each machine in the field may have a slightly different mapping of drugs.

There could be data corruption on the RFID tag. Any data errors found should be rejected. The data on the RFID should have a checksum to ensure that this is not the case. A dead RFID will not produce any reading, possibly causing multiple dispensing.

In the event of a kiosk hardware error, e.g., incorrect shelf/row item dispensed, the RFID reader on the "QA Shelf" will detect this error when the machine attempts to dispense the medication container.

If no item gets dispensed (e.g., item gets stuck somewhere in the machine, or an item is dispensed but the RFID is dead or unreadable), then the RFID reader on the "QA Shelf" will detect this error.

If multiple items gets dispensed, the RFID reader on the "QA Shelf" will detect this error, and preferably kick all the items into the reject bin.

If a power failure occurs during a transaction, the DD must cancel the transaction. If a payment has been made but the medication has not been picked up the transaction should be cancelled. If the power failure occurs while the labels are printed, the transaction should be reverted the next time power is restored. If the labels have been printed, the prescription educational material has been printed and the medication is in the hopper at the bottom, then the door should be unlocked to allow the patient to retrieve the medication.

A power failure can occur at any time during a transaction. In this event, notifications are sent immediately to clinic staff and the server if the internet is available. If the transaction has been completed, the funds being debited from the financial institution but before the medication has been retrieved by the patient, then the transaction will be queued to be reversed the next time power to the DD has been restored. The DD will refuse to accept any more transactions until power has been restored. The DD monitors the internal temperature of DD even with the power off. Each medication will have a temperature range that the medication should be stored at. The medication should not be dispensed if the medication has been outside the specified storage temperature range. These and related internal conditions are monitored by operation of the DD and medication that has been stored outside of normal parameters and/or expired will be rejected by the DD for disposal.

5. Technical Considerations

Listed below in Table 1 are the prescription data requirements, as an example.

TABLE 1

SmartRx data storage requirements.

| Requirement | Max size {bytes} |
|---|---|
| medication name | 51 |
| medication ID | 20 |
| dosage | 13 |
| frequency | 13 |
| repeats | 1 |
| quantity | 2 |
| duration | 13 |
| start date | 4 |
| notes | 100 |
| physician name | 51 |
| physician phone number | 10 |
| physician address | 141 |
| patient name | 51 |
| patient phone number | 10 |
| patient age | 2 |
| patient weight | 2 |
| insurance carrier id | 4 |
| drug plan no. | 20 |

The prescription label is designed such that it is easy to match up to the container to which it needs to be affixed. In one particular implementation, a drug name in large lettering is placed at the top of the label, and then the same corresponding drug name in large lettering is placed on the container inside a 'dashed line area' that says AFFIX HERE.

The prescription ID will be unique. It will be defined preferably as: CCCCCDDDYYYYMMDDXXXXX, where: CCCCC is the clinic id; DD is the doctor issuing the prescription; YYYY is the year of issue; MM is the month of issue; DD is the day of issue; XXXXX is the prescription number for the day issued by that doctor.

The receipt must contain all the information that is required for it to be valid for income tax purposes, or to accord with other laws.

The generic drug educational information for use in the DD system could be sourced from different vendors. The educational material preferably should fit on one letter-size sheet of paper. That is, one sheet per medication.

For use with the system, all credit cards or debit cards conform to the physical dimensions as specified by the ISO-I standard size (85×54×0.8 mm) Preferably the processing will be done directly with a bank rather than through third party processing. "Track 1" and "Track 2" shall be read from the cards, and the data passed to the local DD Server in a message bundle for processing, in a manner that is known.

For the debit cards, the keypad needs to be secure. A debit keypad can only be used in circumstances where the transaction can be monitored by a live person. If any tampering is detected, the DD scrubs the transaction. All PIN data must be in volatile memory. It must never be stored or committed to permanent storage.

A SmartRx will contain a prescription ID that identifies the prescription. The drive mechanism for accepting the Smart Rx is essentially the same as that of the credit/debit card. This assumes that the Rx card has the same dimensions as the credit/debit card. If the thickness of the Rx card is out of spec in relation to the debit/credit card, a special reader can be used. To prevent old SmartRx's (such as those used previously at a regular pharmacy) from being used, they will have a discrete lifetime that they are accepted, e.g., one week, or the server and database are configured to track a prescription is filled so that the same prescription is not filled twice.

The DD preferably has one reader, but treated as two logical readers: (i) one for the SmartRx, because the Rx reader needs to be able to return the Rx if the transaction is cancelled and also needs to be able to retain the Rx once the transaction is completed; and (ii) a magnetic strip reader for the payment card (credit/debit). The reader needs to be able to read the magnetic strip on credit cards and be able to read the SmartRx. The reader is required to consume the SmartRx card and place it within an adapted cash box. This cash box shall be exchanged with an empty cash box upon stocking.

The Smart Rx printer will print both a human readable prescription and a machine readable prescription ID. The printer used to print the educational materials for distribution to the patient is preferably a color printer that is a peripheral of the DD server. The receipt/label printer in the kiosk is an impact printer. Replacing the ribbon will be based on the number of prescriptions dispensed. Each time the machine is filled, a test print of the label and receipt printer will be done. This will allow the technician to decide to replace the ribbon immediately or postpone the replacement until a future visit. The ink is black only.

The display will be a 12-17" touch panel display. The touch panel will have a touch panel driver that emulates a mouse. The touch screen portion will connect to the system in the DD cabinet via USB. The touch screen will be supplemented with two buttons that correspond to proceed and cancel. The buttons will be labeled as such in both in English/French, and also possibly in Braille, or other languages.

Each of the DD system units will have an on board sound card. Standard drivers will be used. In order to communicate with the call-centre pharmacist the patient will have to pickup the handset to initiate a call. The software will capture and translate a VOIP connection to the call centre pharmacist. A non-irritating tone is preferably used to convey alerts or to gain the user's attention.

The first keypad, in one particular implementation, has two physical buttons spaced out evenly along the right bottom of the display. A laminate overlay, fitting over the buttons and screen, shall be used for any necessary physical labeling.

Markings on components throughout the system require consistency for easy identification and QA purposes.

A common identifier, used whenever possible, shall be the medication SKU. The digits 0-9 will be assigned a unique color. The color-coded SKU shall preferably be identified on: (i) drug container labels (manufacturing line); (ii) internal packaging (the smaller boxes containing unique SKUs that go inside the larger shipping packaging); (iii) row labels at the front of each shelf inside the kiosk; and (iv) the 'flipper' on the end of each coil inside the kiosk.

Non-color-coded SKU should still be identified where color is not available, such as: (i) the prescription label; and (ii) the receipt label. For the medication containers, there is a need to standardize to a minimal number of container sizes as this affects the shelf and coil design in the kiosk. The ideal container characteristics are based on the tray and spiral combination. These dimensions allow for the product to tilt slightly backwards against the upper edge radius of the coil (2" diameter coil) for perfect dispensing (i.e. no 'crabbing' of the container along the bottom of the shelf):

1. WIDTH: 2.95 inches (~2$^{15}$/₁₆") maximum (required to fit between 3.0-inch sidetracks). Approximately 7.4 cm.

2. DEPTH: 1.35 inches (1$^{11}$/₃₂") maximum allows 12 items per coil (our goal), and 1.5 inches (1½") maximum allows for 10 items per coil if necessary for atypical packaging. Approximately 3.3 cm and 3.7 cm, respectively.

3. HEIGHT: 3.75 inches (1¾") maximum allows a sufficient number of shelves to fit in the machine. Taller containers may be allowed for atypical packaging by giving one shelf (probably the top shelf) more headroom. Upwards of 4.1 inches (4¹/₁₆") is preferable.

4. VOLUME: ideal is approximately 125 ml (cc). The size needs to allow for cotton.

5. SHAPE: ideal is rectangular or oval with slightly rounded bottom (to prevent 'crabbing') with a wide-mouth opening.

6. CAP: cap must be tamper-evident and child-resistant.

7. COLOR: translucent (clear or near-clear).

8. MATERIAL: PET (if clear is a requirement) or HDPE (if opaque is okay and if cost is better).

The pill bottle form factor will be a 125 ml PET clear wide mouth bottle. The dimensions of this bottle are similar to the bottle above with a wide mouth. The RFID tag could be contained on the label that is applied to this bottle when it is filled and packaged. For atypical (non-pill) items such as powders, blister-packed drugs, liquids, inhalers, etc. formed plastic clamshells can be used that have a footprint no larger than those required for the pill containers (WIDTH× DEPTH). HEIGHT may need to be slightly taller.

Patients may need phone access to a pharmacist for customer support. Maintenance personnel also need phone access to the relevant service provider. This is preferably a mobile phone with a telephone booth quality handset. Internal direct-dial (to a fixed number) cell phone inside the machine, e.g., the fixed number is the service provider, which will transfer calls as needed.

In a number of situations, the physical inventory in the kiosk and the electronic inventory (as tracked by an automated inventory tracking means, referred to as "e-Dispense") will need to be reconciled. Foremost, this needs to be done when a kiosk is re-stocked (fulfillment of the purchase order generated by e-Dispense). In the ideal success scenario, the shipment manifest (a.k.a. bill of lading ("BOL")) will be the same as the e-Dispense Purchase Order ("PO") (both physically and electronically). Non-ideal scenarios include: (i) the PO differs from BOL (intentional, e.g., stock unavailable, etc.); (ii) the BOL differs from physical shipment (unintentional); (iii) the BOL matches the physical shipment but shipment is damaged.

When stocking of a kiosk is complete, the e-Dispense inventory database must be reconciled with what is now in the machine. A few different methods are contemplated for implementations in connection:

1. The stocker uses a handset to call the service provider's office and initiates an "Inventory Update" request to modify thee-Dispense inventory to the new numbers.

2. The stocker uses the display and keypad on the kiosk to modify the initial e-Dispense PO (pulled to machine from the DD server) to match the BOL (or rather, the actual new inventory if the shipment was different for some reason), and then commits it to the e-Dispense server.

3. The BOL is encoded into RFID card and included in the shipment. When the kiosk is stocked, the BOL card is inserted. The stocker would still need to be able to modify this in the even that the shipment and BOL differ. This would complicate the shipping process.

4. While stocking, each SKU is "checked-in" to the kiosk by passing it over the QA Shelf (stocker puts machine into 'check in' mode). An interface to manually edit the e-Dispense inventory numbers may be required. The display will not be visible. If the stocker has a PDA then the PDA could connect via network cable/WIFI to the DD server. If the shipment, the BOL and the PO all coincide (the ideal scenario), then the stocker is able to update the e-Dispense inventory database using the display and keypad on the machine.

6. Deployment Considerations

Before a DD kiosk is installed at a clinic/doctor's office, a site survey is preferably conducted to identify what additional changes are required to ensure proper operation. In particular, the survey should identify the following:

1. Are there electrical outlets in the area?
2. Is the quality of the electrical power within spec for the DD Unit?
3. Is there sufficient cooling/ventilation?
4. Is it a reasonably secure location? What is the potential for vandalism or theft?
5. Is it within a reasonable line of site with the administrative area?
6. Is there cell-phone coverage and/or signal at the location?

7. Security

If the SmartRx comprises a prescription ID it may be unnecessary to use additional encryption. All personal information for the patient is stored on a server and will be inaccessible to anyone or any machine that does not have access to the server.

For the kiosk itself, there will be no window in the dispensary. There will be sensors within the machine to indicate that door was opened, and all door open events will be logged. With the lock closed, the circuit is armed. Any disturbance will cause the alarm to trigger. With the lock open the circuit is disarmed, however, if there is any tampering with the inside of the delivery area, a warning will be generated. All warnings and alerts are sent to the server to notify appropriate staff.

Access to the kiosk will be granted in three separate ways:

1. An employee card is assigned a magnetic card that is an encrypted access card. If an employee uses the same employee card at different clinics while at one clinic then a cloned card is in use. This type of usage should be detected and the locking out of both cards would occur.
2. A PIN number provides access, using either the touch screen or keypad.
3. A physical key provides access, similar to other kiosks.

The employee card and the PIN will release the electronic lock, and the physical key will release the physical lock. When the door is open with authorization, the machine enters a maintenance/admin mode which enables extra functionality that is not otherwise available, e.g.: (i) using the embedded cell-phone to call central office; and (ii) using the display and keypad for editing machine parameters and/or initiating communications with the central PCAS server.

If unauthorized access if detected, a small concealable wireless camera will begin recording. There should be source of illumination when the door is opened sufficient to light up the face of an intruder. One option (for streaming video or photos) is to use a wireless system based on 802.11, for example, such that the camera is essentially a peripheral of the local DD server. An 802.11 repeater may be needed. All wireless components should be limited to known MAC addresses and encrypted traffic. Another option (for photos only) is to use a camera tied to the customer support cell phone (no 802.11 required).

It should be understood that the implementations disclosed herein contemplate integration with the CMS system, as described above. Alternatively, implementations disclosed herein is operable to send a message to a CMS system, which is preferably an encrypted electronic message. In response, Implementations disclosed herein preferably received an electronic message that includes encrypted patient information require for processing the prescription.

8. Operational Considerations

Once the medication inventory hits a predetermined low water mark and/or a periodic milestone is achieved, a purchase order ("PO") type message is sent from DD server to the server. This PO tells the serviced provider what medications the kiosk needs. All other pending service requests will be scheduled at the same time to ensure that a service trip is optimized.

When the drugs for a kiosk are packed up at the distribution center, they are packed so that the shipping box has N smaller boxes. Each small box is labeled with the drug and the color coded SKU, and has a Bill of Lading that shall highlight any changes made to the PO issued by e-Dispense.

The kiosk is opened up, and stocked from the packaged order. Every coil is identified with a color-coded SKU. The labeling should be such that the labeling of the coil will match the labeling on the medication packaging and on the medication containers themselves. All new stock is stocked from the back to the front of the DD.

There may be stocking instructions that are issued from the service provider. This could be a request to remove old stock, implement a drug recall of one or more SKUs, or empty the medication reject bin.

When stocking is complete, the inventory in the machine must be reconciled with the inventory database on the server.

For servicing, there is generally a requirement for a pre-determined preventive maintenance schedule. Whenever the machine is serviced, all the normal preventive maintenance checks and servicing should be done.

The used SmartRx lock box has a specified capacity. The number of Rx kept in the lock box is monitored by the kiosk and when the predetermined high water mark is reached, a message is sent to the server requesting that this kiosk be serviced. All other service requests will bill queued at the same time to ensure that the service trip is optimized.

When the lockbox is full or nearly full, the entire lockbox is replaced with an empty one, and the full one is taken away by the service provider. When the lockbox is opened the prescriptions should be audited and confirmed that all prescriptions retained by the kiosk matches the prescriptions audited.

Regardless of capacity of the rejects bin, rejected medications should be collected as soon as possible after being detected (and replacement stock put back in the machine). There should be regular maintenance and top-up of consumables (media & ink) for all printers involved, including the SmartRx card printer, the color printer for the educational materials, and the kiosk label and receipt printer.

Revenue Generation Model

As discussed above, implementations disclosed herein included a robotic based prescription dispensing system designed preferably for a physician's clinic operation. The system dispenses medicine immediately, conveniently, more accurately and at less cost than traditional drug store based dispensing systems.

Conceptually, the implementations disclosed herein operate as follows: a patient is in the examination room with their physician. The doctor has reached his/her diagnosis and is in the process of writing a Prescription using a computer-implemented device, such as a tablet computer. At this moment the prescription interface notifies the doctor and patient of the drug plan coverage allowing the doctor and patient to make the best decision for the medication they need. When the medication is selected, a Drug Utilization Review ("DUR") is automatically conducted to ensure there will be no side effects associated with the medication or interaction with other medications the patient is taking. The prescription along with drug education material is then printed.

The patient then walks to a system unit in the waiting room and inserts the prescription. Within minutes, the machine selects the appropriate pre-packaged medication, scans it for verification, and releases it to the patient. The process is painless when compared with the prospect of patients having to travel to fill a prescription. More importantly, the patient's medical record is updated with the record of the dispensing and the patient now is taking their meds immediately, getting better faster. If this is a maintenance drug, the prescription repeat will be delivered to the patient's door within days before their current prescription ends. This seamless integration with mail order delivery improves the chances that patients will continue to take medication as prescribed because the requirement to go to a pharmacy to renew prescription results notoriously in gaps in drug treatments.

Preferably, a service provider attends to all aspects of dispensing operations. In this regard, Implementations disclosed herein is preferably designed as a "turn key" operation for primary care clinics such that all the physician has to do is write the prescription on the ordering tablet. Everything from the installation of the system to its daily maintenance, payment collections and accounting, health benefit adjudication, and inventory logistics and replenishment is preferably operated by the service provider.

It is known that up to sixty percent of the prescription market is for maintenance drugs. Be it for high blood pressure, high cholesterol, diabetes, depression, etc., patient medication programs require compliance and adherence to prescribed medications in order to maintain good health. Typically, when a patient receives a prescription and goes to a drug store for dispensing, the repeats are captured by the drug store and it is very difficult to redirect the repeats to mail order delivery. However, a system according to implementations disclosed herein effectively capture and divert prescription repeats for maintenance drugs to a home delivery service. In this regard, a service provider will operate a mail-order pharmacy for two purposes: (i) to repackage bulk medications into standard prescription doses for the dispensing system inventory; and (ii) to offer mail order delivery services so that patients will be offered the convenience of home delivery with the service provider retaining this important revenue stream. The mail-order pharmacy and home delivery service is significantly less costly than pharmacy-based operations and takes advantage of the automation prescription drugs for order fulfillment.

Further, it is known that an average physician writes approximately 10,000 prescriptions per year. This corresponds to enormous revenue generated for pharmacies. Implementation disclosed herein are designed to dispense medicine inside physician clinics or directly to patients' home, delivering a more convenient service to patients while capturing a portion of the revenue stream that would otherwise go to pharmacies. Where appropriate, pharmacies can be given access to some or all aspects of the system, for example, in order to facilitate the choice of the patient or other situations where it is desirable for the patient to have the prescription filled by the pharmacy. Either way, however, the dispensing of drugs by doctors enables redirecting of certain revenue to doctors which in turns relieves pressure on the health care system and enables doctors to take the time required to cover drug related issues such as interactions more exhaustively and using better tools than what is currently possible under the existing system. The doctor is the entry point for patients to a drug therapy regime, yet the pharmacies have the tools, information and time to cover important health related aspects thereof. The medical details of a drug therapy regime are in the current system not fully passed on from doctor to pharmacists, which results in many cases in a loss of efficacy in the therapeutic effect, inefficiencies, miscommunication, the need for pharmacists to follow up, inconsistent instructions and so on. Implementation disclosed herein enable doctors to be given with better tools to manage drug treatments resulting in a more seamless healthcare system and better healthcare for patients.

It is also known that physicians routinely prescribe on average only 16-18 drugs for their patients. Implementation disclosed herein are designed to service a physician's prescribing routine and cover a majority of their particular dispensing requirements.

Primary care physicians and related secondary healthcare services are increasingly organized in medical buildings that are designed specifically to address the multi-faceted needs of a divergent patient population. However, the most underinvested sector of healthcare for communications and information technology (CIT) is the primary care physician's office. The reason for this is that for the doctor CIT has not offered sufficient tangible benefits to make the investment worthwhile. Furthermore many doctors' offices do not attain the scale of organization to make a significant CIT investment a priority or justify the staff required to support CIT operations. This technology investment can be leveraged to improve healthcare with the doctor's office as the point of contact, e.g., by delivering multimedia information on medical treatments, accessing rich content from databases, mining prescription information based on up to date information regarding drug interactions etc.

Implementations disclosed herein address the foregoing in the following ways:

1. Implementations disclosed herein are delivered as a turn key solution with no up-front investment required by the physician.

2. Implementations disclosed herein offer an incremental revenue stream that provides sufficient incentive for the physician to adopt the technologies.

3. Implementations disclosed herein aggregate physician practices to the scale required to generate appropriate returns on CIT investment.

4. Implementations disclosed herein deliver the organizational ability to make a CIT investment mutually beneficial for the physicians and the patients.

5. All CIT support functions are operated by a service provider eliminating any impact on physician or clinic operations and overhead. Implementations disclosed herein also addresses accuracy and efficiency issues common with pharmacy-based dispensing. Currently, prescriptions written in Canada are paper-based. This 5 results in up to 10% of prescriptions requiring the physician to be called by the pharmacy because of they are not legible. Furthermore, studies have documented that adverse events associated with prescription errors, some resulting in patient death. Implementations disclosed herein addresses these problems, ensuring more secure and accurate fulfillment of prescriptions.

Figure 9:
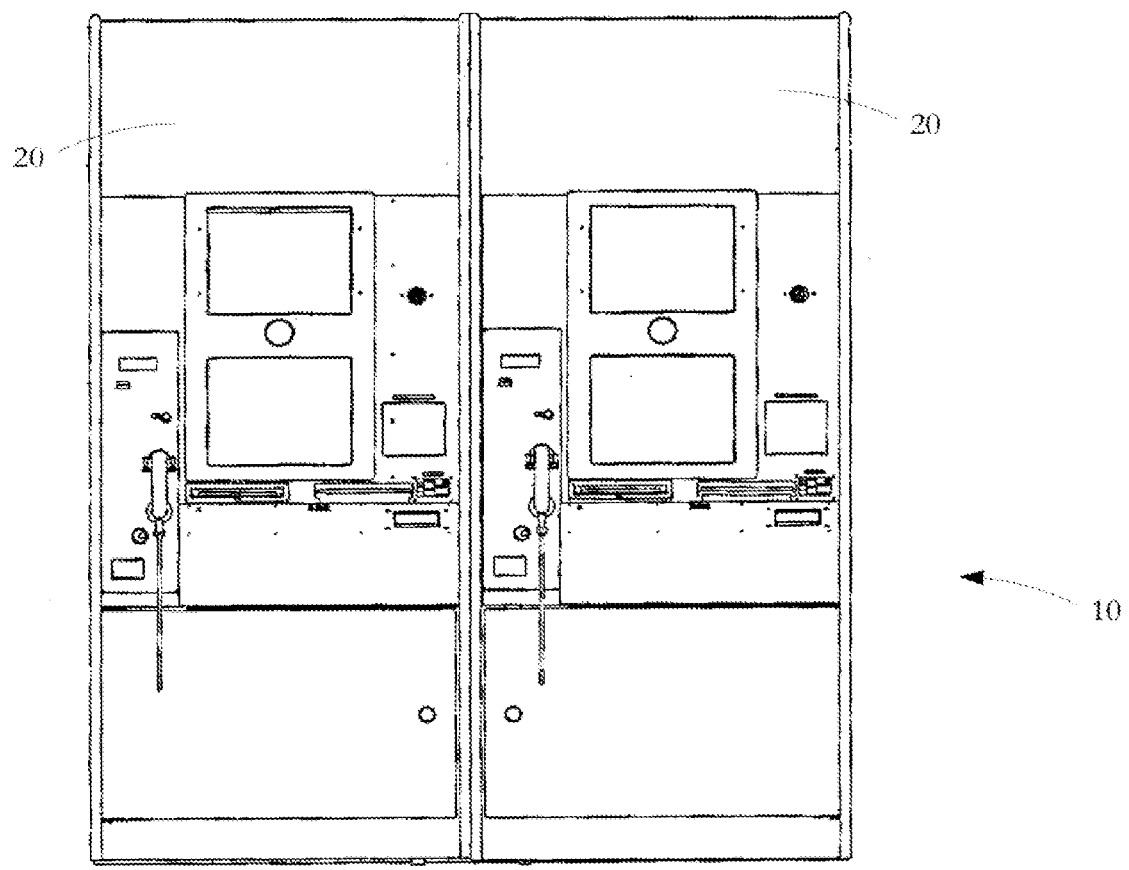
FIG. 9 illustrates a front view of an embodiment of the automated apparatus for dispensing prescribed drugs in accordance an implementation disclosed herein, wherein two, side-by-side front end user-interface modules are shown.
Figure 11A:
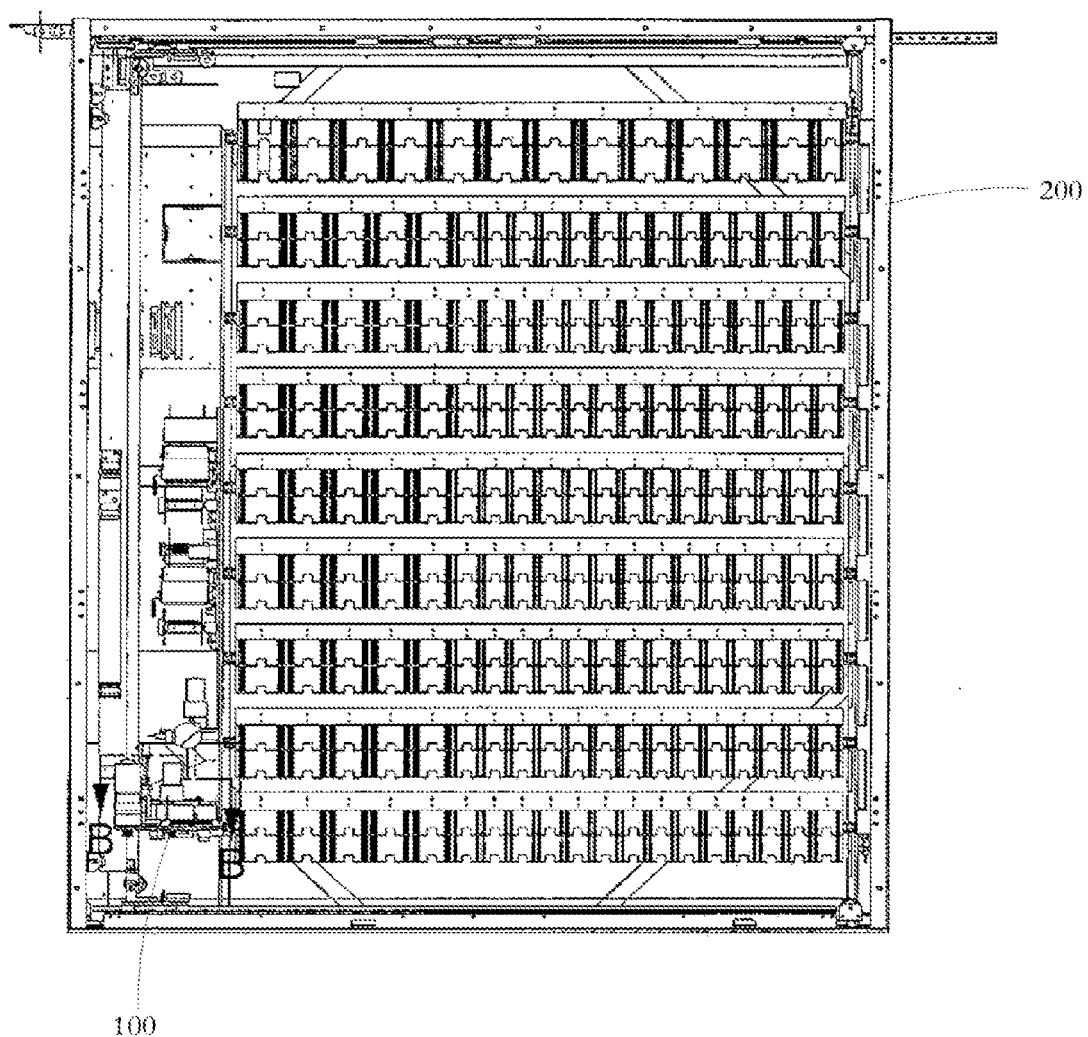
Figure 14:
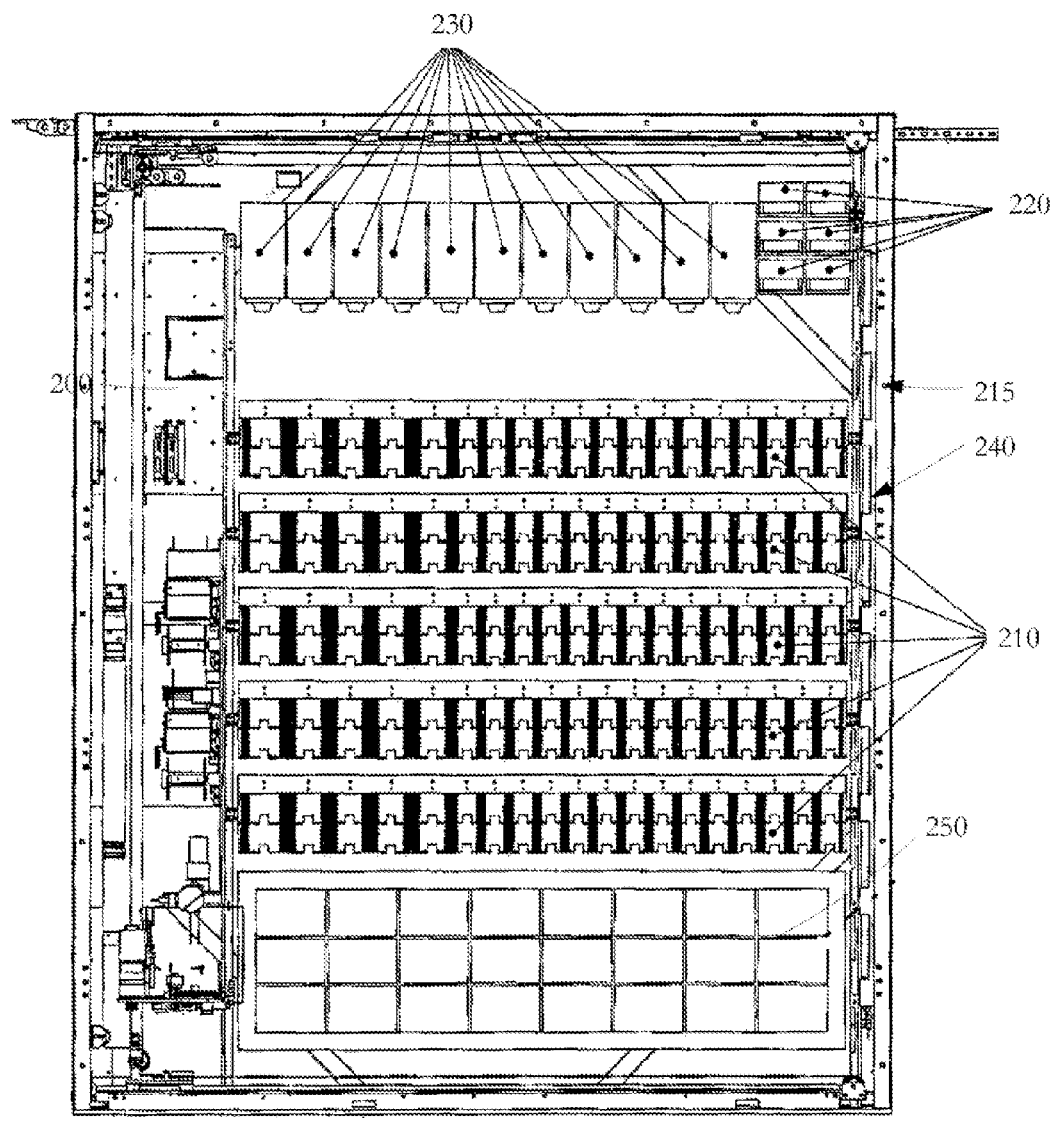
FIG. 14 illustrates a side sectional view of an example of a back end drug vault module of the automated apparatus implementation disclosed herein, with a controlled room temperature top section and a controlled refrigerated bottom section.
Figure 17A:
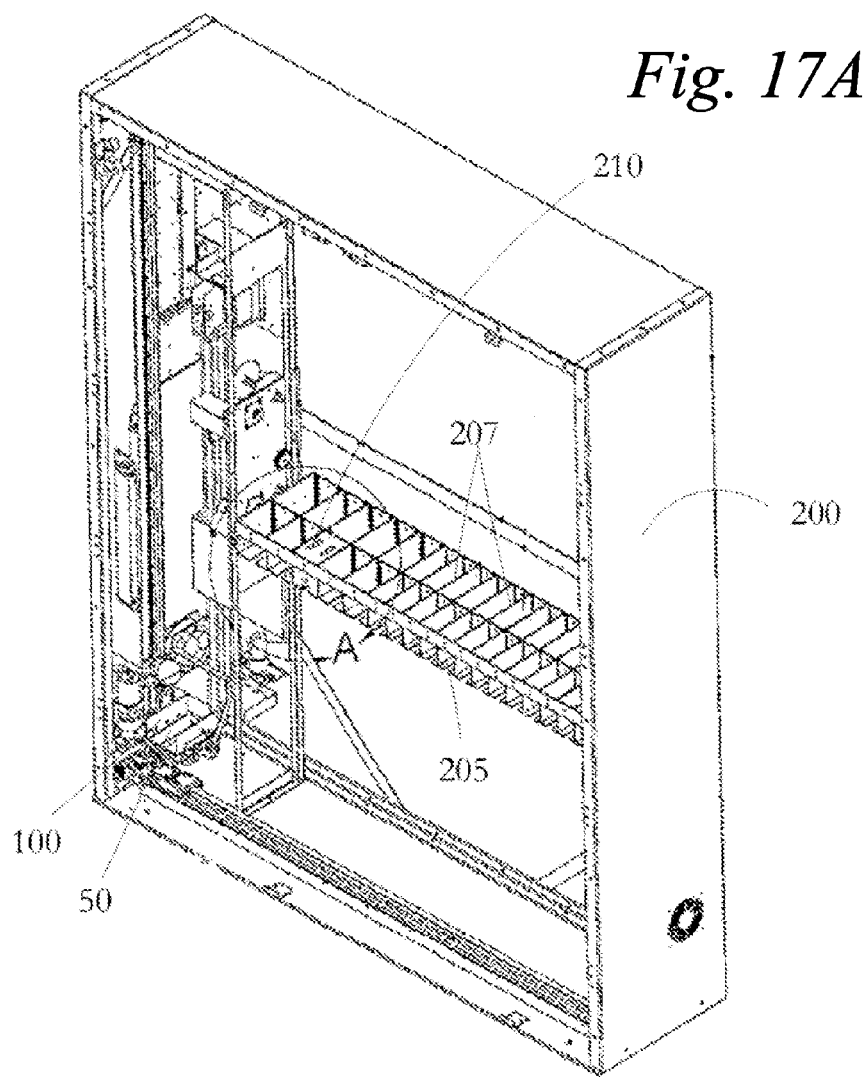
Figure 17B:
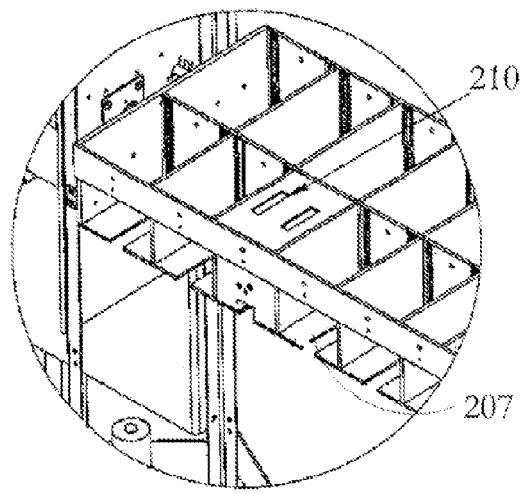
Figure 24:
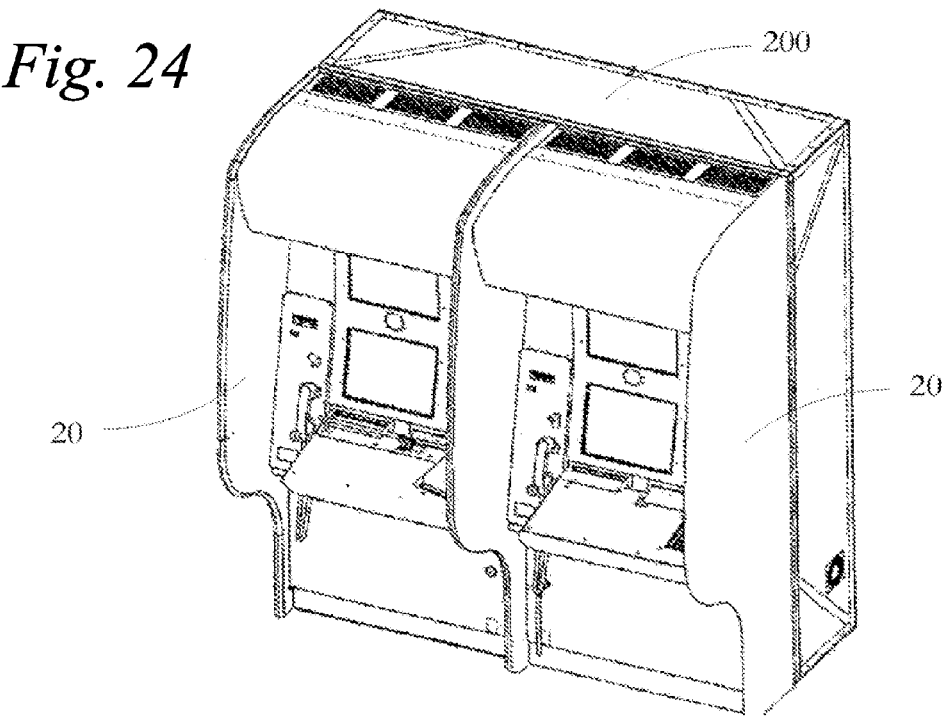
FIG. 24 illustrates a perspective view of an implementation disclosed herein of the automated apparatus for dispensing medicament, wherein two, side-by-side front end user-interface modules share one back end drug vault module.
Figure 25:
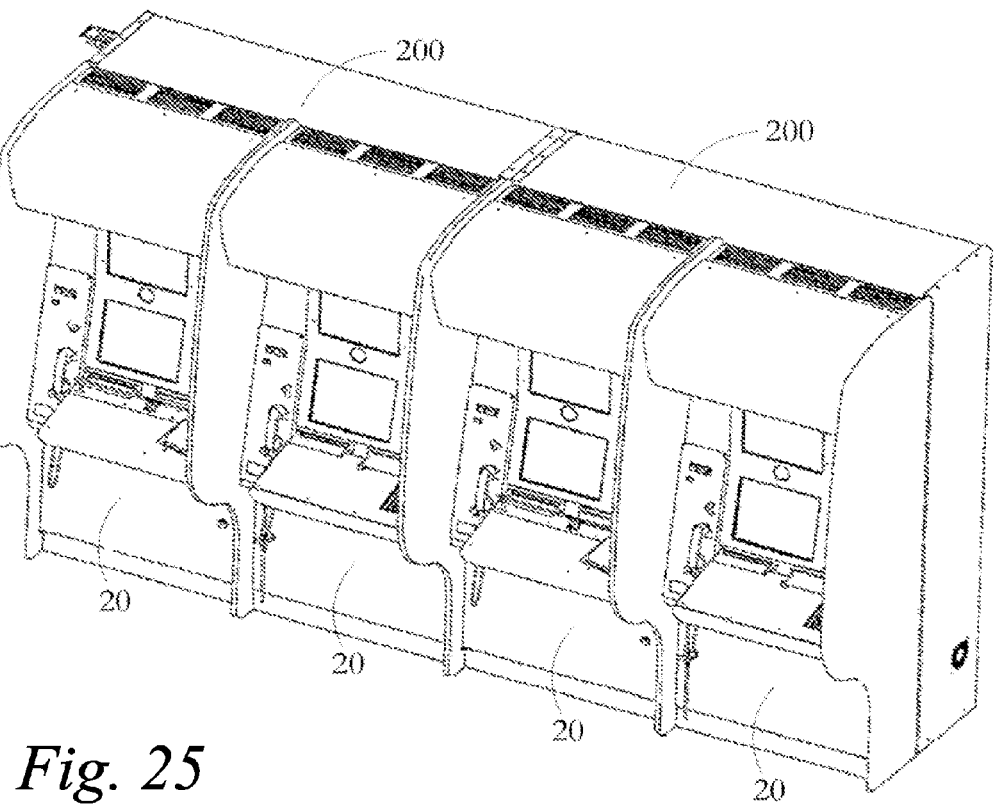
FIG. 25 illustrates a perspective view of another implementation disclosed herein of the automated apparatus for dispensing medicaments, comprising four, side-by-side front end user-interface modules and two back end drug vault modules, whereby each of two side-by-side front end modules share one back end drug vault module.
Figure 27B:
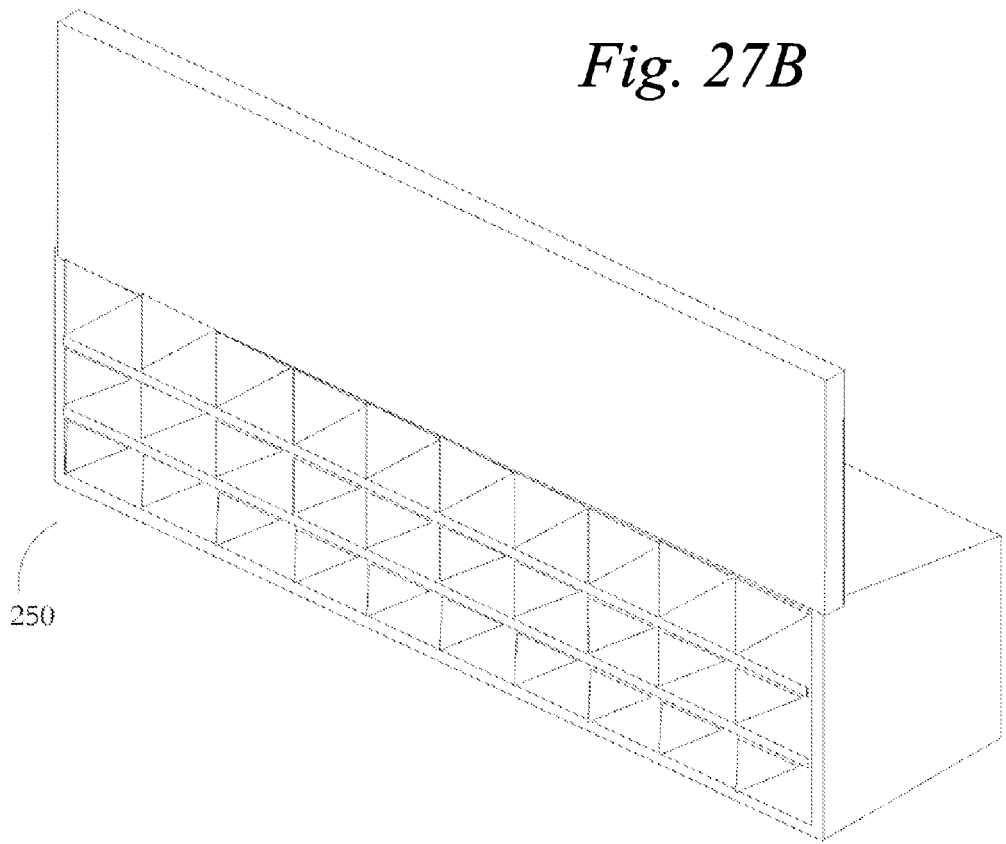
FIG. 27B illustrates a pictorial view of this exemplary module.
Figure 28:
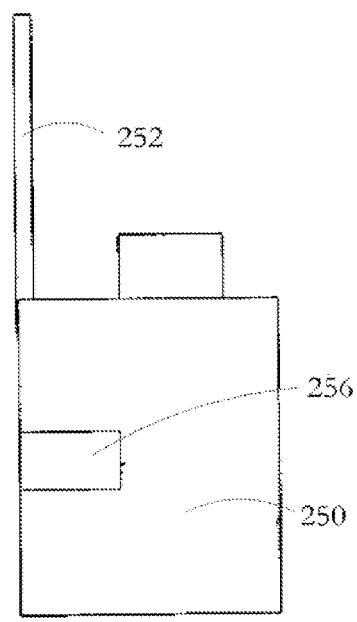
FIG. 28 illustrates a side view of the module of FIG. 25A.
Figure 29:
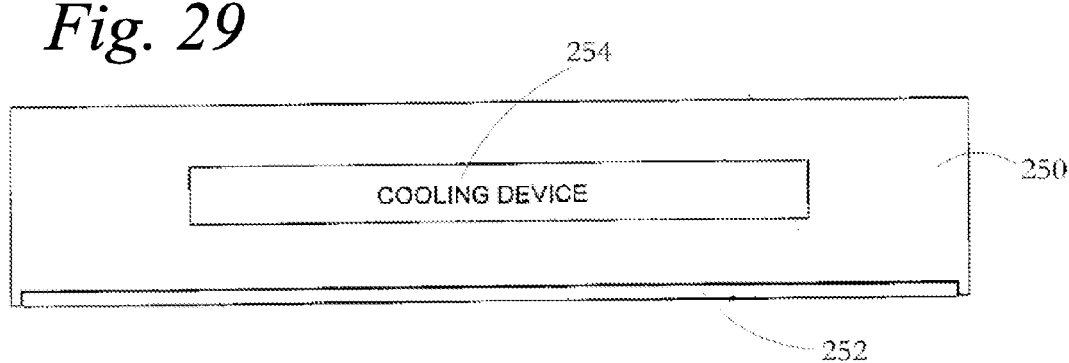
FIG. 29 illustrates a top view of the module of FIG. 25A.

Implementation disclosed herein provide an automated apparatus for dispensing medicaments which advantageously provides improved utility to expand the variety of medicaments that can be stored, prepared and dispensed. Its utility is enhanced by increasing the prescription coverage ratio offered a patient at an autonomous network device or drug dispensary apparatus. This utility of service provided by the apparatus may be viewed from the perspective of a patient (i.e. user) standing at the doctor's office with a prescription in hand and needing immediate medication. The distance the patient must travel and the frictions the patient must overcome to get the medication is the patient's utility function. Utility from the perspective of the drug dispensary, be it a pharmacy or a remote dispensary apparatus as provided by implementations disclosed herein, means how many items on the patient's prescription could be filled, not requiring secondary actions, such as ordering the medication requiring the patient to return for pick up, or delivering the medication to the patient at a later time. Thus, for both the drug dispensary and the patient, maximum utility is determined by the ability to dispense all medications required, on the spot, at the time of the initial interaction. Advantageously, the dispensary apparatus 10 of an implementation disclosed herein is constructed from a preselected number and functional type of modular components, hereinafter referred to generally as modules. These modules include a front end user-interface module (see FIG. 9 which illustrates two such modules located side-by-side), a back end drug vault module 200 in which drug product for dispensing is stored, and a control system 100 (see FIGS. 11A-11C) which is located for operation with both the front end and back end modules. These modules are dimensionally compatible for assembly in numerous combinations, as desired for a particular application, and their internal components are sized and shaped to conform to a grid configuration to enable such compatibility and interconnectability, such that numerous combinations of modules can be assembled and interchanged as desired. This allows an unlimited number of combinations to be configured from an inventory of interchangeable, compatible modules and allows the apparatus to accommodate a wide variety of requirements for a given application. The front end user-interface module 20 is provided both as a half size and full size module allowing, for example, one large and two small user front ends to be attached to a back end module 200, or two, three or four front end modules to be attached to two back end modules. Within the back end module 200, several optional configurations may be assembled to accommodate product inventory as desired. For example, within a back end module 200 any combination of product storage modules may be selected. A controlled room temperature section 240 may be included together with a refrigerated temperature storage section 250, as shown in FIG. 14. Multiple storage container racks 205 may hold any combination of product storage modules, as shown by FIG. 14, including product storage containers 210 for pre-packaged product, bulk medication storage containers 220 for liquid product and bulk medication storage containers 230 for pill/capsule product. If desired, a reconstitution, mixing and/or compounding bulk medication storage container 370, 380, 390 can be added in place of a refrigerated storage module 250 or assembled into a second back end module 200. The modularity of the components of the apparatus is defined in standardized manner to dictate dimensions, key contact points, power, network configuration points and mechanical features, to ensure interoperability for all components and their associated software, hardware and operational parameters. The front end user-interface module 20 is independent from the back end drug vault module 200, whereby they may be co-located in a single chassis as a unified apparatus, or located in appropriate multiples to meet a particular service location requirement. Most commonly, multiple front end modules 20 are co-located with a single back end module 200 and both front ends (or multiple front ends) are serviced by a single control system 100 and back end drug vault 200. This is shown by FIGS. 24-25, in which FIG. 24 shows two, side-by-side front end user-interface modules share one back end drug vault module and FIG. 25 shows four, side-by-side front end user-interface modules and two back end drug vault modules, whereby each of two side-by-side front end modules share one back end drug vault module. Multiple back ends can also be linked to extend storage capacity to serve a front end user-interface cluster.

FIG. 26 illustrates a sub-assembly of two inter-connected back end drug vault modules. A further configuration, which may be desirable to service remote communities with low transactional volumes and long times between inventory replenishment, is multiple back end modules 200 serving a single front end module 20. The control system 100 is improved to, inter alia, provide dispensing reliability of prepackaged drugs which have a range of sizes, shapes, weight and weight distribution (e.g., a heavy dense glass vial on one side and a light weight dropper on the other side of a package renders an uneven weight distribution for the package), slipperiness of packaging, tabs, stickiness, moisture (e.g., from absorption by cardboard), all of which create a plurality of handling problems for robotic systems. Also, drug companies frequently change packaging, so control algorithms may become ineffective when a package change alters an SKU (Stock Keeping Unit) which may be used by the robot to identify the package. Therefore, a robotic control algorithm that prescribes a handling method based on pre-recorded product package information (weight, size, etc) is subject to errors, simply because the packaging was not intended for automated dispensary, and there are currently more than four thousand package variants for common medications, that vary by region, manufacturer, repackager, or distributor.

Figure 10:
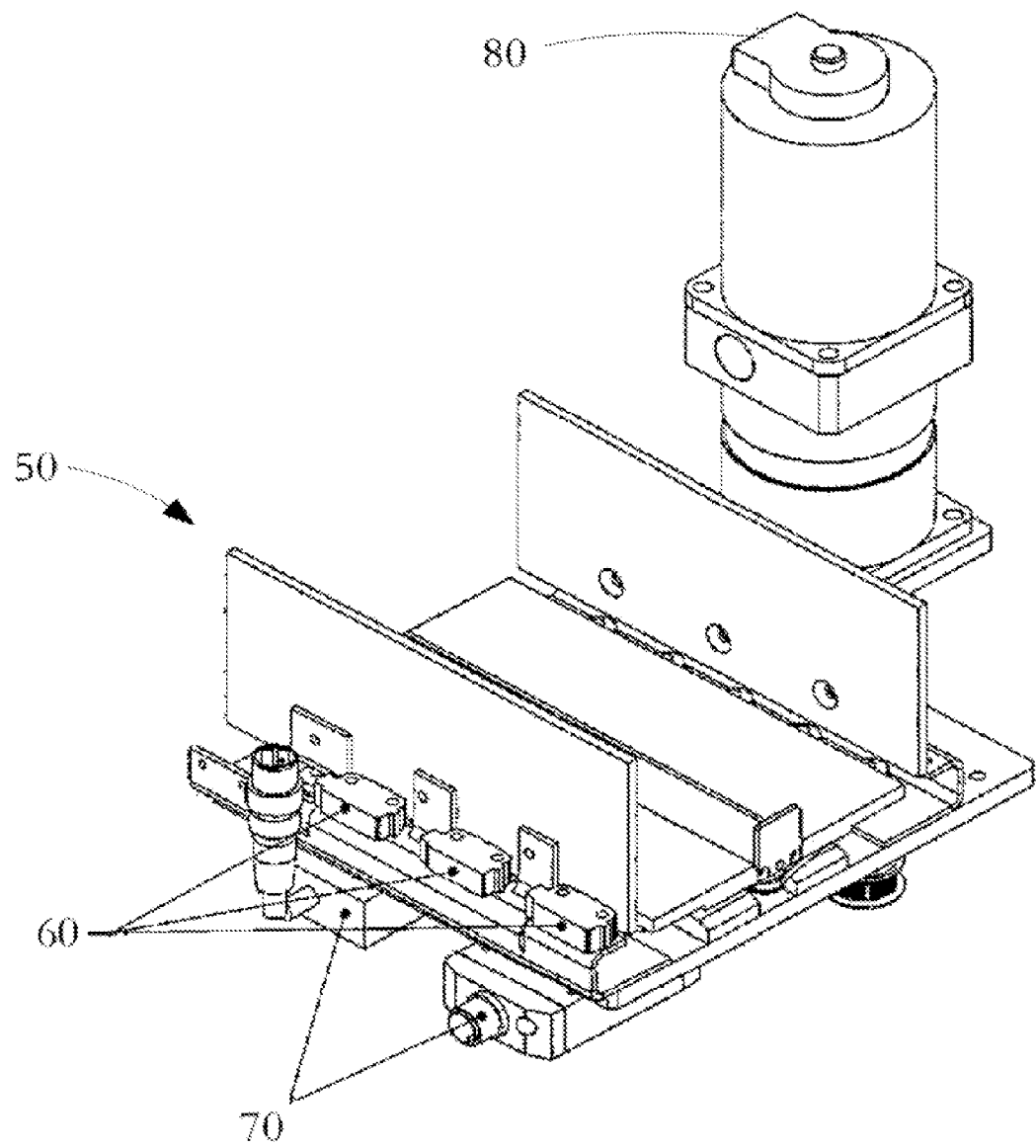
FIG. 10 illustrates an example of a z-axis pick head assembly of an automated apparatus implementation disclosed herein, with product position and z-axis positional sensors used for determining the machine state of the apparatus.

To try to deal with this problem, some known systems create uniform over packaging to assist in robotic dispensary reliability, but this adds additional handling and expense to the dispensary process, a significant increase in the opportunity for error, and additional waste stream burden to products already notorious for over packaging. The control system 100 overcomes the foregoing problems of the prior art by using a "state based machine" based on controls, behaviors and sensors on the robotic pick head 50 (see FIG. 10). Current medicament packaging is generally designed for handling by personnel, not automated machines or robotic machines.

Figure 12:
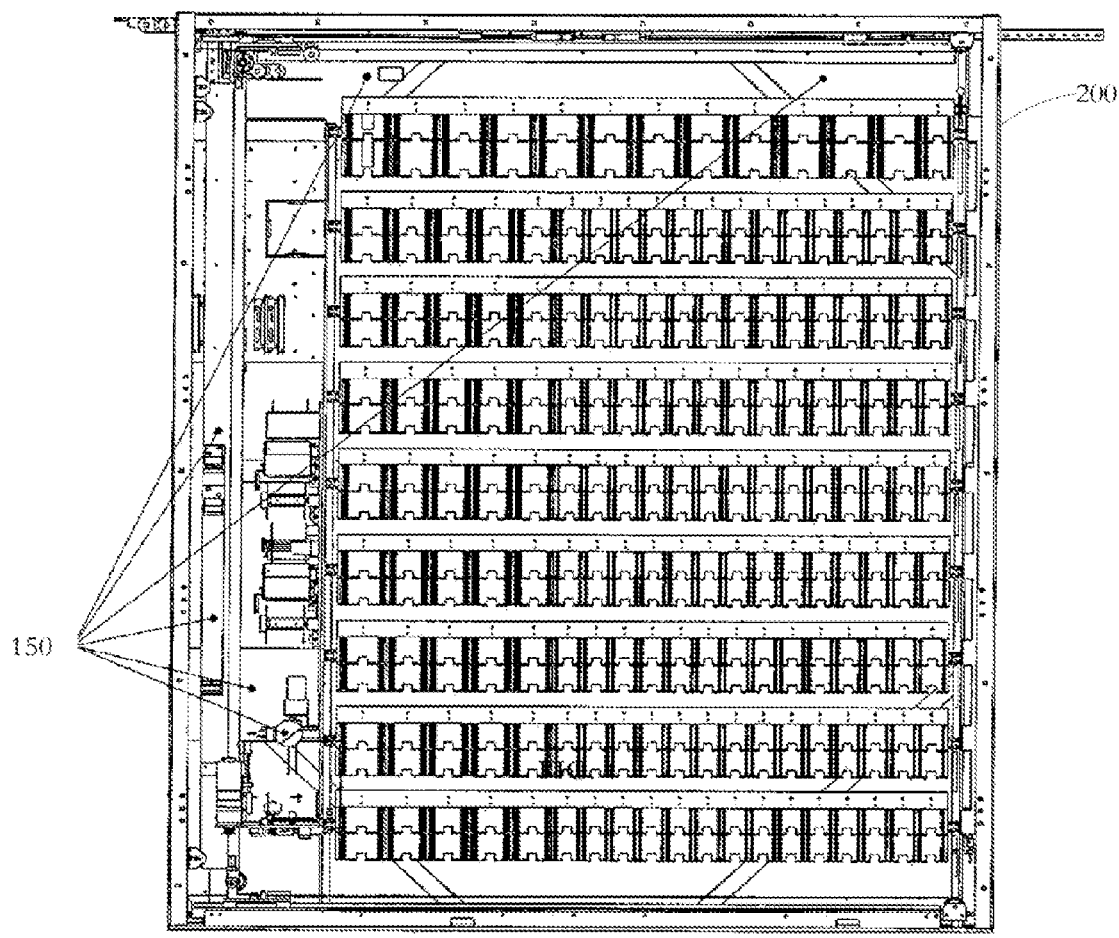
FIG. 12 illustrates a side sectional view of an example of an internal configuration of a back end drug vault module of the automated apparatus implementation disclosed herein, with multiple, networked cameras shown at pre-determined locations within the apparatus.

Humans can compensate instantly and intuitively to variations, changes and anomalies. Machines such as robotic dispensaries are not smart, and require a refined set of behaviors to compensate for common anomalies. As shown in FIG. 12, several networked video cameras 150 are installed inside the apparatus 10 to view what is taking place in the apparatus, and this visual information is used by the control system 100 as well as remotely, if needed, by a human agent. To compensate for the fact that machines, unlike humans, do not intuitively compensate for gripping items, the control system 100 is computer-controlled by a state machine (being firmware), associated software and a z-axis encoder 80 (for positional feedback control) to react to what happens and read the values of the various sensors, which include product position sensors 60 and z-axis positional sensors 70. For example, if a drug product being picked from inventory by the control system 100 is fully registered to be positioned at the back of a platen of the pick head assembly 50, then the control system 100 knows that pick was a successful pick and a tractor of the assembly can then feed it off correctly. A computer of the control system 100 knows the length of products so the module determines from the sensors 60, 70, being simple light beam sensors, where a product should be located. The array of sensors 60, 70 enables the control system 100 to determine what state it is in at any given moment. The control system 100 operates, for example, to pick a product out of the back end drug vault module 200, by using "state tables" of approximately 385 states, each state functioning as a rule.

Intelligence is provided to the dispensary apparatus 10 to solve problems, this being achieved by pick head sensors 60, 70, product information, machine states, behaviors and behavior results. A state determination is made from sensors and product knowledge, determination of a state leads to a selection of behaviors, behaviors are executed in order of success and success of behaviors for particular states increases the intelligence (knowledge learned) of the apparatus and system. The hardware of the control system 100 operates at a first layer of control, while the state machine operates at second layer. The hardware includes a set of behaviors, including jiggle pick, shelf recovery, and others. The state machine drives which of the behaviors the robot is to apply and a series of states are provided with a score. The states know whether one state is better than another. For example, an optimal state would be registered where a product is located at the correct identifier number with the sensors identifying it to be fully registered at the back of pick head measured against product specific information out of the system's database. At the time of a product pick by the control system 100, the product is known because it was measured and its length was recorded when the product was serialized and put into inventory in the apparatus. Also known by the control system 100 is the size, the weight, the shape, the moment arm, and other particulars pertaining to the location of the product to be picked.

The software driving robot knows what it is supposed to expect and the robot deduces what states should occur in order to be successful. It also deduces when it gets into a state relative to what the product is and by combining the product information and sensor information it deduces what to do next to be successful. The control system 100 is controlled to do anything it can deduce to be successful.

A neural network is used by the system and each networked control system 100 to allow it to learn from previous actions and results. State transitions may provide learning knowledge to the control system 100. For example, if the robot achieved a particular state and used a particular behavior to get to that state, this is learned knowledge which is maintained by the control system 100 for future use. A collection of 25 different behaviors is applied by the robotic. If the robot is in a similar state as it was previously, and it previously tried a behavior which did not succeed, then it will not try the same behavior and, instead, will try another behavior. The control system is controlled to apply behaviors on the basis of risk levels, to become progressively more aggressive to achieve success. In a state table, the states reflect this progression for control of the robot so that, for example, it will attempt 1 for, say, shift recovery, then attempt 2 for aggressive shift recovery, and then attempt 3 for maximum shift recovery. The control system 100 is also controlled to do anything in its power to get unstuck, so it doesn't jam (since the apparatus is unattended). The primary rule applied by the robot is that it must not jam. For the robot, to not a make an error is a lesser rule (having lower priority) because the robot has access to a waste container 115 and a waste arm 110 which it uses to direct damaged product. If the control system 100 detects an error it transfers the product to the waste container. The robot applies is hardware, then state machine behaviors to achieve its primary directive of no jamming. If after three attempts to pick a product it is not successful, it reverts to remote control mode by invoking a call center screen for a human agent who is alerted that an error occurred and manual recovery is required. The human agent can look at the screen through the network and can summon a technical person to commence a remote control application over the network which pilots the robot in real time, enabling the robot to service a user who is standing at the apparatus 10.

The control software of the control system 100 acts to try to correct errors when they occur. The robot picks a product from its storage location by bringing the pick head 50 to the storage location slot 207. The slot 207 has a gap in front to allow the pick head 50 to insert a tongue into the slot under the product. The pick head 50 has multiple belts (or wheels or fingers) to pull the product forward as the pick head moves up and onto a shelf of a storage container rack 205 while lifting the product up. This action picks up the first product on the storage shelf location, separating it from the remaining inventory, which is to (ideally) remain on the shelf. The pick head 50 then senses the size, shape, weight of the product it has picked to determine that it has picked a single product unit and determine that it has overcome three common errors, namely, a stuck pick (where the product sits in place due to slipperiness), double pick (where two products are either in close proximity, tangled together or stuck together) and multi pick (usually due to labels sticking together). The state machine, using sensors and a tables of information about the inventory product being dispensed, determines the error based on the physical parameters of dimension and weight and, for product containing RFID (Radio Frequency Identification) tags, by scanning and detecting the presence of more than one RFID tag, or more that one bar code if bar codes are presented in such a configuration as to make them visible. Based on the foregoing information, the control system 100 determines with a high degree of accuracy whether the product is present, whether an error exists and, if so, the state of the error. Upon occurrence of an error, using the error state information the robot implements an escalating series of interventions in an attempt to resolve the error. If no product is present in the pick head 50 and the robot knows there is product in the slot 20, then machine state is a stuck pick. In this state, the robot implements a first level stuck pick resolution action called "Jiggle Pick", for which a software control loop causes the robot to oscillate up and down within a range of motion and velocity determined to be appropriate for level one resolution range. With "Jiggle Pick", distance is important for effectiveness and to minimize damage to the robot, storage shelf and product. Sensors on the pick head determine penetration into the shelf and maintain a safe distance from the surfaces to minimize the possibility of contact damage. "Jiggle Pick" causes the stuck product to unstick from the shelf, in much the same way that a vibratory conveyer overcomes friction to move goods.

Two products may stick together causing two products to be loaded into the pick head rather than one product. In the storage bin, the mean angle between the panels of each product box is shallow and this may cause two package boxes to mate when sitting next to each other with pressure or if cardboard and subject to humid conditions. This increases the chance that when the pick head lifts one box, it may actually lift both, creating a double pick error. To resolve this, an escalation to a level two remedial action is implemented by the local control software creating a shift higher on the control head, to alter the angle the product is held at, thereby reducing the contact area between the first and second product, to create a separation angle, and create the contact point that disallows mating, therefore only pick one box. A third common pick problem is multi pick, where several products are stuck together, typically due to the label or label glue affixing several packages together. The sensors and machine operating software are able to determine a multi pick error based on weight, moment arm of the load, dimensions of the load and load behavior measured by parameters of acceleration and deceleration lag. If the multi pick error cannot be resolved by the foregoing resolution one or two, the local operating software escalates to resolution three, whereby an edge of a pick bin is used as a guillotine to wipe the redundant products from the picked product. As the wiped product may have been damaged or compromised by a level three intervention wiping action, any wiped product is placed in the waste container 115 and is not dispensed without prior confirmation of integrity.

A drug dispensary apparatus must be reliable, measured primarily in terms of availability for service. The ideal machine would be one that never fails, but the very nature of integrated communications, software and hardware, and variety of products and packaging that must be handled, invariably lead to an error rate greater than zero. However, errors are probable and, therefore, error management, isolation and recovery are paramount to prevent failure. A core reliability algorithm used by the apparatus 10 of an implementation disclosed herein is defined in terms of absolute parameters or edicts. Each edict overrides subordinate edicts, with edict one overriding all others. The edicts are the following:

Edict One: Patient Safety—No activity can compromise patient safety.

Edict Two: Protection of Assets—No activity can compromise in order, the security of the drug inventory or the security of the machine.

Edict Three: Maintain Operability.

Edict One is described in detail in the PCT Application. Edict Two requires escalating procedures that do not require the machine or the drug vault to be opened. Edict Three requires that the escalating procedures be as succinct as possible to maintain an in service status and core utility of the apparatus. The dispensary apparatus 10 is networked to a computer system so that any error occurring at the apparatus with respect to product (SKU) becomes a shared network experience and part of a common error record contributing to the accumulated knowledgebase of the system. Error parameters forming trends can be analyzed, such as, errors common to a specific machine, or specific machine configurations, or specific conditions, or specific packaging or product variants. As components of a neural network, each software controlled robot has pre-programmed autonomous actions, and being a state machine is able to adapt to changes to deliver the desired result under the control of a strictly applied rule As stated, the robot's state machine in effect learns to recognize conditions and acquires knowledge in the form of a recorded history of the result of various solutions, thereby adding to the collective operation knowledgebase, to allow the robots of each of the networked dispensary apparatus 10 to learn from a successful outcome. For example, a product jam that entraps the pick head is a common reason for a dispensary apparatus to be out of service. The robot has a set of procedures to unstick itself. It knows its slot location and it knows the product SKU on the platen, but it may find that its X and Y axis movements are arrested.

If the database has no prior occurrence of this specific problem, the software begins the following resolution sequence, starting with the least destructive behavior: jiggle gently, yes/no resolution; escalate to jiggle intensely, yes/no resolution; escalate to jiggle intensely while pulling back the platen, reversing the pickup belts and while applying X axis up, to force the product free, sacrificing the product to the discard bid (this action will discard one product SKU), yes/no resolution; escalate to ramming the platen forward into the slot and elevating the contents of the slot, then dropping them into the waste container (this action will discard all remaining product SKU's in the slot, but if successful, frees the robot to pick and dispense from the remaining slots), yes/no resolution; revert to shut down, call for help center technical intervention, open a remote pilot session, whereby the multiple cameras within the apparatus allow a technician at a remote repair center location to see inside the apparatus and to take over remote piloting of the robot to resolve the issue (this action avoids on site intervention and the apparatus is not opened so no security issues arise with this intervention), yes/no resolution; escalate to local call out whereby a qualified local technician who is certified to enter security level one (front of machine) is dispatched to the site, opens the front of the machine and can repair the problem if it is external to the drug vault, yes/no resolution; lastly, escalate to truck roll whereby a senior technician is called out, and the senior technician is authorized to security level two (drug vault access) and can resolve the issue by opening the back end drug vault module(s).

Figure 13A:
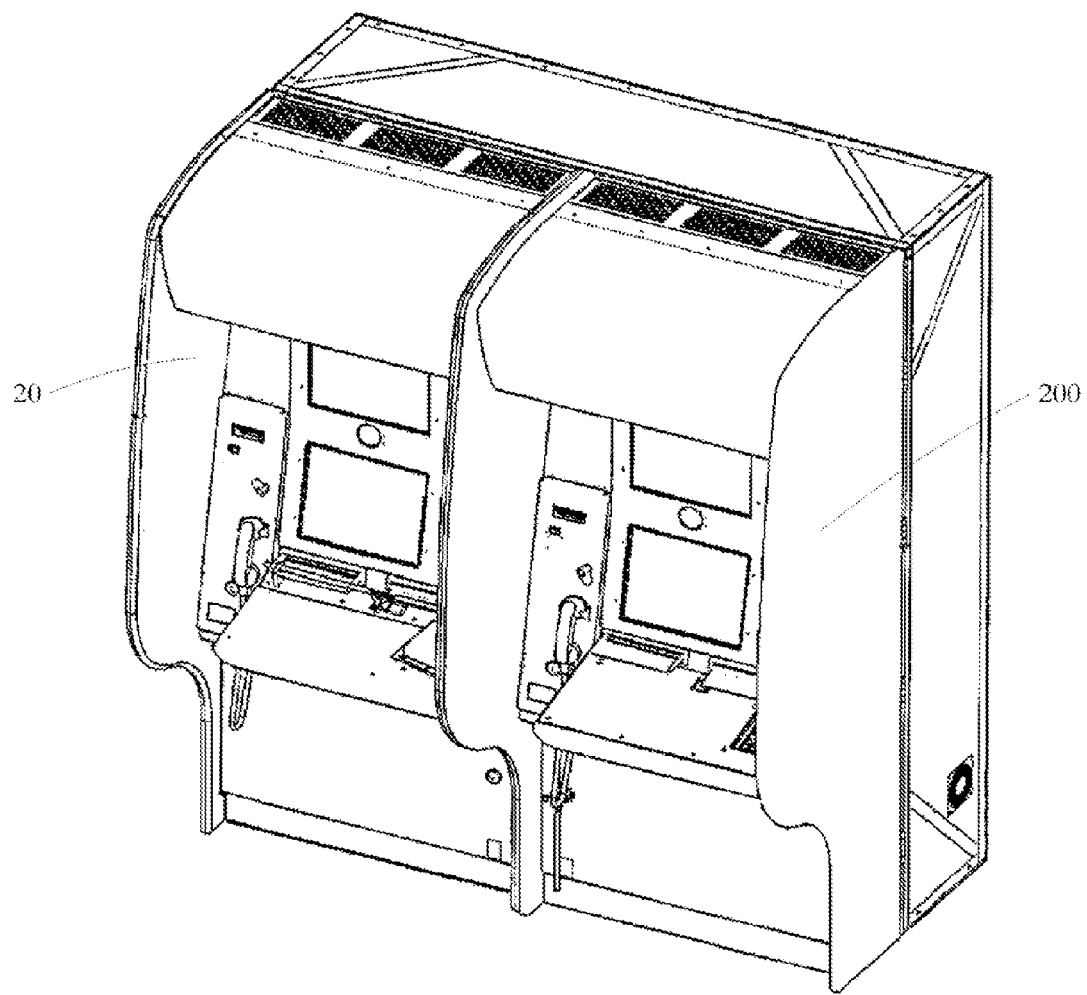
Figure 13C:
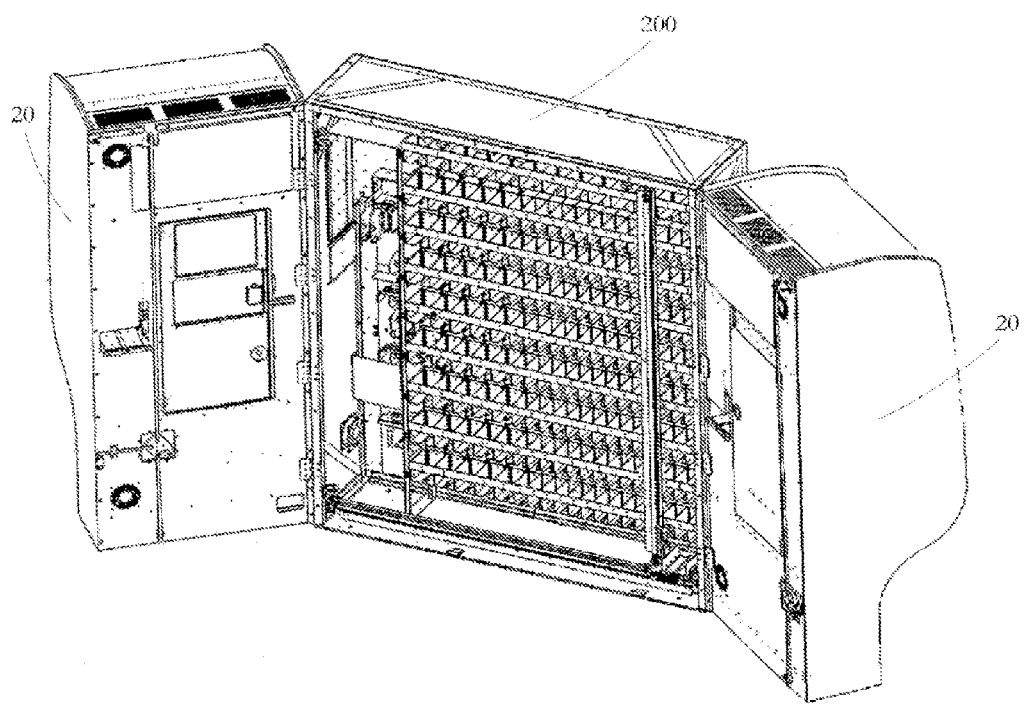
FIG. 13C shows an opened apparatus, together illustrating increasing levels of security for access to the apparatus.

The foregoing staged error resolution process, by which the dispensary apparatus 30 determines when an error state occurs and is able to resolve the error which has been detected, serves to maximize the in-service time of the apparatus, maximize patient utility, provide a rapid response to an error, provide a low service cost structure and optimize security for the machine and the drug inventory. The physical security of the dispensary apparatus 10 is enhanced by a staged access configuration of the apparatus as illustrated by FIGS. 13A through 13C. Access level one is illustrated by FIG. 13A and FIGS. 13B1 through 13B3 and provides access at locations 160, 170 to the front part of the apparatus which houses the user interface components, waste section, pick head garage and regular dispensary service items.

Access level two is illustrated by FIG. 13C and provides access to the drug vault module including its refrigerated section (if any) and its bulk storage containers which controlled and isolated. Two types of security are applied to these access levels. The technician must have a valid ID badge to allow entry to the front end of the apparatus.

A network video camera confirms the identity of the technician, that the technician's credentials are current and authorize the technician to access the machine at that time and that there is a work order created to track time and activity at the dispensary apparatus. In the event that a network connection cannot be established by the apparatus due to network interruption or prolonged power failure beyond the hold up time of an internal UPS, a controlled access key can be used for access to the level one interior space to restore power or network connectivity. Access to the level two controlled regions of the apparatus, such as the drug vault module, can only be achieved with network confirmation.

To optimize the user's utility in relation to the dispensary apparatus and serve a high traffic level, the apparatus must provide a high level of prescription coverage. An obstacle to doing so is that some medications, like insulin for diabetics, eye drops for glaucoma and several pediatric medications, require refrigeration for storage and such medications can be rendered ineffective if stored outside of their temperature range (e.g., if outside such range by two to eight degrees Celsius). On the other hand, some medications such as syrups require room temperature storage which is defined as fifteen to twenty-nine degrees Celsius.

Advantageously, the dispensary apparatus 10 of an implementation disclosed herein overcomes this obstacle by providing an isolated refrigerated section 250 in the drug vault module 200 that can store medications at controlled refrigerated temperatures in combination with a controlled room temperature section 240 in the drug vault module 200 to store medications at room temperature, as shown by FIG. 14. The apparatus also contains monitoring sensors (not shown) within the storage areas to sense internal temperature for the purposes of control of temperature, as well as to monitor temperature to report to a log file for correct temperature storage verification for a drug pedigree file and to report any temperature fluctuations in the form of high or low temperature alarms to the network for remedial action. Any drug that has been exposed to a temperature, or time and temperature beyond its allowable range is tagged to identify this via a drug pedigree established by the system and is removed from accessible inventory for disposal.

As in the known medication dispensary apparatus, the apparatus 10 of an implementation disclosed herein is able to dispense only pre-packaged product, being single unit items referred to as "standard dosage" items or packages. Pre-package products indicate that the items are appropriate for use in the dispensary and for dispensing to users but the actual number of pills, capsules, etc., contained in a given standard dosage package will vary based on the drug and dosing regimen. This regimen is derived from information provided by the drug manufacturer and the common dosing practices for the drug in question. However, from the perspective of utility function for the user, the dispensary apparatus is non-functional if the prescription requires 10 pills and the apparatus only stocks 8 pills standard dosage packages. The apparatus 10 solves this common problem by providing in its back end drug vault module 200 a bulk medication storage area 215 and pill counters 270 integrated into bulk storage containers for pill/capsule products 230.

A common problem encountered in autonomous pill counting is reliable, secure and clean handling of medication without cross contamination. The apparatus 10 includes a larger bulk pill/capsule storage container 230 that allows medication to be securely stored in bulk and sealed, and only touched by dedicated handling equipment until dropped into a dispensary package and dispensed to the user. This conforms to a no touch technique SOP to eliminate the possibility of cross contamination. The storage container 230 has specific dimensions to allow it to be stored in a standard storage slot, and specific features to enable reliable handling by robot. It also has specific security features to make it tamper resistant in transit.

The bulk pill/capsule storage container 230 is shown in FIGS. 32A-B and allows the robot to select and cause pill/capsule medication to be delivered to a counting unit comprising a pill singulator 260 and counter 270 which are integrated into the container 230 as shown by FIG. 15. Tablets or capsules are stored in hopper of the container 230.

In one implementation of pill dispenser, a vibratory scroll feeder (not shown) aligns the medication from the hopper, before it passes to the counting unit which counts the number of pills or capsules directed by the robot. When the product count is reached, a flap mechanism (not shown) diverts the pill flow back to the bulk storage container 230.

Another implementation of pill dispenser is shown in FIGS. 32C-H. Each of an array of bulk storage containers, of which one 402 is shown in these figures, contains pills 404 of a certain type. The container 402 has a pill guiding exit chute 404 and a vertically disposed, integrally formed cylindrical exit nozzle 406. Mounted within the exit nozzle is an annular cylindrical limiter 408. The limiter 408 can be moved up and down within the nozzle 406 by a drive mechanism (not shown) to alter the width of an annular exit region 410 extending between the limiter 408 and a conical hub part 412 of a disc 414. A ring gear 416 on a lower surface of the disc 414 has teeth that mesh with a pinion gear (not shown) from which a drive is taken to drive the ring gear to rotate the disc 414. The disc is mounted so that its upper surface slopes downwardly towards the hub part 412 to define a dish form. The disc 414 is formed, at least at its upper surface, of a material having a high friction coefficient and also has an integrally formed series of low profile curved fins 418.

Figure 32C:
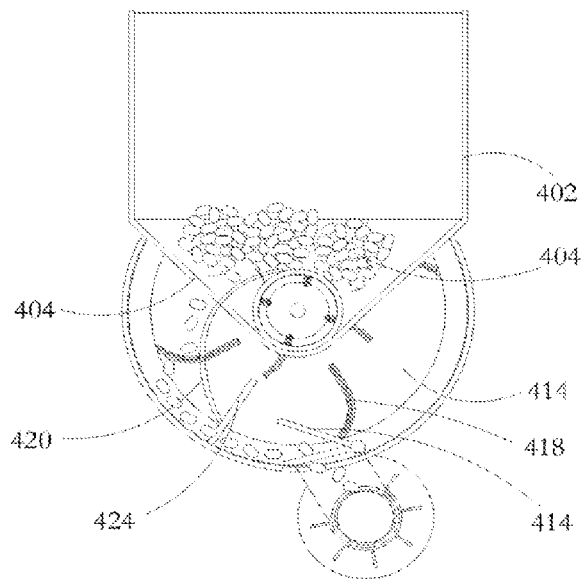
Figure 32D:
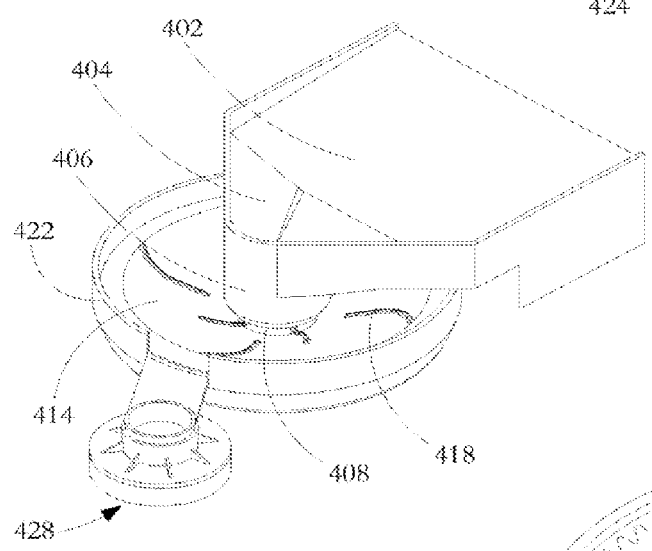
Figure 32E:
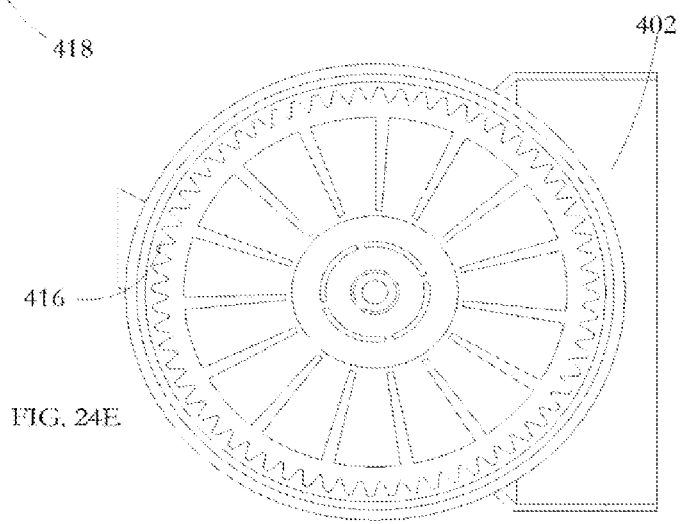
Figure 32F:
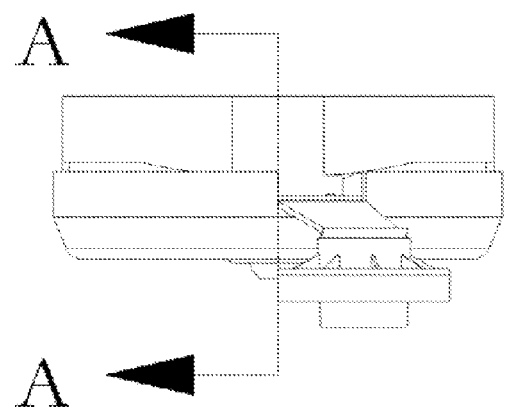
Figure 32G:
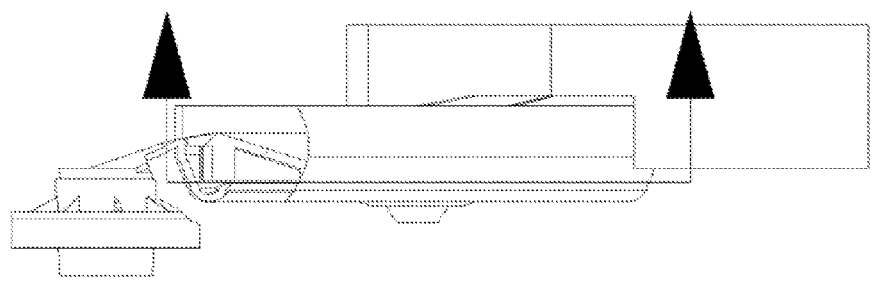
Figure 32H:
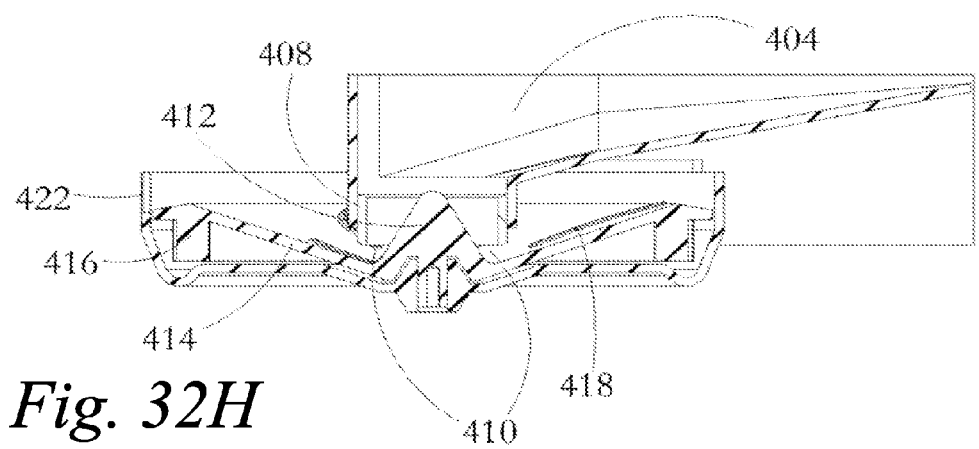

As shown in FIG. 32C, mounted above and with its lower edge closely adjacent the disc upper surface is a wiper guide 420, the guide having an inner end close to the hub part 412 and a generally spiral form extending almost to an outer edge of the disc. Mounted close to the disc upper surface and immediately adjacent a barrier wall 422 within which the disc spins is a separator 424. The separator is a generally radially extending plate which, with the barrier wall 422 and the disc upper surface, defines a triangular shaped opening. The separator 424 is downstream of the end of the spiral wiper guide 420 in the disc spin direction and a radially reciprocal gate 426 is downstream of the separator. The wiper guide, separator and gate are shown only in FIG. 32C.

In operation, a prescription is read and interpreted as previously described and instructions are sent to a pill dispenser control module indicating that a prescribed number of pills of a certain type are to be dispensed from an inventory store of such pills contained in a selected one of the bulk storage containers 402. As a result of the instruction, drive is provided to the selected pill dispenser to cause its drive gear to start the disc 414 spinning. A further drive is applied to move the limiter 408 to a predetermined position at which the size of the annular exit region 410 is appropriate to allow successive pills 404 to fall under gravity at a metered rate through the exit region 410 and onto the disc upper surface. The limiter position is set so that the rate at which pills pass through the exit region is not so large as to overload subsequent pill counting and pill packaging stages of the apparatus, but is also not so small as to result in jamming of the pills in the exit region 410. Once the pills fall onto the disc upper surface, the disc surface, the fins 418 and the wiper guide 420 interact to drive the pills in a spiral path towards the barrier wall. Pills driven towards the outer edge of the disc tend to become distributed and to be driven in arcuate paths next to the wall barrier 422. Ideally, the pills are strung out and pass successively through the opening in the separator 424. If however multiple pills adhere together owing to static friction or other surface condition, the separator 424 allows passage of only one of the adhering pills at time with any adhering pill being stripped away and subsequently presented to the separator by the spinning disc.

Under a solenoid drive (not shown) from the control module, the gate 426 is held in an open, pill passing position as long as a full count of the pills to be dispensed has not been reached. After the pills are discharged through the gate by the disc drive, they fall through a count zone 428 into a previously positioned empty pill bottle. In the count zone, the pills drop past an array of photodiodes and associated photodetectors (not shown). The photodetectors are set to record a pill count as each pill drops into the pill bottle. Software control is applied to close the gate when the number of pills counted matches the number of pills prescribed on the prescription.

Prior to the pills being dispensed through the count zone, an empty pill bottle is brought to the selected pill dispenser and lodged in a position where the pills dispensed from the bulk storage container drop into the bottle. The pill bottles are retrieved and moved by the control system which, as previously described with respect to the picking and delivery of pre-packaged medicament products, can be driven on X and Y axes to range over the full vertical area of the medicament vault. The control system can also be moved to a bottle zone where an array of empty bottles of various shapes and size, together with an array of matching caps, are stored. The control system incorporates a pick head described previously with respect to picking the prepackaged medicament products, the pick head having a finger and hook with the finger being reciprocal along the Z-axis. In operation, at the bottle zone, the finger is driven in the Z-axis direction to a position under a slot in the base of a container into which the bottle is dropped following previous software controlled selection and release from a bottle storage bandolier. As in the case of the prepackaged medicament product manipulation, the finger is moved upwardly in the slot to support the empty bottle. As the finger is withdrawn along the Z-axis, the hook engages the bottle to withdraw it from the container.

Also mounted on the control system is a platen. An articulator mechanism forming part of the control system grips the empty bottle and moves it onto the platen and into an upright position where it is locked relative to the platen.

The control system is then operated to deliver the platen to a position where the standing bottle is positioned to receive pills that drop from the selected pill dispenser. The control system also includes a cap pick and placement module. Following the dispensing of the desired number of pills into the bottle as previously described, the cap pick and placement module places a selected cap on the open neck of the bottle and a levering mechanism applies downward pressure on the cap to snap it over the neck. The control system is then driven to deliver the bottle containing the dispensed pills to a delivery zone accessible by the kiosk user.

It will be understood that FIGS. 32A-H describe just two forms of pill separator and counter for use in a networked arrangement to dispense both pre-packaged and bulk medicaments. An implementation disclosed herein envisages other forms of dispenser for pills, lozenges and capsules and also envisages the dispensing and packaging of bulk liquid medicament in an arrangement that is similar to the pill dispensing arrangement other than design changes to accommodate the handling of a liquid.

Both in the pill dispensing and the liquid dispensing arrangements, care is taken to avoid contamination of the medicament being dispensed. Thus, where possible, mechanical control elements are encapsulated and contained to avoid the escape of dust and vapors. In addition, where possible, dust, liquid and vapor seals and barriers are installed at locations where elements of the dispensing mechanism move relative to one another.

The prescribed medication is then transferred to a medication packaging module 280 (see FIGS. 16A-16B) via a vibratory scroll feed conveyer mechanism (not shown). Alternatively, the apparatus could be configured for placement of the medication packaging module at the counting unit's discharge port. The bulk pill/capsule storage container 230 is sealed and secured.

Optionally, the apparatus 10 may be configured so that the bulk pill/capsule storage container 230 can only dispense medication when inserted into a dispensary module under control of the robot. Such a configuration allows for tight batch and inventory control and maintenance of the drug pedigree. The prescribed counted medication is loaded into a hopper 290 of the packaging module 280 and is packaged by a bottle or foil packager 300, 310 of the packaging module 280. Optionally, the medication count may be verified optically during the transfer between the counter unit and the packaging module. The hopper 290, vibratory conveyer and counting unit (and optionally the transfer port) are optically inspected to confirm that no medication remains at those locations (i.e. no medication was left behind), before the bulk medication container 230 is cleared for the next use. The mediation packaging module 280 is configured for packaging medication in two ways. Firstly, it can bottle medication, insert sterile bulking material and apply a cap. A cap spinner (not shown) applies a known torque, the removal torque is tested to verify cap function and re-torqued to the original torque setting. A drug pedigree certificate produced by the system adds to the pedigree a "cap good" notation. Secondly, the medication packaging module 280 can load medication into sterile foil seal pouches, apply a foil seal and verify seal via visual inspection.

Figure 33A:
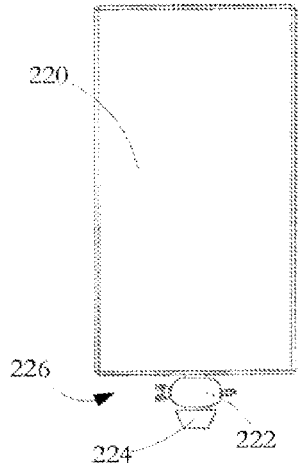
Figure 33B:
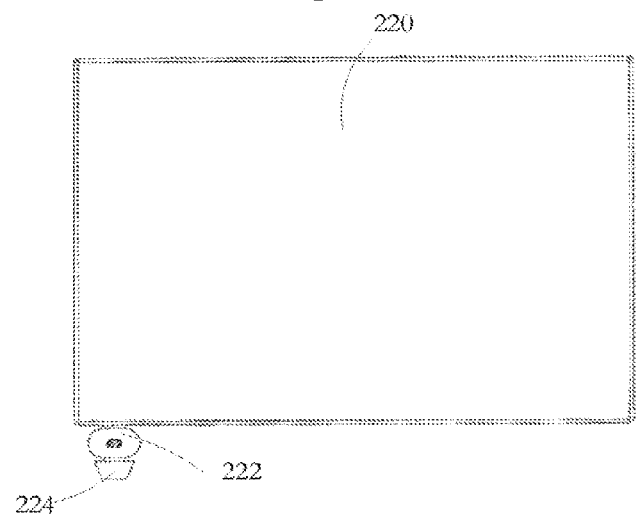
Figure 34A:
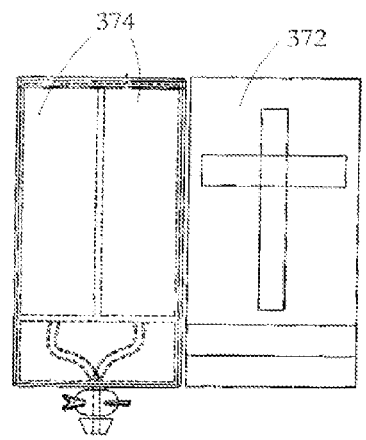
Figure 34B:
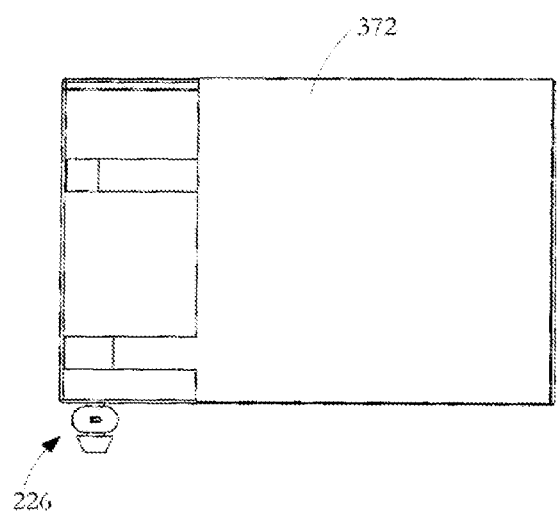
Figure 36A:
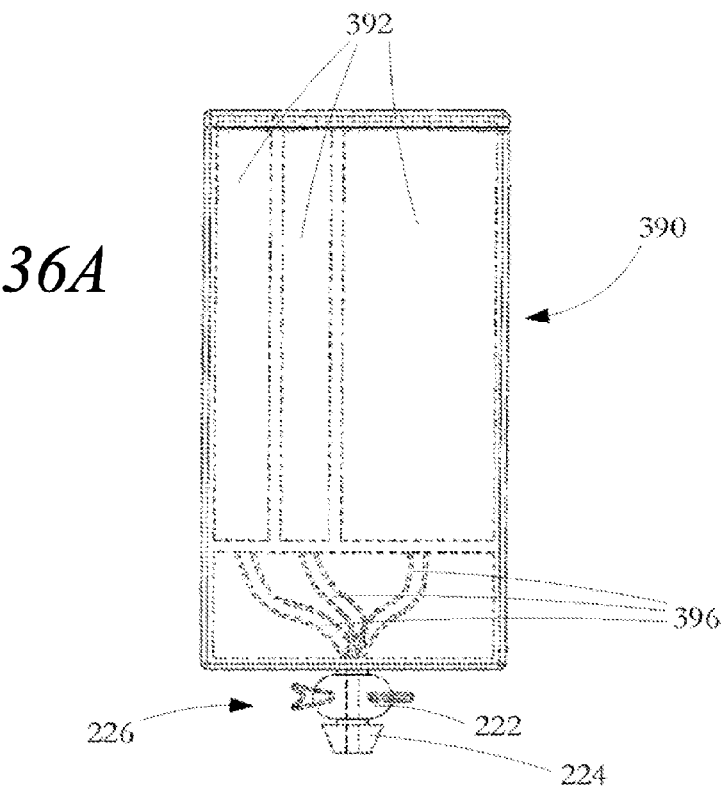
Figure 36B:
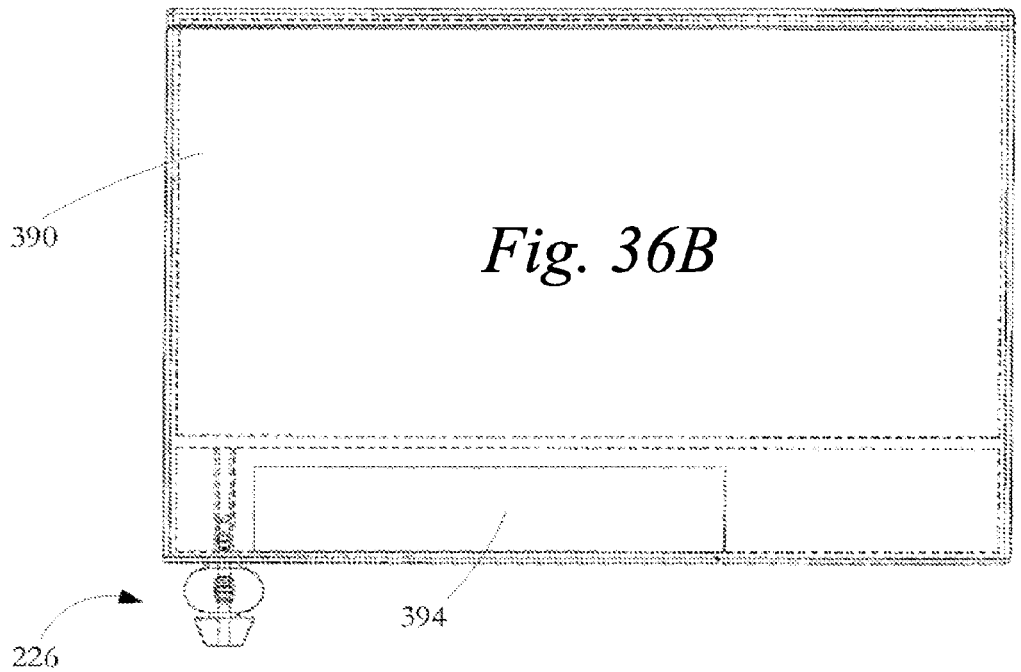

Standard dosage packaging also presents an obstacle for liquid medications, especially pediatric medications and maintenance drugs where dosage can vary widely. To resolve this obstacle, the dispensary apparatus 10 of an implementation disclosed herein provides a bulk storage container for liquid product 220 with an integrated pouring unit 226 as shown by FIGS. 33A-B. This bulk liquid medication container 220 is operated by the robot to pour a measured amount of medication into liquid dispensing containers (not shown). Some medications require reconstitution generally with another liquid prior to dispensing. A reconstitution bulk storage container 370 is shown in FIGS. 34A-C and includes a mixer/agitator 32 and a liquid/concentrate storage section 34 for adding liquids to concentrates and pass them to a mixing cell for stirring or agitation. Similarly, some medications require mixing of two or more components prior to dispensing. A mixing bulk storage container 380 is shown by FIGS. 35A-B. The mixing container 380 includes liquid storage sections 382, a mixer 384 and mixing valves and piping 386 for measuring and dispensing mixed medication to a liquid dispensing container according to any number and amount of liquid components by weight, volume or percentage. Further, some medications require geometric reduction of one or more components in a carrier. A compounding bulk storage container 390 is shown in FIGS. 36A-B and includes liquid storage sections 391, a mixer 394 and mixing valves and piping 396 for performing geometric reduction of one or more components in a carrier.

A problem which has not been overcome by prior art dispensary apparatus is a failure to provide means for reliably applying standard flat labels to the dispensed medication product. Labels are typically applied by the conventional means of running pressure sensitive adhesive back coated labels on a peal away carrier through a label printer and transferring the printed label to a bottle or box, but achieving reliability of good placement and adhesion reliability has been a problem. Labels must be a standard shape and size to pass through the printer, and must contain critical patient and medication information, conforming to industry standards offering little creativity in shape, size or materials. Several transfer methods have been previously disclosed including sponges, vacuum, sponges and vacuum in combination, transfer media, transfer roller and pressure pads. The apparatus 10 of an implementation disclosed herein solves this problem in a novel and simple way by using the label itself as an applicator. A package labeling module 330 of the apparatus is shown in FIGS. 18A-18F. The label stock is paper or plastic stiff enough to support the label without sagging from edge to edge along its longest side. The label is ejected from the printer and attached to a continuous release liner. The release liner wraps around a small diameter roller, causing the label to separate from the release liner. The release liner advances to the point where ⅞ of the label is detached from the release liner. The robot's pick head 50 picks a product to be dispensed by the apparatus and brings the product to the suspended label, aligning the front edge of the label with a preselected contact start point on the product package. The robot's pick head 50 rotates the product away from the small diameter roller, rolling the label onto the product, and dislodging the remaining of the label from the release liner. The product, with label attached, is then transported and pressed label-side down, onto a conformal sponge contact patch that applies adequate pressure to contact the label to all parts of the package with sufficient pressure to activate the contact sensitive adhesive. Because the size and shape of the package of the product is known to the robot, accurate placement is possible with this method, with high reliability and repeatability, and without the adhesive residue problems of the prior art.

A parts description listing for the parts shown in FIGS. 18A-18F is provided by the following table:

Item no. Description L01 Nema 23 Stepper Motor L02 Nema 23 Reducer 10:1 L03 Stepper controller L04 Banner miniature polarized retro reflective sensor LOS Banner square reflector 60 mm×40 mm with mounting holes L06 8 mm, NO, PNP Inductive Prox w I 8 mm Quick Disconnect L07 M8, Inductive Prox w I 8 mm Quick Disconnect LOS ABS Resin Conveyor Roller 20 mm OD×99 mm lg. L09 XL Timing pulley 15 teeth L10 XL Timing pulley 30 teeth, 10 mm bore with setscrews L11 XL Timing Belt, 105 teeth, 533.4 mm long (Poly with Kevlar) L12 10 mm double bearing housing L13 Knurled lock nut M20×2.5 L14 2 mm E-Clip L15 Large diameter knurled screw MS tapped L16 Linear bearing rail 135 mm Lg, 2 bearing carriages L 17 MS Threaded Stud, 95 mm Long L 18 5 mm Pivot Pin, One end Threaded with Flat, 85 mm Long L19 3 mm Shaft×1121 g with 2× E-Clip grooves L20 6 mm Shaft×811 g with tapped M3 End L21 10 mm Shaft×601 g with 2× Retaining Groove L22 Resin Pipe, 5 mm OD, 3 mm ID×1001 g. L23 Constant Force Spring, 0.1 kg force L24 5 mm E-Clip L25 6 mm Hexagonal Base Cantilever shaft, 100 mm Lg with 2 mm Base, M6 Thread L26 6 mm Hexagonal Base Cantilever shaft, 100 mm Lg with 20 mm Base, M6 Thread L27 Resin Pipe, 8 mm OD, 6 mm ID×1001 g. L28 6 mm shaft, 101 mm Lg. Threaded M4 both ends L29 6 mm shaft×112 mm Lg. with 2× E-Clip Grooves L30 Polyurethane Foam Rod 2" 29 L31 Polyurethane Foam 2¼" Square L32 Seiko Thermal Label Printer Seiko CAP9000 USB Board Seiko—Control Cable L33 10 mm External Retaining Ring L34 DC Gear motor, 187.68:1 reduction ratio L35 XL Timing Pulley, 12 Teeth L36 XL Timing pulley 20 teeth, 10 mm bore with setscrews L100 Labeler Plate L101 Label Stock Trap Plate L102 Label Take-up plate L103 Take-up Spindle L104 Label Backing Back Guide Plate L105 Label Backing Front Guide Plate L106 Label Take-up Drive Shaft L107 8 mm Prox Mount Angle L108 Label Stock Collar L109 Constant Tension Spring Mount L110 Banner Sensor Bracket L111 Labeler Mount Plate L112 Foam Mount Bracket L113 DC Gear Motor Mount L200 5 mm×25 mm, Shoulder Screw.

Figure 19:
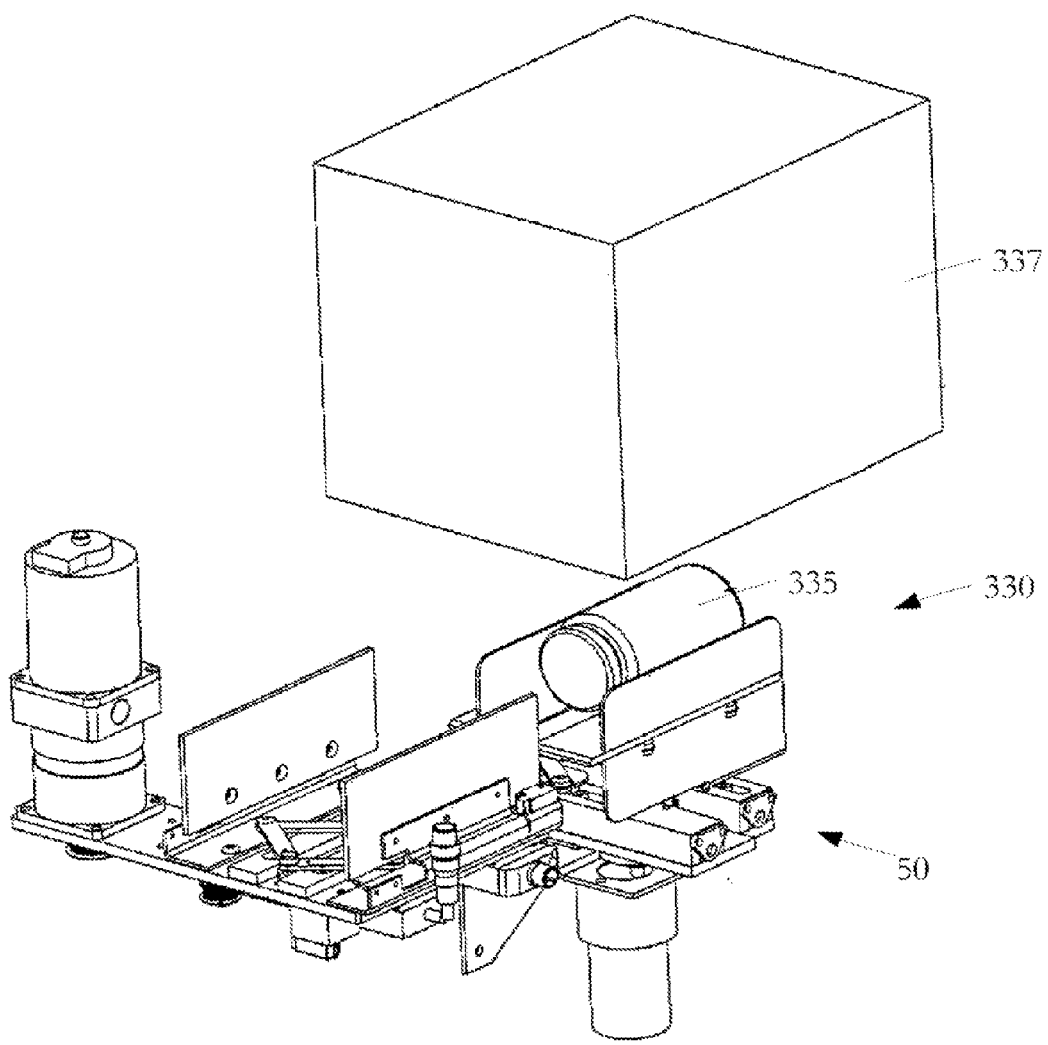
FIG. 19 illustrates a laser marking module of the automated apparatus implementation disclosed herein, configured for direct marking of label information onto a package to be dispensed by the apparatus to a user.

In addition, the apparatus 10 provides a further improvement for product labeling in the form of an optical scribe 330 that writes directly to a product package (container) to be dispensed. FIG. 19 shows a laser marking module 330 directly marking (labeling) a product container 335 positioned on the robot's pick head 50. By the addition of a light sensitive coating on the container 335 the laser marking module 330 writes readable information directly onto the container 335 without the requirement for a transfer label and the associated complications of label transfer, placement and adhesion.

Loading a dispensary apparatus with medication is a time consuming, tedious, laborious, highly repetitious task, and as a result, is subject to error. Removal of these human factors at the loading point is important for reducing errors in a drug supply chain. The known loading methods have relied on RFID tags to verify the drug, requiring a human operator to flash each product against an RFID sensor which verifies the drug and identifies (e.g., by a light) the appropriate storage slot to direct the operator to the location of correct placement. Apparatus using such known methods display, on an inside screen, a picture of the drug with data, DIN, lot, etc., and then says the name of the drug using a text speech generator. The downfall of those prior methods and apparatus is the amount of time required to verify each product, and the additional cost in the apparatus of an the indicator light system with related software and hardware to drive the lights, in addition to the cost of an RFID tag in each and every product.

Figure 20:
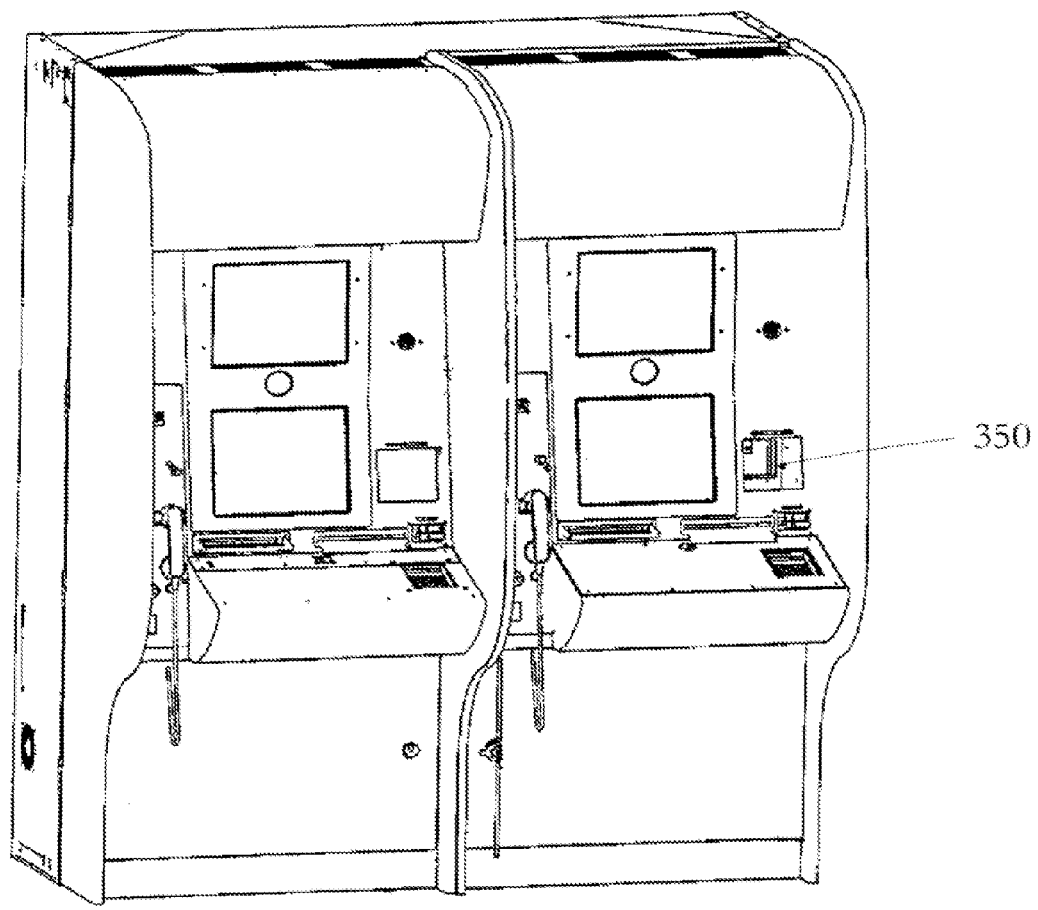
FIG. 20 illustrates, in the front end user-interface module, a manual product load slot for manually loading product, whereby the product passes to the control system for automatic self-loading of the product into the drug vault by the control system of the apparatus.
Figure 21A:
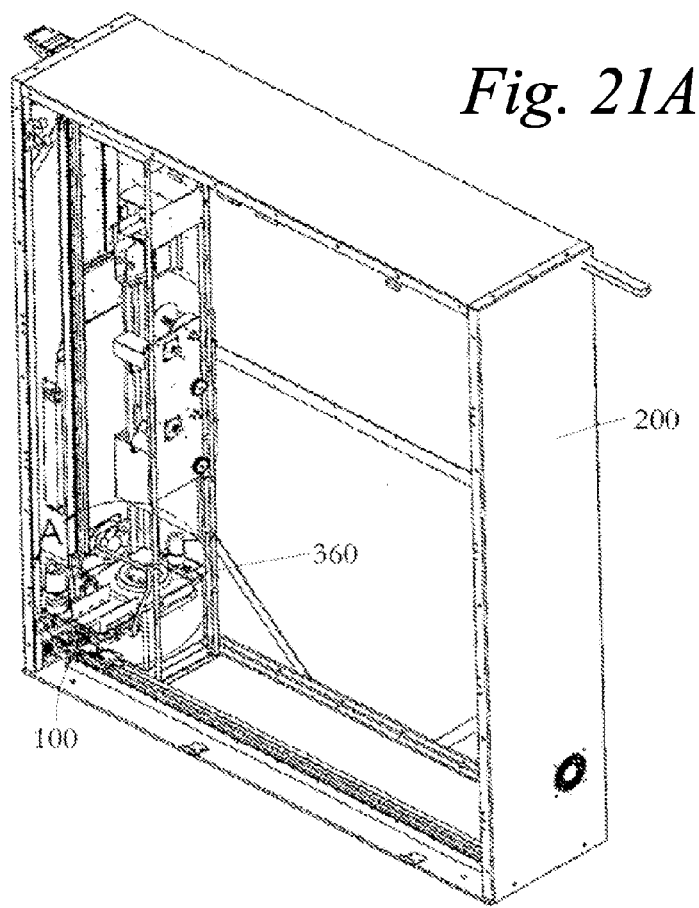
Figure 21B:
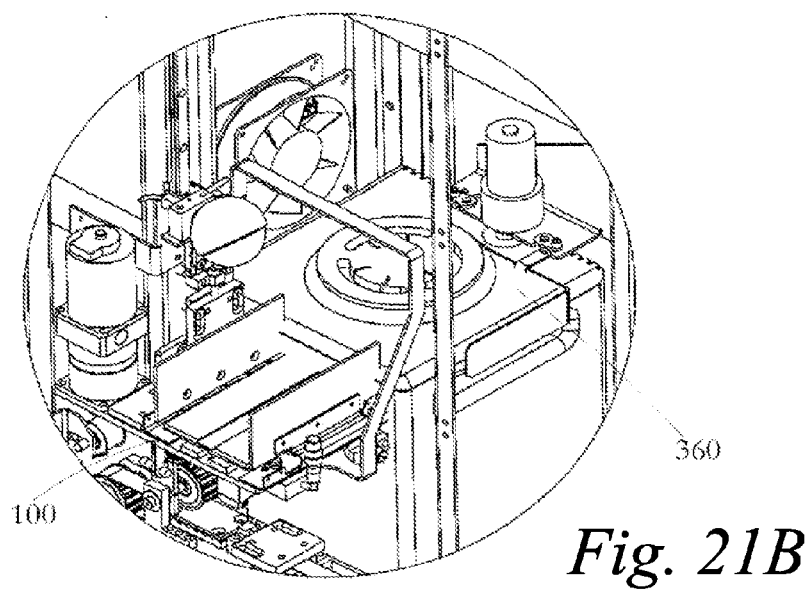
Figure 23A:
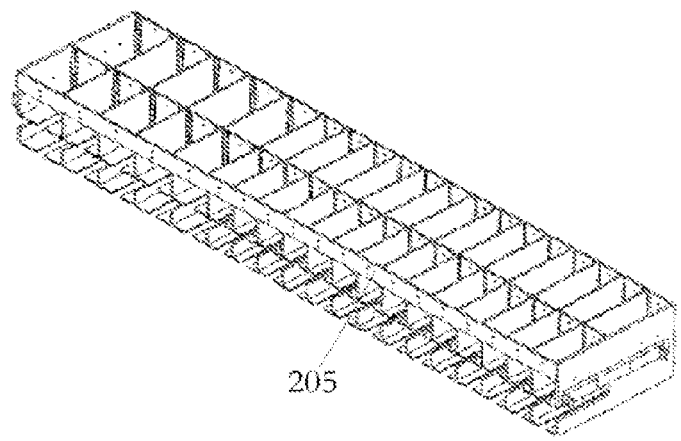
Figure 23B:
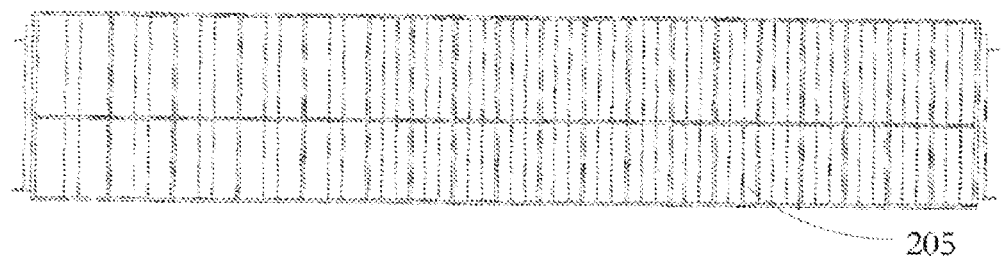
Figure 23C:
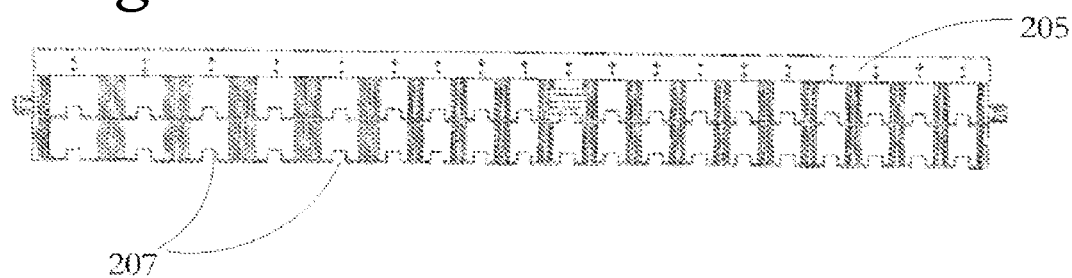
Figure 23D:
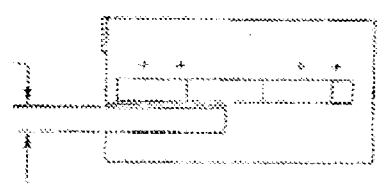

The dispensary apparatus 10 of an implementation disclosed herein uses either an RFID tag, if any, or the optical product coding which is already in place on pre-packaged product, which is read by the robot and used by the robot to automatically place the products in inventory in the apparatus, without requiring an operator to open the machine. The robot and the networked computer system then know, with absolute certainty, the location of all products in the machine and the state of the inventory, without the possibility of human placement error. Product loading occurs in two modes. Firstly, the apparatus provides means for manual loading of product by an operator, after the operator has passed a security test to place the apparatus in a manual load mode. Product is placed in a manual load slot 350 for robotic self-load as shown in FIG. 20. When product is manually placed in the load slot 350 it is accepted by the robot, read and placed in inventory in the apparatus. The cycle completes until inventory storage of the product load is complete. Secondly, the apparatus provides means for automatic loading of product as shown by FIGS. 21A-21B. A secure transfer container 360 is used for secure transport of drugs and automated loading into the apparatus.

In the automatic load mode, the operator places the secure transfer container 360 into the apparatus in a receiving port and the control system 100 automatically loads the products into inventory while not required for other tasks. When full loaded, the empty secure transfer container 360 is used for receiving waste to be returned from the apparatus to the distribution center so the transfer container 360 also serves as a waste container 115 in this mode. The secure transfer container is shown in FIGS. 22A-22D and is configured on the basis of its contents, with several types being provided including a refrigerated type, a non-refrigerated type, a prepackaged product type, a bulk liquid type and a bulk pill type. A universal type secure transfer container 360 is also provided.

Figure 30A:
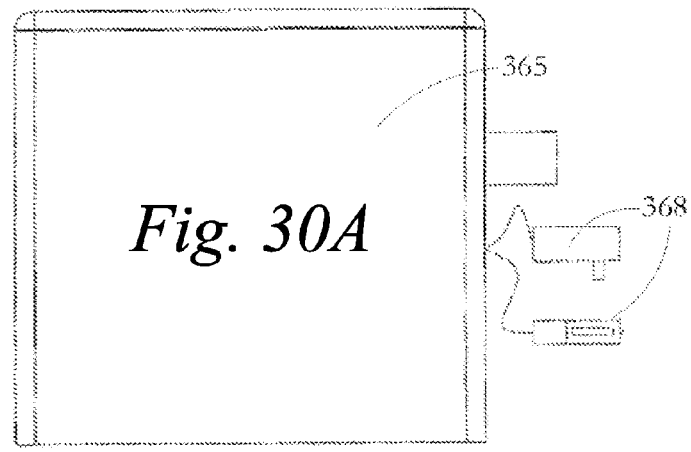
Figure 30B:
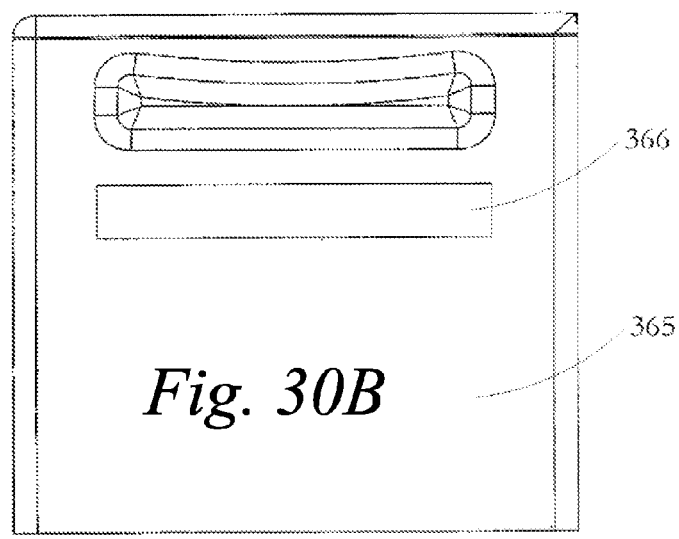
Figure 31A:
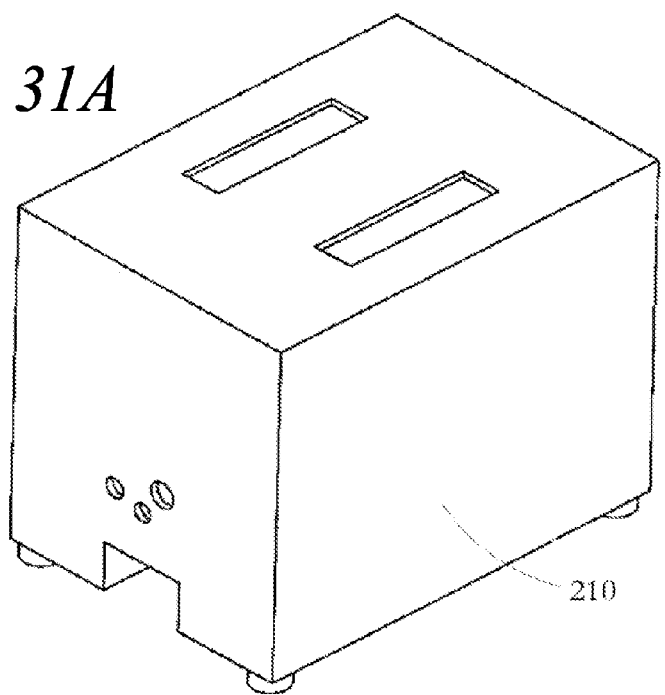
Figure 31B:
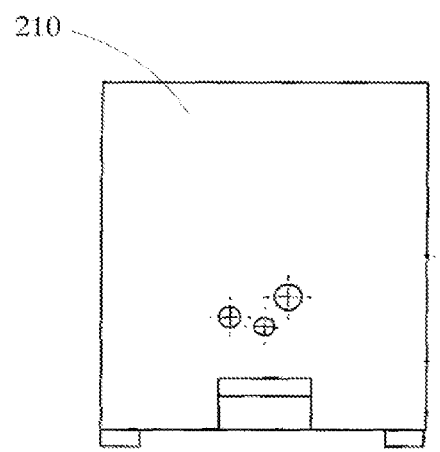
Figure 31C:
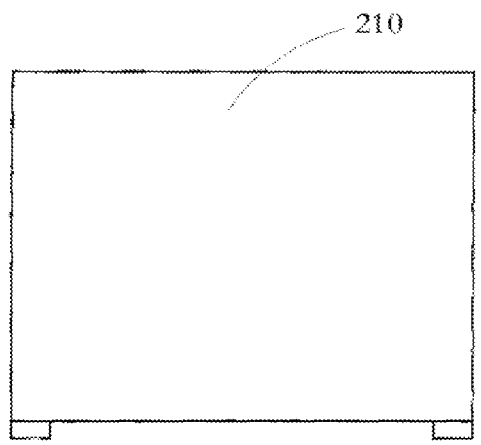

The refrigerated type secure transfer container 365 is shown in FIGS. 30A-B. It is insulated and refrigerated with an external power supply hook up 368 to provide active refrigeration during transport or storage on route, and it contains a Peltier effect type solid state cooling device 366 and a temperature monitoring system. The secure transfer container 360 is a secure device that can only be opened by the robot once it is inside the apparatus or at the distribution center and provides a secure transfer vessel for the drug products as they travel between the apparatus and the distribution center, whereby a common carrier may be used for transporting the products. As stated, a measure of utility for the apparatus is that a drug requested by a user must be available from the apparatus from which it is requested. A back end drug vault module 200 of the apparatus 10 has a fixed number of storage slots 207 for product.

As shown by FIGS. 23A-23D, each storage slot 207 can store up to five units of the same product SKU. In locations such as a busy primary care clinic or hospital emergency room, this may not be adequate storage to meet the demand for high demand medications to be in stock all of the time with a reasonable restocking cycle time, making it possible to run out of a high demand medications before the next restocking visit, especially during epidemic seasons or events. In such locations, multiple modules of the apparatus can be co-located to duplicate or multiply the number of user interfaces present, allowing more than one patient to be served at a time. Further, the apparatus 10 is configured to allow for the inventory product of one drug vault module 200 to be picked and securely transferred by a control system 100 to another co-located drug vault module 200.

A patient may be served by a first apparatus 10 for which some components of the medication requested may be out of stock within that apparatus but available and in stock at a second apparatus 10. The first apparatus 10 queries the second apparatus 10 for availability, if the product is available, the first apparatus requests a secure transfer of the medication. The robot of the second apparatus is instructed to carry out a product pick, scan and verification that the product is correct, then deliver it to a left or right side secure transfer slot of the apparatus (not shown).

The robot of the first apparatus travels to a right or left side secure transfer slot of that apparatus and, when in correct position, a transfer order handshake is exchanged between the first and second apparatus, allowing the transfer ports to open and the requested product to be passed from a platen of the robot of the second apparatus to a receiving platen of the robot of the first apparatus. After the transfer is complete, the second apparatus retracts its robot platen, verifies that the transfer was completed and closes its transfer door. The robot of the first apparatus verifies the product received, confirms identity of the product against the drug record, and continues the dispense cycle in the same manner as if the drug had been located within the drug vault module of the first apparatus.

Multiple apparatus 20 can be co-located, for example in a three apparatus co-location installation, a first apparatus can request medications from the third apparatus whereby the second apparatus is instructed to act as an intermediary and pass the medication through that apparatus. Further, from the user's perspective of utility, there is no such thing as an obscure medication. If a medication has been prescribed, it is what is wanted and needed immediately to commence healing. The user does not accept that a particular medication it needs is rarely sold, so seldom stocked. To the patient, the utility value of the dispensary apparatus is its ability to dispense the medication needed as and when requested. For example, there are many medications for tropical diseases that are necessary, but dispensed infrequently. The apparatus 10 of an implementation disclosed herein applies a method with enabling hardware and software to designate specific storage slots 207 as multiple product SKU garages. The slots 207 are vertically oriented, and operated on a first in-first out inventory control rule. This is accomplished by picking product from the bottom of the slot and placing new product on the top of the slot.

In a garage-type designated slot containing five different individual product SKU's, the desired product may be the third product in the slot. The robot travels to the slot location and picks item one, picking from the bottom. The robot returns item one to the top of the same slot for restocking. The robot returns to pick item two, again returning it for restocking. The robot then picks item three, the desired item, verifies it and proceeds to a dispensary preparation cycle. The system's product inventory location register is corrected to show that former product one is now in position three, that former product two is now in position four, that former product three is now in position one and that former product four is now in position two, with the slot able to accept one additional product SKU on restock.

The refrigerated storage module 250 of the apparatus 10 is shown by FIGS. 27A-B, FIG. 28 and FIG. 29. It has an insulated perimeter and an insulated, sliding door 252 which can be opened in a low clearance environment by means of a sliding mechanism or track such that it opens to expose its internal contents to the robot, and moves out of the way on a plane perpendicular to the X-Y axis of motion of the robot pick head 50. Its track has a shape or the door has a mechanism whereby the door is sealed at the perimeter when closed, and moves away from the seal, or the seal collapses or moves away to provide clearance for the door to operate. The door is operated by a linear actuator, pulley, cable, cogged belt system, or by a latch that can be engaged by the robot head to open and close the door. The refrigerated storage module 250 also communicates to an external vacuum pump 258 (or may contain a pump), capable of providing a reduction in barometric pressure within the refrigerated storage cell immediately after the door is closed, to set the door seal and to remove ambient air and moisture that was introduced into the refrigerated storage module while open. The refrigerated storage module 250 contains Peltier effect type solid state cooling devices coupled to heat absorbing aluminum thermo sink arrays to remove heat from within the refrigerated module without the requirement for a compressor, condenser and evaporator.

It will be understood that in dispensing inventory prepackaged products and inventory bulk medicament in such a way as to have a high first script ratio, a prevailing problem is the corresponding demand for a kiosk which has a high volume/footprint to accommodate a wide variety of medicaments, a wide variety of dispensing methods and a wide range of amount dispensing capabilities. It will be appreciated that the networked arrangement according to one aspect of an implementation disclosed herein permits certain of these activities to be conducted at a location remote from the kiosk which permits some reduction in volume/footprint of the kiosk. In addition, in the control system for medicament products containing dispensed bulk medicaments (either pill type medicaments or liquid medicaments) and for dispensing pre-packaged products, the kiosk volume and footprint is reduced by having certain elements of the control system commonly used in multiple stages of the dispensing process. This means that the dispensing of the wide variety of medicaments, by a wide variety of dispensing methods to achieve a wide range of dispensed amounts does not mandate a tailored plurality of control sub-systems.

Figure 37:
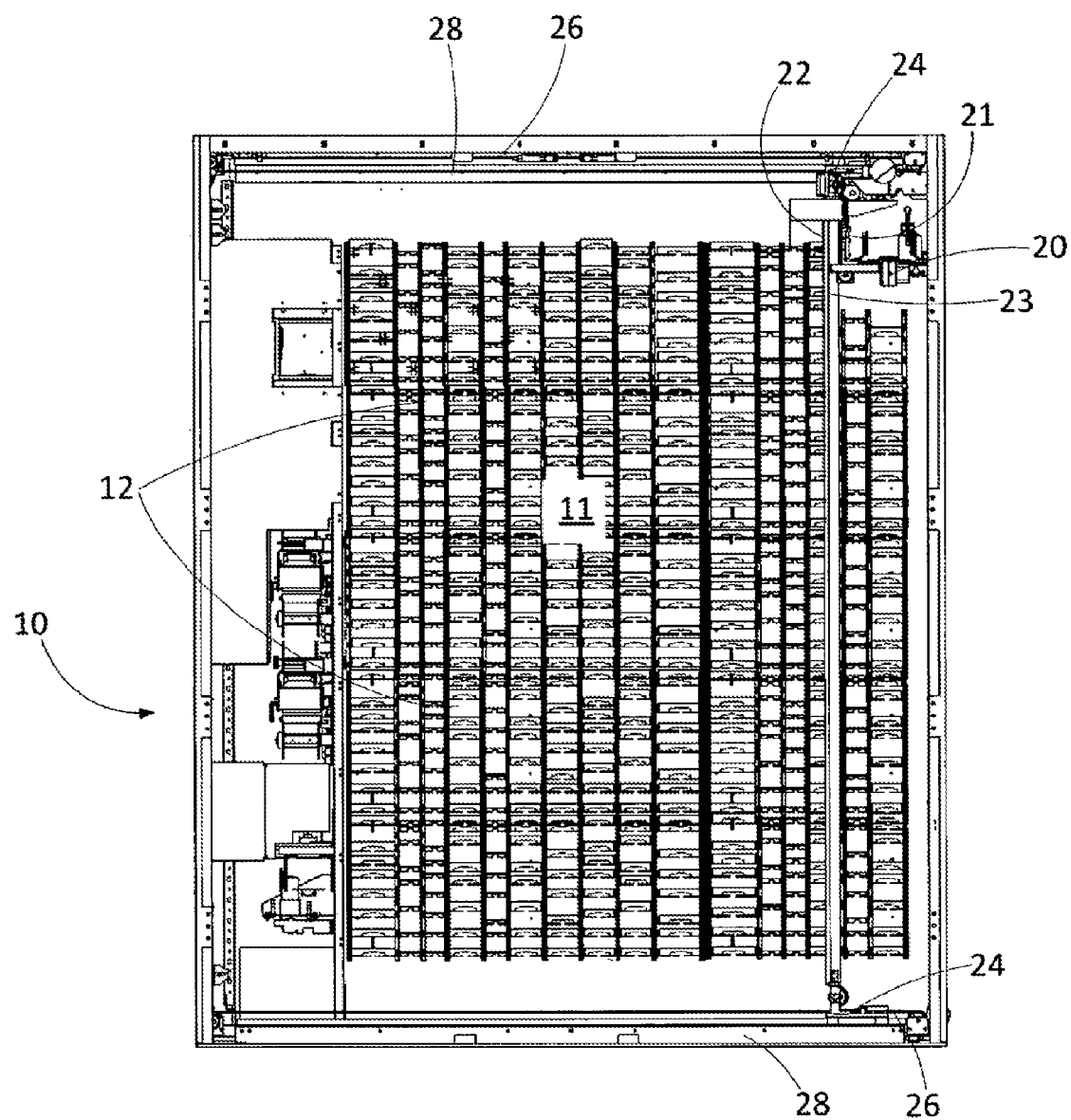
FIG. 37 is a front view of a storage apparatus for a package dispensing kiosk implementation disclosed herein.
Figure 38:
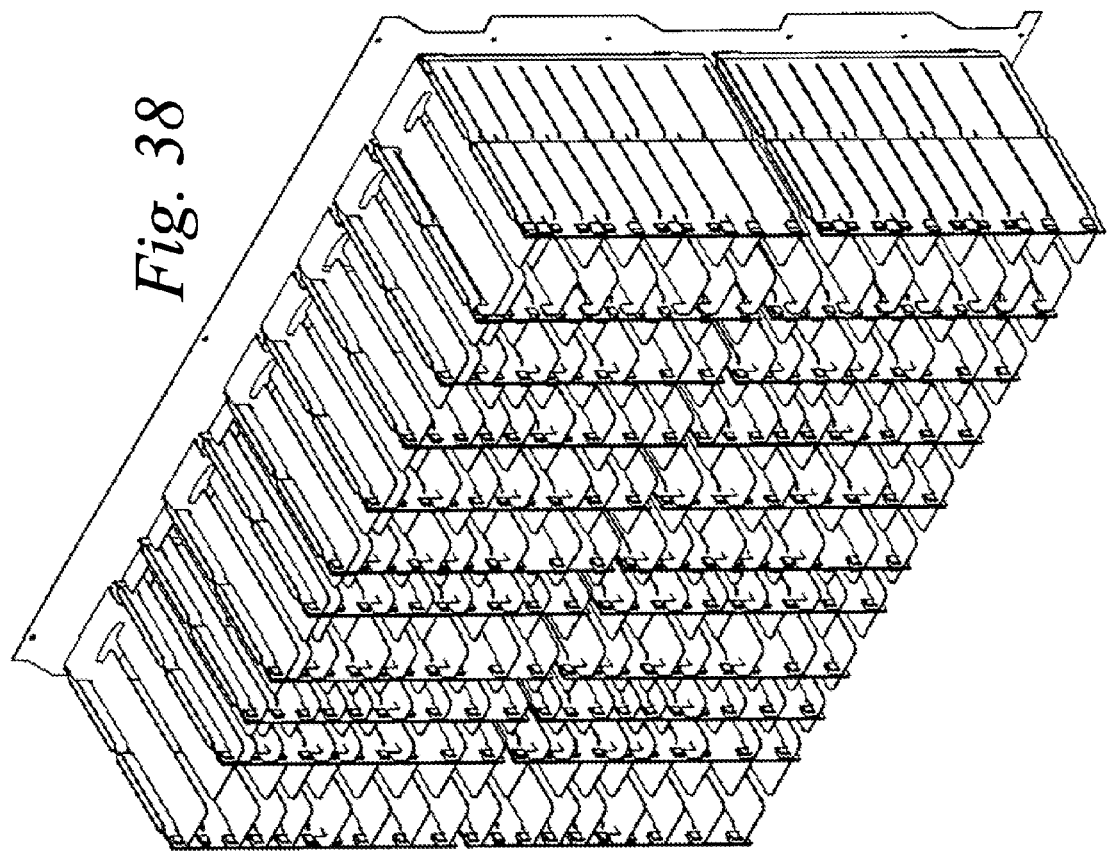
FIG. 38 is a perspective view of a bin rack forming part of the storage apparatus of FIG. 37.

In yet another implementation, and referring in detail to FIGS. 37-38, there is shown a cabinet 10 for a dispensing kiosk, the cabinet having a rack 11 of storage bins 12 arranged in a row and column array. The bins may be of a uniform shape and size or, as shown, may vary in shape and size to accommodate different sizes of packages to be dispensed. Particularly for the application envisioned for implementations disclosed herein, the rack of storage bins is formed as a secure back end medicament storage vault. The storage vault is in use combined with a front end unit (not shown) which bars unauthorized access to the drug vault but which can be opened to expose the drug vault for servicing. Mounted in the front end unit is an interface unit (not shown) at which a user, can enter data, communicate with a remote expertise or data records through a data or teleconference link, and collect dispensed packages, etc.

As shown in FIGS. 39-40, each bin has a pair of side walls 14 with the side walls of inner ones of the bins also being the side walls of immediately laterally adjacent bins. Similarly, each bin has an upper wall 15 and a lower wall or floor 16, with the upper and lower walls of the inner bins forming the lower and upper walls of immediately vertically adjacent bins. The rack of bins has a rear wall 17 extending the full extent of the array although, as an alternative, stub rear walls can be used for each row of bins in place of the fully extending rear wall. The bins have a front to back depth typically to accommodate a row of four packages. In a typical application, these are pill boxes or bottles, but may also be bottles containing dispensed liquid medicaments or may be different packages entirely. An implementation disclosed herein relates to the manner of picking a package, which may be a single package within a bin or which may be the first package of a vertical stack or of a horizontal row of packages which have to be selectively manipulated to obtain access to a desired package.

A chosen package is picked from its position in the rack of bins and, if part of a stack or row of packages, from its position within the stack or row, in preparation for dispensing the package at an access bay in the front end interface unit. Each of the bin floors 16 has a slot 18 which is generally centered within the floor and which extends from the front access side 19 of the bin to a position near the rear of the bin.

As shown in FIG. 37, a pick head 20 is mounted on a vertically reciprocal carriage 21 which is driven by a belt drive 22 along a vertical guide rail 23. The rail 23 is mounted between two horizontally reciprocal carriages 24. The carriages 24 are driven by belt drives 26 along horizontal rails 28. The carriages 21 and 24 move in a plane which extends parallel to a front access side 19 of the bin rack 11. In this way, the pick head 20 can be placed adjacent any selected one of the bins 12 at the front access side 19 of the bin rack.

Figure 43:
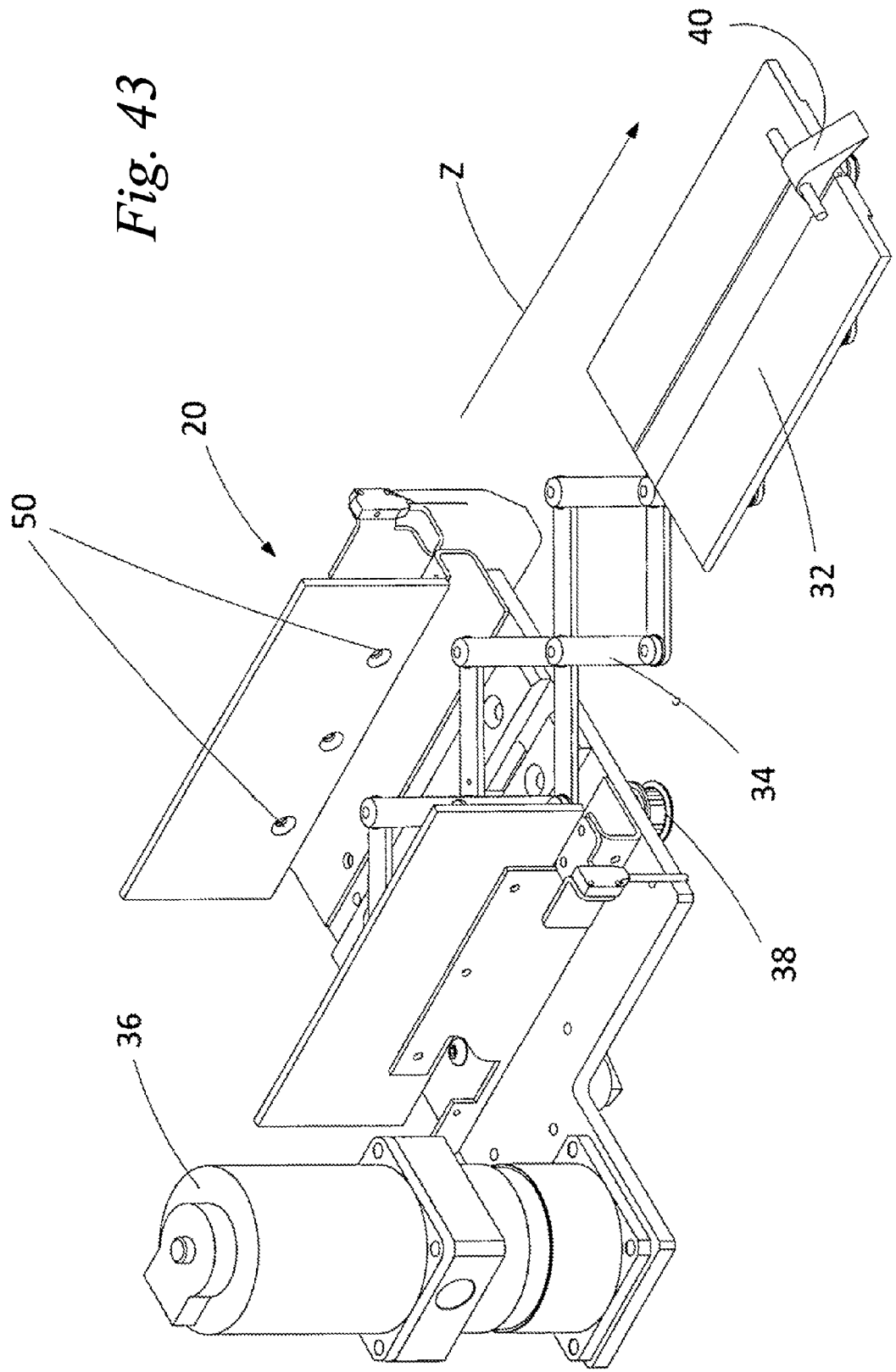
FIG. 43 is a perspective view corresponding to FIG. 40, but showing a reciprocal platform thereof in an extended position.

In an implementation disclosed herein, and as shown in perspective view in FIGS. 41 and 43, the pick head 20 includes a platform 32 and a scissors type telescopic supporting linkage 34 (FIG. 43) driven by a motor 36 and a belt 38. The motor and belt operate to drive the platform 32 reciprocally in the Z direction (as shown by the arrow in FIG. 43) rearwardly towards the selected bin from which a package is to be picked, and then forwardly to drag the picked package out of the selected bin and onto the platform 32 from where the selected package can be carried by the pick head 20 to various stations within the apparatus, such as checking and labeling stations (not shown) before being dispensed to a user. To reduce the chance of a package being dislodged or wrongly positioned on the platform as it is dragged from the selected bin, the platform can be formed with an upper surface that slopes downwardly towards, or is recessed at, a generally central region, so that a package supported on the platform is biased by its own weight towards the central region.

The platform has an upwardly facing cam formation 40 (shown enlarged in the scrap view of FIG. 42, the projection having a rear cam face 42 and a forward abutment face 44. To initiate a pick process, the platform 32 is driven by linkage 34 into the bin rack as shown in FIGS. 44-45. The platform is at a height at which it slides under the floor 16 of the selected bin as shown in FIGS. 46-47. As the platform is driven into the bin rack, the projection 40 passes along the slot 18 in the floor 16 of the selected bin with a top part of the projection 40 extending above the upper surface of the floor. A cross member 45 extending through the projection 40 is positioned so that as the platform 32 enters the bin rack, the cross member 45 becomes inserted in the junction between the floor 16 of the bin and the package to be picked. The cross member 45 has a number of functions. Firstly, it is supported by the floor 16 of the selected bin as the platform enters the bin rack and so acts to prevent the platform 32 from sagging. The cross member also aids in guiding the projection 40 into a proper position for subsequent retrieval of a package from the selected bin. The cross member also keeps the package being picked relatively aligned with the direction of pick head exit throughout the pick process. Finally, the cross member is of value in separating a package from the floor 16 of the selected bin and, in terms of depth, in separating a package from an adjacent package within a row of packages.

As alluded to previously, during a package picking cycle, the platform is driven rearwardly into the bin rack to pick up a desired package from the selected bin 12 and then is driven forwardly out of the bin rack to drag the picked package from the selected bin. Successive phases of the platform movement are shown as sectional views in FIGS. 44, 46, 47 and 48. In FIG. 46, the platform 32 has reached a position in its rearward movement in which the cam face is starting to lift a pill bottle 46 from the bin floor 16 and also forcing the bottle to tilt with the mouth end of the bottle 46 raised above the bin floor. As shown in FIG. 47, the platform has moved further rearwardly to a position where it has passed under the bottle's centre of gravity and the bottle is repositioned to alter its angle of tilt relative to the bin floor. After still further rearward motion of the platform, the platform reaches a drop position as shown in FIG. 48 at which the bottle 46, under its own weight, drops down against the bin floor with the abutment face 44 located adjacent a trailing extremity of the pill bottle 46. At this point, drive to the platform provided by the telescopic linkage 34 is reversed. As shown in FIG. 49, as the platform 32 moves forwardly out of the bin rack, the abutment face 44 bears against the bottle 46 to drag the bottle out of the selected bin with the bottle falling onto the platform and becoming supported by it as the platform emerges from the rack.

In the implementation shown in FIGS. 44-49, the package to be picked forms part of a row of packages with part of an immediately rearwardly adjacent pill box 48 being shown. As can be seen, as a result of the lifting and tilting movement of the pill bottle 46 and pill box 48 during the course of the pick cycle, the opposed ends of the two packages are forced apart. This has particular value in relation to two common problems in dispensing packages, especially in dispensing pill boxes from a row of such boxes.

One problem of dispensing articles such as pill boxes which are relatively lightweight is that packages may stick together causing two boxes to be loaded onto the pick head platform rather than one package. In the storage bin, two package boxes may be caused to stick together if they press against each other for a long period during storage, especially if the boxes are made of cardboard and have been subjected to humid conditions. This increases the chance that when the pick head lifts one box, it may actually lift both, creating a double pick error. The passage of the cam formation 40 completely under the first box—the package to be picked—and partly under a rearwardly adjacent box tends to cause a separation angle to open up between the two packages and, additionally, forces the packages incrementally from their stored positions to establish a temporary height difference at the interface of the two packages. If the attraction between the stuck faces is overcome in the course of the projection passing progressively under the two packages, then only the package intended to be picked will be dragged from the selected bin.

Figure 58:
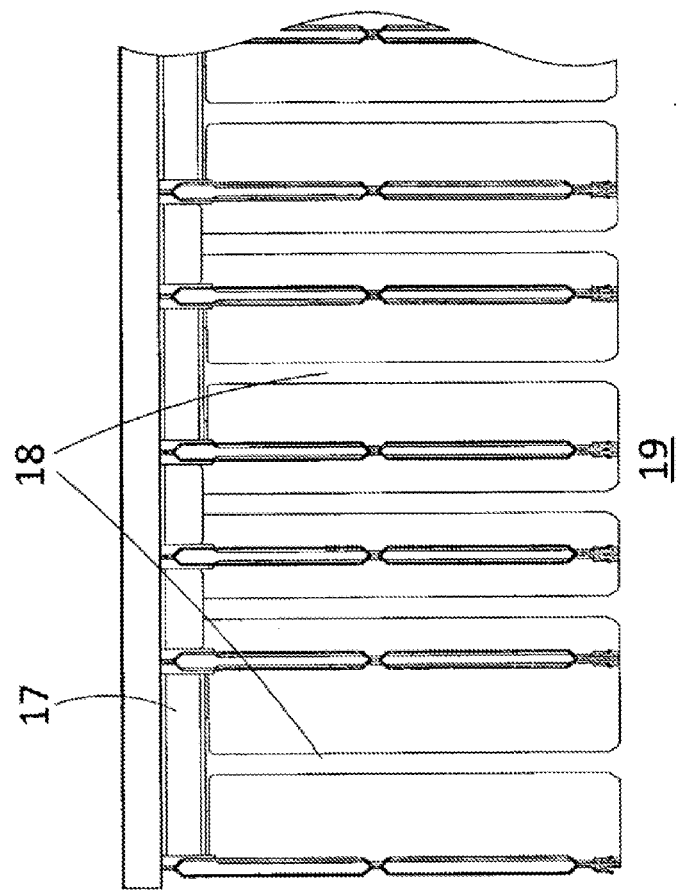
FIG. 58 shows a top view of the detail of FIG. 57.
Figure 57:
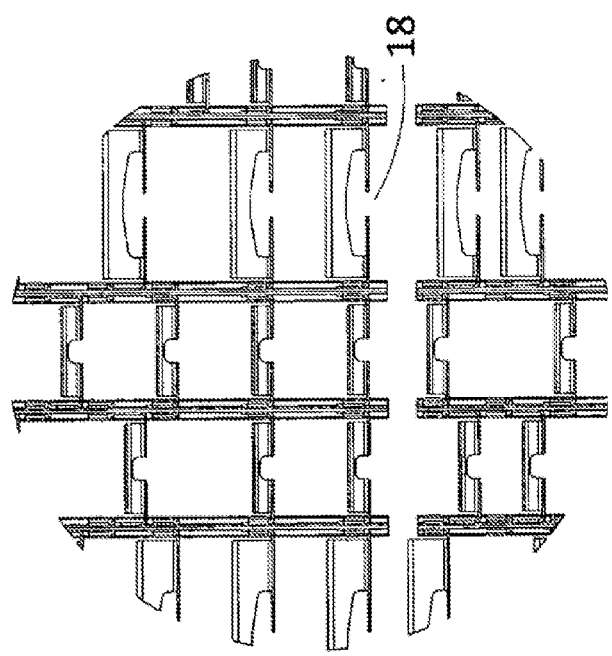
FIG. 57 shows a detail from the front of a rack of bins forming part of a storage apparatus according to an implementation disclosed herein.

A back end storage bin rack such as that shown in FIGS. 37-39 may be implemented with one standard bin size or, as shown in FIGS. 57-58, as a combination of different bin sizes enabling packages of diverse shapes and sizes to be stored. In addition, the storage bins may hold standard or non-standard sized pill bottles or boxes or other medicaments such as bulk medication storage containers, bandages, etc. Some or all of the storage bins may be located in a zone of the bin rack which is at room temperature, while others may be located in a controlled temperature section such as a refrigerated zone for proper storage of medicaments that are prone to deterioration at room temperature. If desired, a reconstitution, mixing and/or compounding bulk medication storage container can be present in an over-large bin, the container housing one or more elements to be picked by the pick head.

At the time of a package pick by the control system, the package characteristics are known because each package is measured and its dimensions recorded in the course of the package being serialized and put into inventory in a selected bin of the bin rack. Also recorded are any or all of the package's weight, shape, moment arm, and other particulars pertaining to the location and nature of the package and each of these can be used in the package handling control algorithm.

As shown in FIG. 41, sensors 50 at the pick head 20 sense the size of the package that has been picked to determine that a single package has been picked and to determine that there have been no common errors such as a stuck pick, where the package sits in place due, for example, to slipperiness, or a double pick, where two packages in close proximity are either tangled or stuck together. The control system, using input from the sensors and specific data for the package being picked, determines likely errors and initiates appropriate control maneuvers to try to overcome a problematic pick. Obviously, characteristics of the packages other than or in addition to size can be sensed by sensors incorporated in the pick head. Such characteristics can include, for example, shape and/or weight.

An alternative design of platform and drive is shown in the implementation of FIG. 50-52. The platform 32 is fixed to one end of a spool 52 of actuator tape 54. The tape is a heavy duty version of retracting tape rule. As is known in the tape rule art, the actuator tape has a curved lateral profile. This allows the tape to be readily bent in one direction to allow compact storage on the spool 52 when the spool is wound up but resists bending in the opposite direction whereby it can drive the platform 32 and a medicament package supported by the platform in a pick or load operation when the spool is unwound. The platform 32 is somewhat narrower than the platform of the FIG. 44 implementation and has an end region formed with a tapered blade 58 with a cam face 42 and an abutment face 44 having the same function as the cam and abutment faces, 42, 44, of the projection 40 in the FIG. 44 implementation. This particular implementation can be used with a bin without a slotted floor. In a pick operation, after the pick head 20 reaches the desired XY position, the spool 52 of actuator tape is driven to unwind the tape 54 so that the platform 32 is driven rearwardly towards the selected bin.

As best shown in FIG. 52, the platform 32 is brought to a position where the leading edge of the tapered blade 58 is aligned with the upper surface of floor of the selected bin 12 so that further rearward motion of the platform acts to insert the tip of the blade between the bin floor 16 and the foremost package stored in the bin. As the spool is further unwound, the tapered blade 58 is driven rearwardly along the floor 16 of the bin with the cam face 42 operating to raise the desired package and with the platform 32 supported on the floor of the selected bin. The desired package 46 is prevented from moving rearwardly in the bin 12 either by the back wall 17 (not shown) or by a next adjacent package in a row of such packages which is prevented from rearward motion by wall 17. With the rearward motion of the desired package prevented or halted, the desired package rides up and over the cam formation 42 onto the platform 32 as the platform is driven rearwardly into the selected bin. Subsequently, the platform is withdrawn from the bin rack as the spool 52 is rewound so as to withdraw the desired package 46 which is then supported by the platform. The abutment face 44 acting on the desired package assists in the withdrawal of the package if the force of engagement between the platform upper surface and the desired package is insufficient to drag the package out of the bin rack, or if minor jamming occurs and must be overcome.

In contrast to the FIG. 44 implementation, the FIG. 50 implementation can be readily utilized for loading packages into selected bins 12 as an alternative to manual loading. In the loading process, a package is loaded onto the platform 32 with the pick/load head 20 located at a receiving station in the dispensary kiosk. The pick/load head is then operated to bring the platform and the package supported by it to the selected bin. The spool 52 is then unwound in an operation similar to that taking place in the pick process. As the platform 32 moves rearwardly into the selected bin 12, the supported package is driven as far as is permitted depending on what other packages are already stored in the bin. Subsequently, the tape spool is reversed to retrieve the platform from the selected bin, but only after a barrier not shown) mounted on the pick head 20 is moved to a position at which the platform 32 can exit the selected bin, but any package supported on the platform is preventing from being dragged or driven out of the bin.

Figure 54:
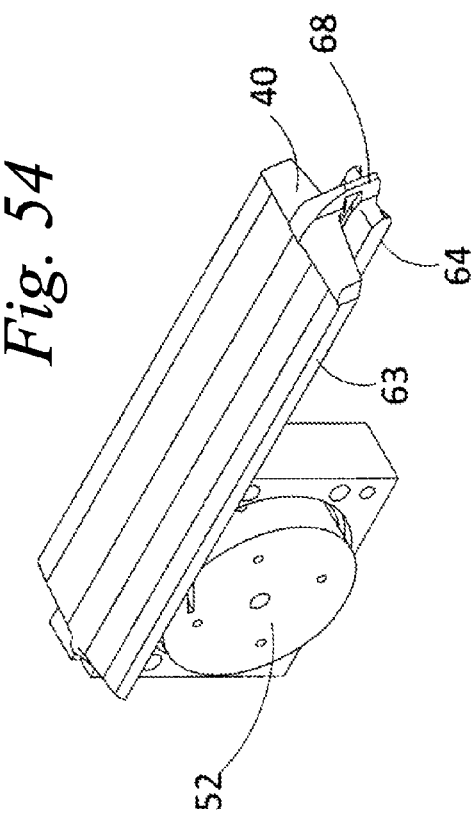
FIG. 54 is a perspective view of a platform and spool arrangement forming a part of the FIG. 53 embodiment.
Figure 55:
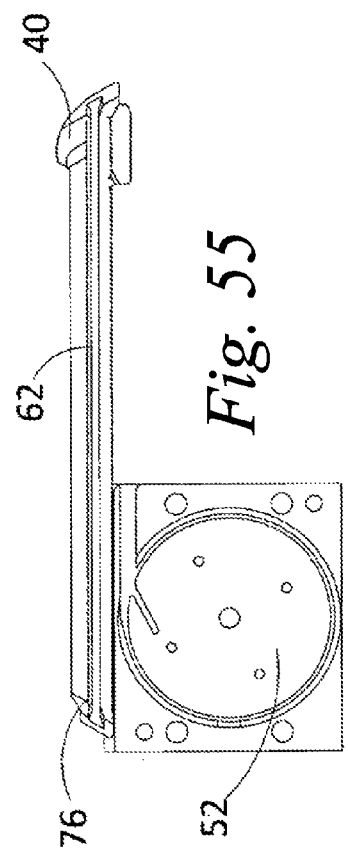
FIG. 55 is a side view of the platform and spool arrangement of FIG. 54.
Figure 53:
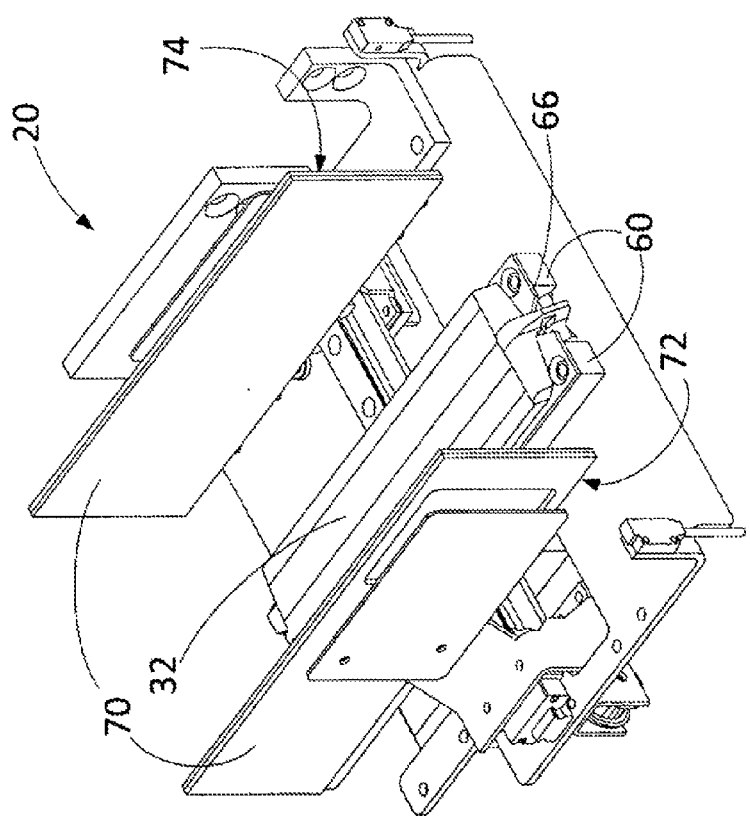
FIG. 53 is a perspective view of a pick head according to a further implementation disclosed herein, the arrangement shown with a platform forming part of the pick head in an unextended condition.
Figure 56:
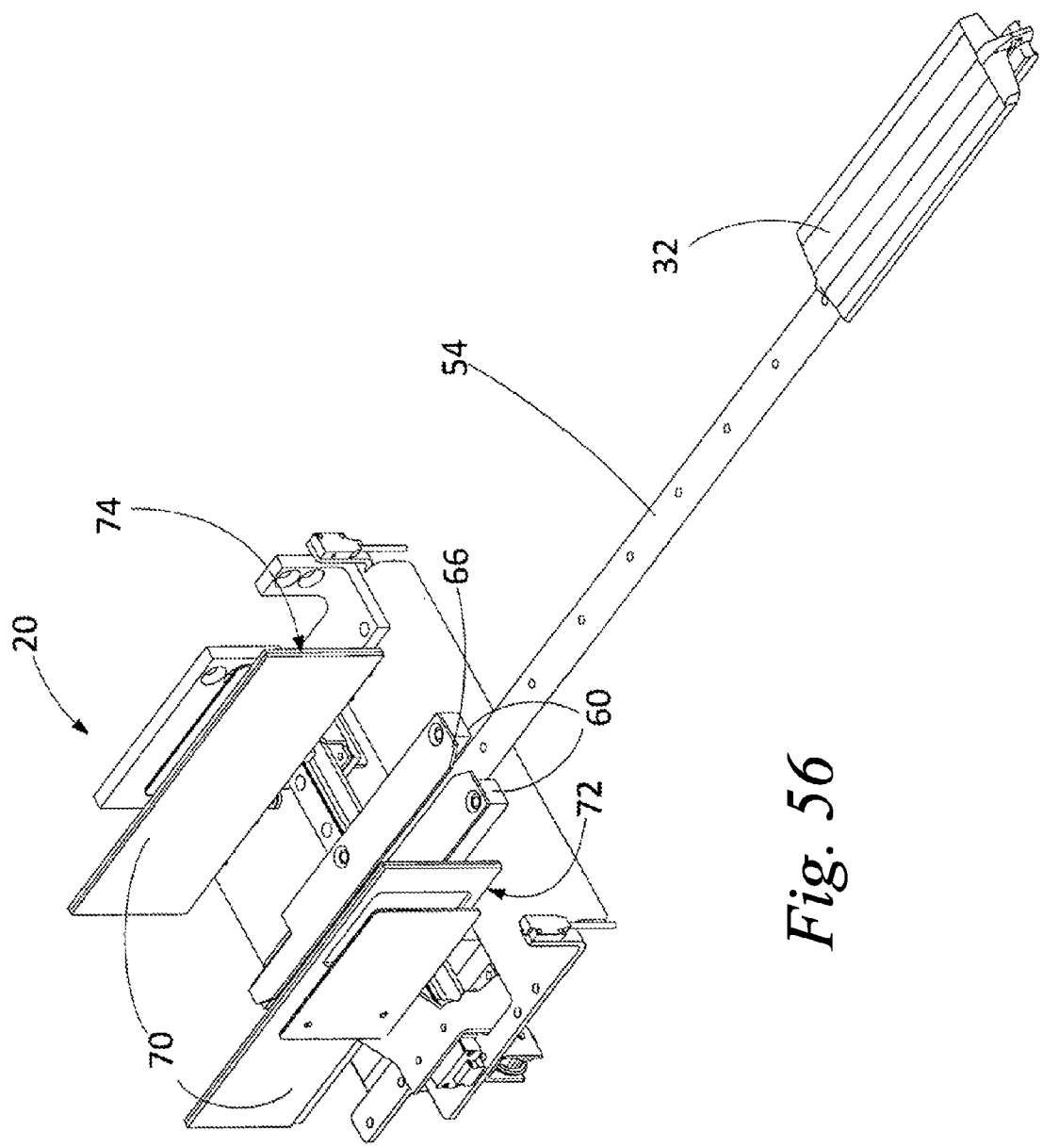
FIG. 56 is a perspective view corresponding to FIG. 53 but showing the pick head in an extended condition.

A variation of the FIG. 50 implementation is shown in FIGS. 53-55. Like the FIG. 50 implementation, the pick head 20 uses a spool drive 52 as shown in FIGS. 54-55. Tape at the pick head inboard end is confined and supported by two retainer plates 60 as the spool 52 is unwound and, similarly to the FIG. 50 implementation, is supported by the engagement of the platform 32 sliding onto the floor of a selected bin at the tape outboard end. In the FIG. 53 implementation, the platform 32 combines features of the FIG. 50 and FIG. 44 implementations. Thus the platform 32 is adapted for use with a storage bin having a front to rear slot (not shown) of the sort described with respect to the FIG. 44 implementation. The platform has an integral web part 62 extending down from a main body part 63 of the platform, and a rail 64 extending laterally on either side of the web part. The web part moves within the bin floor slot as the platform 32 is driven into and out of the bin rack. The main body part 63 of the platform slides over the upper surface of the bin floor and is supported by it, while the rail 64 slides along the undersurface of the bin floor. As the platform nears its home station position in the pick head, the web part 62 moves between the retainer plates 60 with the rail under edge flanges 66 of the retainer plates.

The platform has a cam formation 40 which projects above the bin floor but also has narrower central section 68 which, in use, extends down into the bin floor slot. A particular value of the cam formation is that the leading end of the platform 32 lifts and slides under any package that is very thin or that has a thin layer lying adjacent the bin floor which is encountered by the platform as it moves into the storage rack.

As mentioned with respect to the FIG. 50 implementation, at certain junctures in the package picking and loading procedures, it is desirable to withdraw the platform 32 without withdrawing a package that is supported on the platform, or without withdrawing such a package any further than a predetermined position. As shown in FIG. 53, a barrier arrangement is provided by spaced plates 70 which can be driven perpendicularly to the pick head Z-axis to increase and decrease the spacing of the plates.

In operation, during a package loading procedure, the platform supporting the package to be loaded is driven into the bin rack. Once the package is in place, the plates 70 are driven to reduce their spacing and the platform 32 is withdrawn from the bin rack. The platform slides under lower edges 72 of the plates towards its home station in the pick head while the package which has been loaded in the selected bin and hitherto supported by the platform is blocked from exiting the selected bin by vertical edges 74 of the plates 70. The platform has a radiused rear formation 76 to reduce the risk of jamming of a package against the barrier as the platform 32 travels out of the bin rack. The plates have adjunct functions to both grip a package which has been picked from the bin rack when the picked package reaches a desired position in the pick head and also to centre the package in the pick head.

As previously mentioned, packages may be stored in a bin rack either with one package in a bin, or with a row or stack of packages in a bin. The manipulation of a row of packages has already been described with reference to the illustrated implementations. In the case of a vertical stack of packages, the pick head platform and a barrier of the sort described with respect to FIG. 53 can be used to pick and extract the lowermost package in the stack, allowing upper members of the stack to drop. Similarly, a combination of camming and abutment formations together with a barrier of the sort described platform can be used to enable a package to be loaded under a resident stack of packages within a storage bin. In addition if it is desired to pick or place a package in an intermediate position in a stack or row, the pick head can be used to pick and temporarily park packages from a stack or row in an adjacent bin until a desired package is exposed for picking or until a desired location is exposed for loading.

Although in various implementations described herein, the bins are located in a rack as an array of rows and columns, other arrays are possible such as a radial array or a diagonal array. In such arrays, the rectangular form of bin may not be optimal and alternative bin shapes may be of advantage. In such alternative implementations, the lower wall or floor of the bin may not extend horizontally or may not extend horizontally over its full extent. In addition, while it is convenient to have a pick head that moves in a Z direction in relation to a bin rack generally mounted in an XY plane, the pick head drive may be implemented to effect a movement of the pick head into the bin rack in a locus which is not linearly along a z-axis. For example, the pick head is moved over an arcuate path or packages are held in one position and then twisted into a desired position as they are loaded or withdrawn from a storage bin.

In the implementations described, packages in a bin are acted upon by gravity and this interaction of the stored packages with the platform upper surface, the abutment edges and cam formations permits a ready and simple implementation of platform entry and exit to effect picking and loading of a package relative to a selected bin. While the effect of the packages' own weight is convenient, the effect of gravity may be replaced by or supplemented by having a stored package acted upon by a bias such as a spring bias. Such a bias can be applied permanently while the package is in a bin or at the pick head or may be acted upon in the course of platform movement into and out of the bin rack. In such an arrangement, cam and/or abutment formations may act in a manner similar to the illustrated implementations, but the package to be picked or loaded is moved against and by the action of the bias as opposed to or in addition to gravity.

Figure 59:
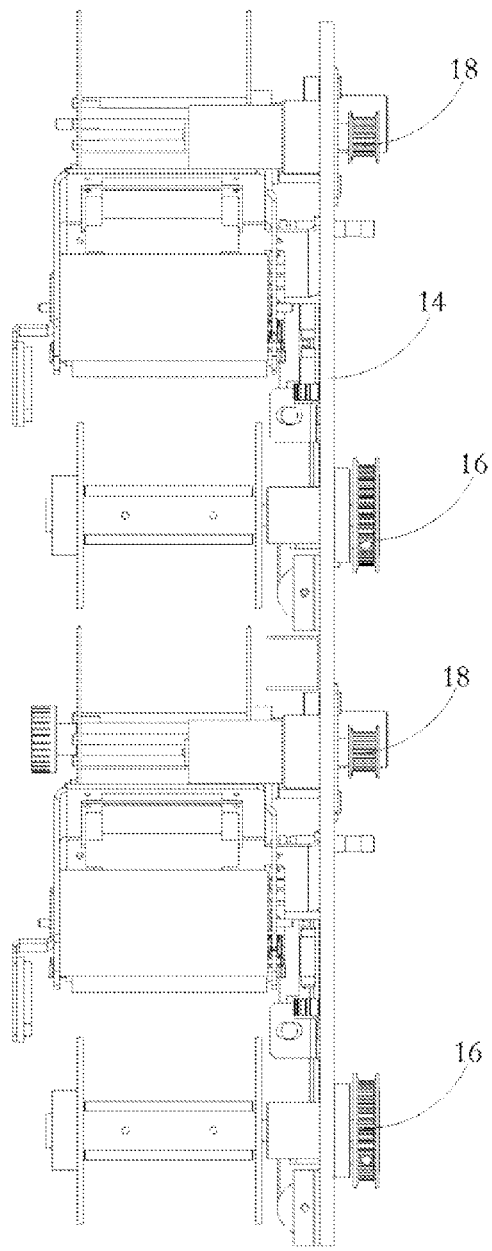
FIG. 59 is a side view of a labeling unit according to one implementation disclosed herein.
Figure 60:
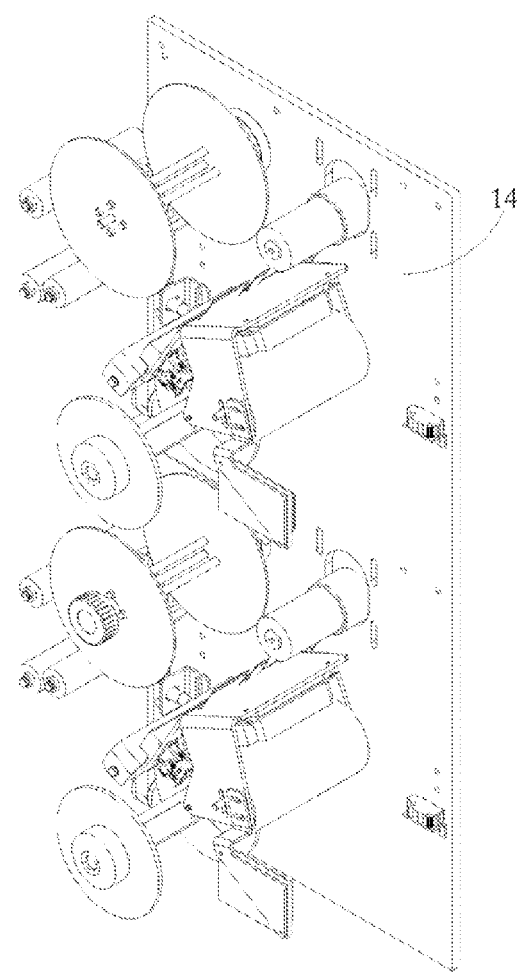
FIG. 60 is a front perspective view from above of the labeling unit of FIG. 59.
Figure 61:
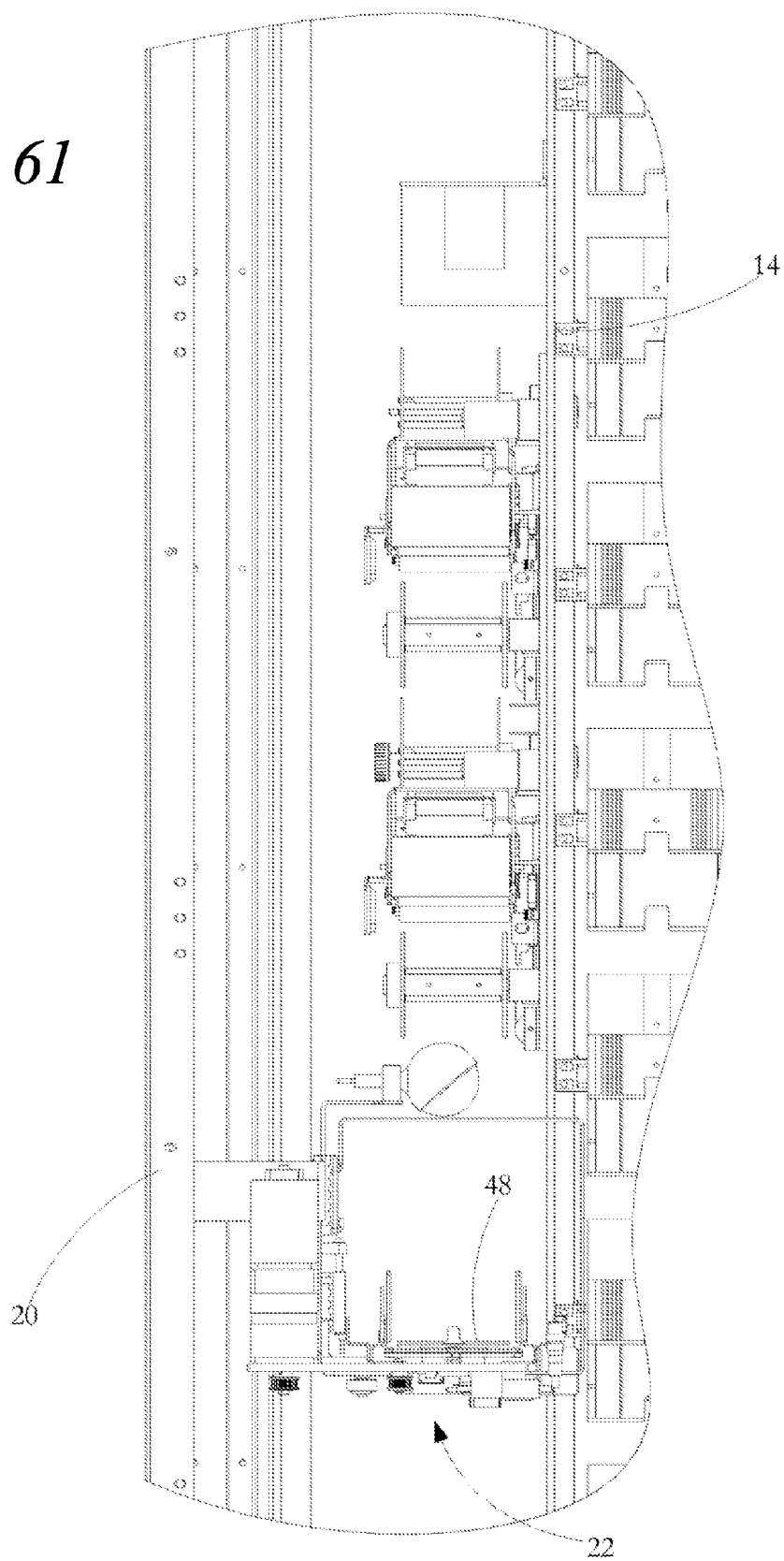
FIG. 61 is a partial side view of part of a medicament dispensary kiosk showing the labeling unit of FIG. 59 mounted with a frame of the kiosk.

In yet another implementation, and referring in detail to FIGS. 59-60, a package labeling unit 10 is shown which has upper and lower labeling modules 12. In normal mode, one of the modules is in use and the other module is redundant pending breakdown or other interruption in operation of the one module. Elements of the labeling modules 12 are mounted on a mounting plate 14. As shown in FIG. 59, rotatable elements of the labeling module are fixed to pulleys 16 which are mounted on a reverse face of the mounting plate and are driven by bands (not shown) from a motor 18. As shown in FIG. 61, the labeling unit 12 is mounted within a support frame 20 of a medicament dispensing kiosk. Also mounted in the frame is a pick head of the sort described in co-pending U.S. patent application Ser. No. 12/503,989, filed on Jul. 16, 2009, titled "Method and Apparatus For Picking A Package From a Dispensing System," which is herein specifically incorporated by reference.

Figure 62:
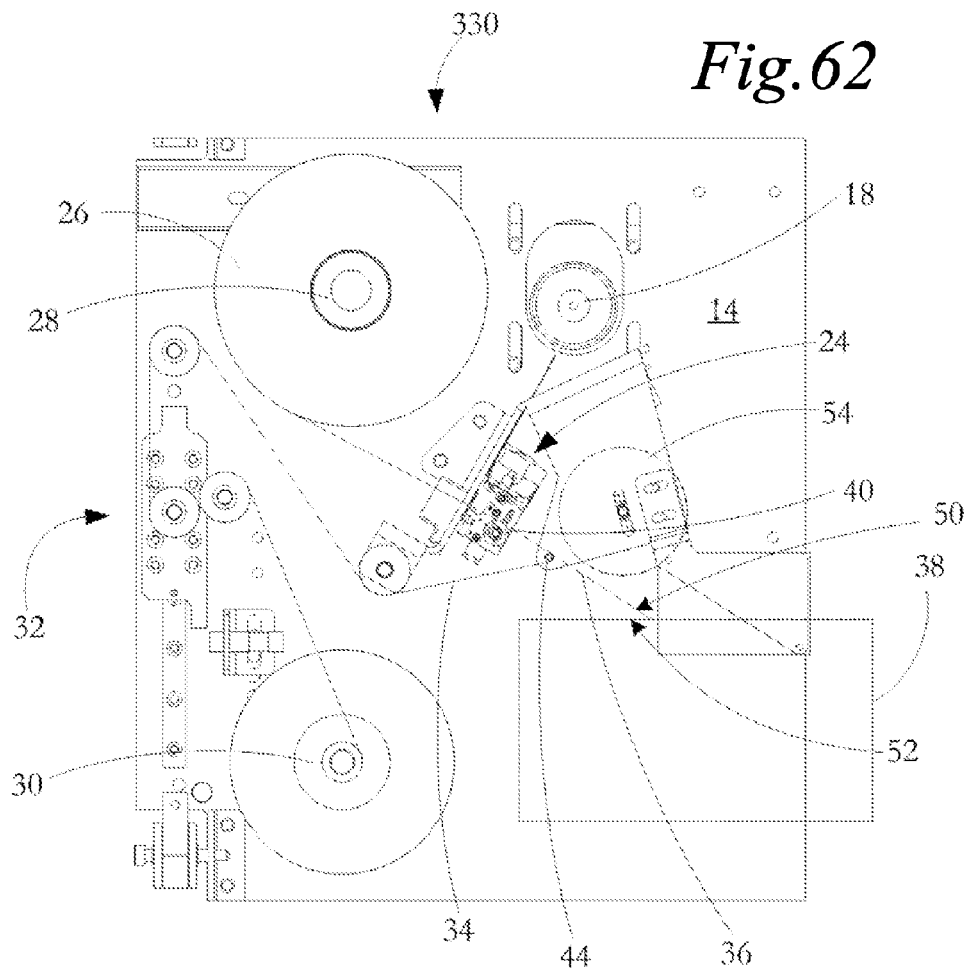
FIG. 62 is a front view of part of the unit of FIG. 59 to a larger scale.
Figure 63:
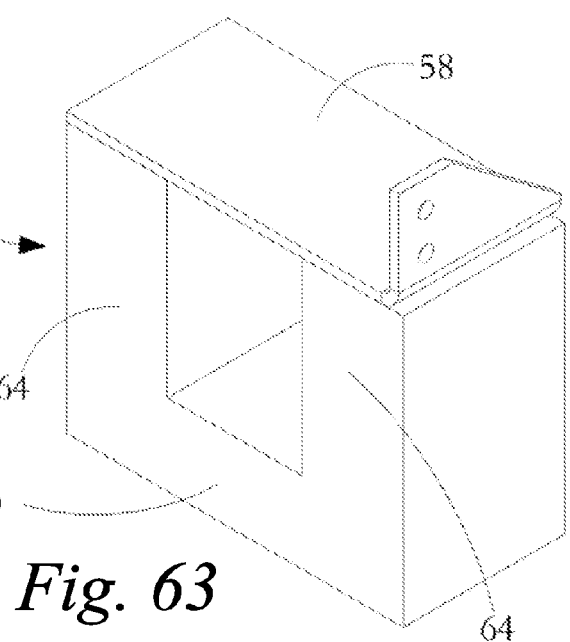
FIG. 63 is a perspective view of a tamp block used in a method according to one implementation disclosed herein.

As shown in greater detail in FIG. 62, each labeling module 12 has a printer 24, label stock 26 wound from a supply reel 28, a take-off reel 30 associated with a tensioner device 32, and the motor 18. The label stock 26 is in the form of a release liner or backing 34, with labels 36 self-adhering to the liner along its length.

The labeling module is used to apply a label to a medicament product container or package 38 which is transported to the labeling module 12 using the pick head. In use, label stock 26 is pulled off the supply reel 28 by a drive wheel 40 in the printer 24. Within the printer, the label stock is halted and desired medicament identifying data is printed onto a presented label before the printer wheel 40 further advances the label stock 26 in preparation for the printed label 36 to be applied to the container 38. The label can alternatively be printed while still in position as is known in the art. As the label stock 26 exits the printer 24, the printed label 36 continues to adhere to liner 34, and the take-up reel 30 and tensioner device 34 pull the liner around a small diameter roller 44 so as to take up the liner 34 at a rate related to the throughput of the printer 24.

The label 36 is made from paper or plastic that is stiffer than the liner 34 to which it adheres on the supply reel 28. This results in the label 36 separating from the liner 34 as a result of its movement around the small diameter roller 44. The label 36 is also sufficiently stiff that it adopts a suspended position as shown in FIG. 62 as it progressively separates from the liner 34. For this purpose, the label 36 is of material that is sufficiently stiff as effectively to prevent the label from sagging under its own weight from edge to edge along its longest side. The label stock 26 advances to a point where about ⅞ of the label length is detached from the liner 34 so that the label is suspended in preparation for a subsequent stage in the labeling process. It will be appreciated that whereas, in this implementation, the label 36 is of uniform stiffness over its area, in an alternative implementation, the label can be locally stiffened as, for example, by one or more thicker regions, whereby the stiffness required both for the separation from the liner and for the temporary suspension of the label are achieved.

The pick head is then driven to pick a medicament container 38 to be dispensed by the apparatus and to raise the container to a desired level where a platen forming part of the pick head and supporting the container moves in a horizontal direction to bring the container to the position shown in FIG. 62. At this point, the container 38 is located under the suspended label 36 with a combination of sensors and feedback ensuring that a front edge 50 of the label is aligned with a pre-selected contact start point 52 on the product package.

In a subsequent stage of the labeling process, the pick head drives the package 38 upwardly against a conformable cylindrical, first tamp block 54 of polyurethane foam, this movement acting both to initiate a "tacking" of the self-adhesive label 36 to the package 38 and to dislodge the last part of the suspended label 36 from the liner 34. In an alternative implementation, the "tacked" label is removed from the liner by moving the package horizontally in synchronism with movement of the printer wheel 40.

Figure 64:
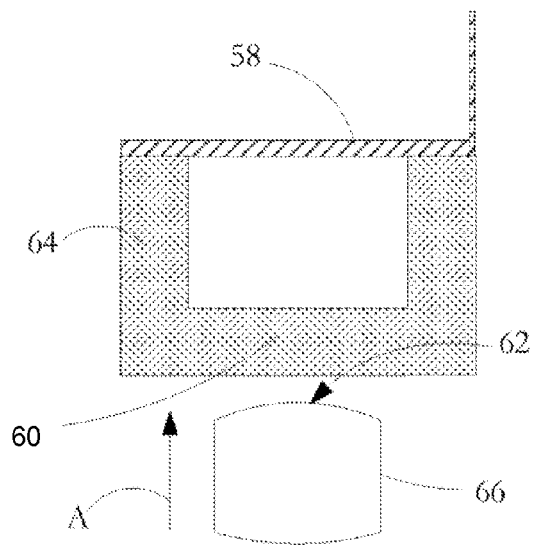
FIGS. 64 to 66 show a sequence in the operation of the tamp block of FIG. 63.
Figure 65:
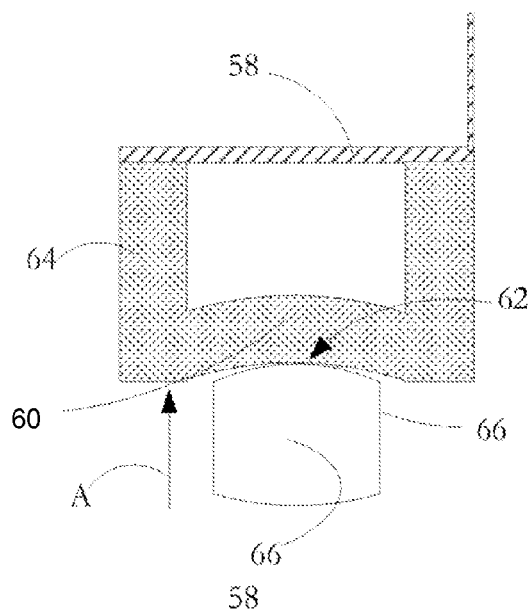
Figure 66:
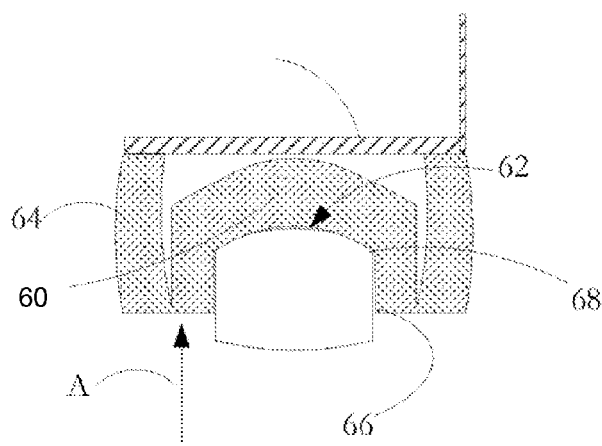
Figure 67:
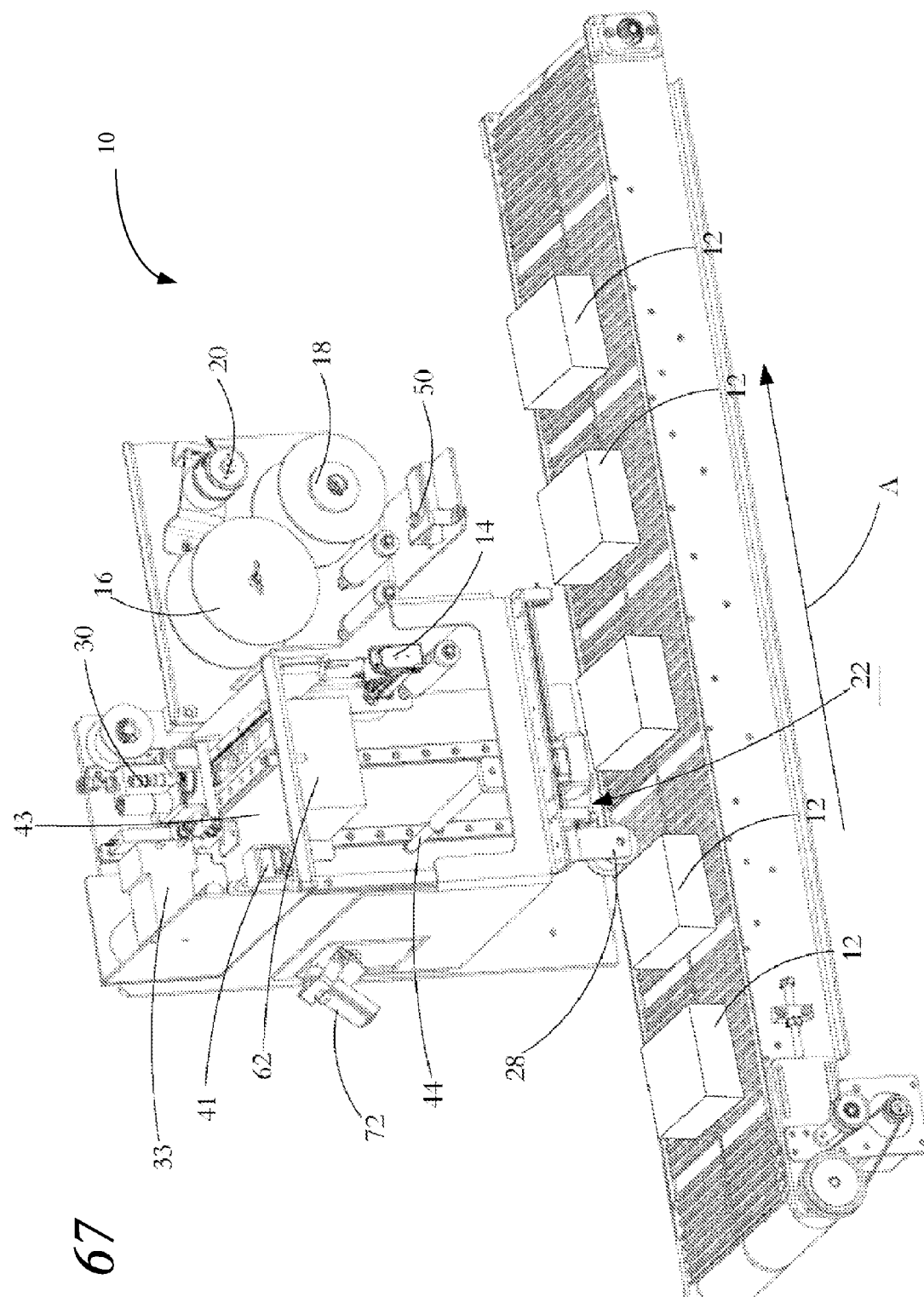
FIG. 67 is an isometric view of a labeling station according to an implementation disclosed herein.

The medicament container 38, with label attached, is then further raised by the pick head to bring the container 38 with the label side up, into contact with the second tamp block 56 formed from conformable polyurethane foam, the second tamp block 56 being shown in FIG. 62 and in FIGS. 64-66. The second tamp block 56 is generally of U shape and has a rigid constraining bar 58 mounted to the mounting plate 14 and extending between and fixed to the two uprights of the U.

In use, the package container 38 with label 36 tacked to at least a central part of the container surface is brought against a cross-piece 60 of the U tamp block as shown in the operational sequence of FIGS. 64-66. The uprights of the U are anchored by the constraining bar 58 and the cross-piece 60 of the U is relatively thin and flexible. Consequently, when the product container 38 is moved in the direction of arrow A, the relatively thin and flexible U cross-piece 60 firstly conforms to an upper surface 62 of the package container 38 as shown in FIG. 65 so that a part of the label is sandwiched between the cross-piece 60 and the front of the package. Then, in response to further upward movement of the platen 48 in the direction of arrow A, as shown in FIG. 66, the tamp block 56 is squeezed resulting in U uprights 64 being forced alongside container sides 66. Because the U uprights 64 are prevented from further translational movement, they buckle and fold as shown in FIG. 66 and, in so doing, deform to embrace at least a part of the respective sides of the package container so as to fold the label edges into adhering contact with both the sides 66 and corners 68.

Dimensions and materials are selected so as to direct pressure to contact the label to all intended parts of the package and to apply sufficient pressure to activate the contact sensitive adhesive. Because the size and shape of the package are known to the pick head control means, accurate label placement is possible with this method, with high reliability and repeatability.

It will be appreciated that the first and second tamp blocks, 54 and 56 respectively, can be combined if desired, whereby a first part of the movement of the container 38 relative to the combination tamp block is to tack the label 36 to the package, and then a subsequent part of the movement is to effect the label wrapping and application described previously. It will be appreciated also that alternatives to the U form of tamp block are possible. Thus O-form and H-form blocks can, for example, be configured to provide the relative translational movement and the block deformation to apply the label to the front and sides of a package.

In addition, while, conveniently, the tamp block is formed of a single cut or molded piece of material, the parts of the tamp block that are used respectively for the front tamp and the side tamp can be separate but joined by a mechanical articulation. It will be appreciated that in one implementation, the movement of the product container relative to the tamp block to apply an adherent label to the front and sides of a package is a single unidirectional movement of the container. However, the movement can alternatively be affected as intermittent actions. For example, a first translational movement of the tamp block or container to apply a label to the front of the package can be followed by a second movement where a combination of translational movement and twisting are used to apply parts of the label against the side walls.

In addition, it will be realized that the movement need not be unidirectional in nature. In a further alternative arrangement, the tamp block is moved while the product container, is maintained in a fixed position for the label application, or both the tamp block and the container are moved to effect the label application. It will be further appreciated that whereas the nature of the deformation of the tamp block to effect the pressure against the sides of the container occurs by the tamp block being squeezed between a clamping fixture at one side of the tamp block and the medicament package at the other side of the tamp block, other external fixtures can be positioned so as to limit the locations into which parts of the tamp block can be deformed to those required for the effective application of the label where required on the container and to the effective application of pressure at the contact locations.

Figure 68:
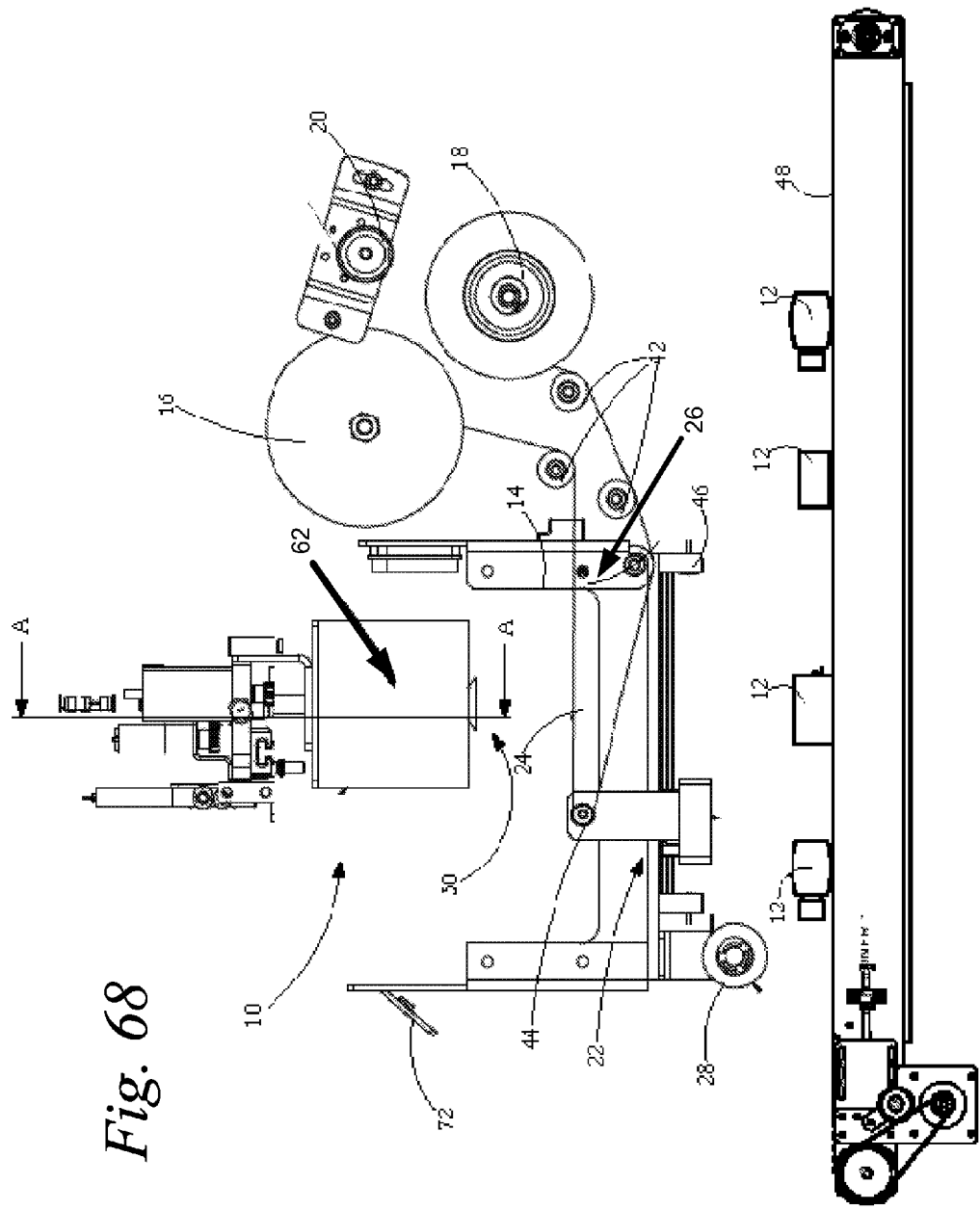
FIG. 68 is a side elevation of the labeling station of FIG. 67.
Figure 69:
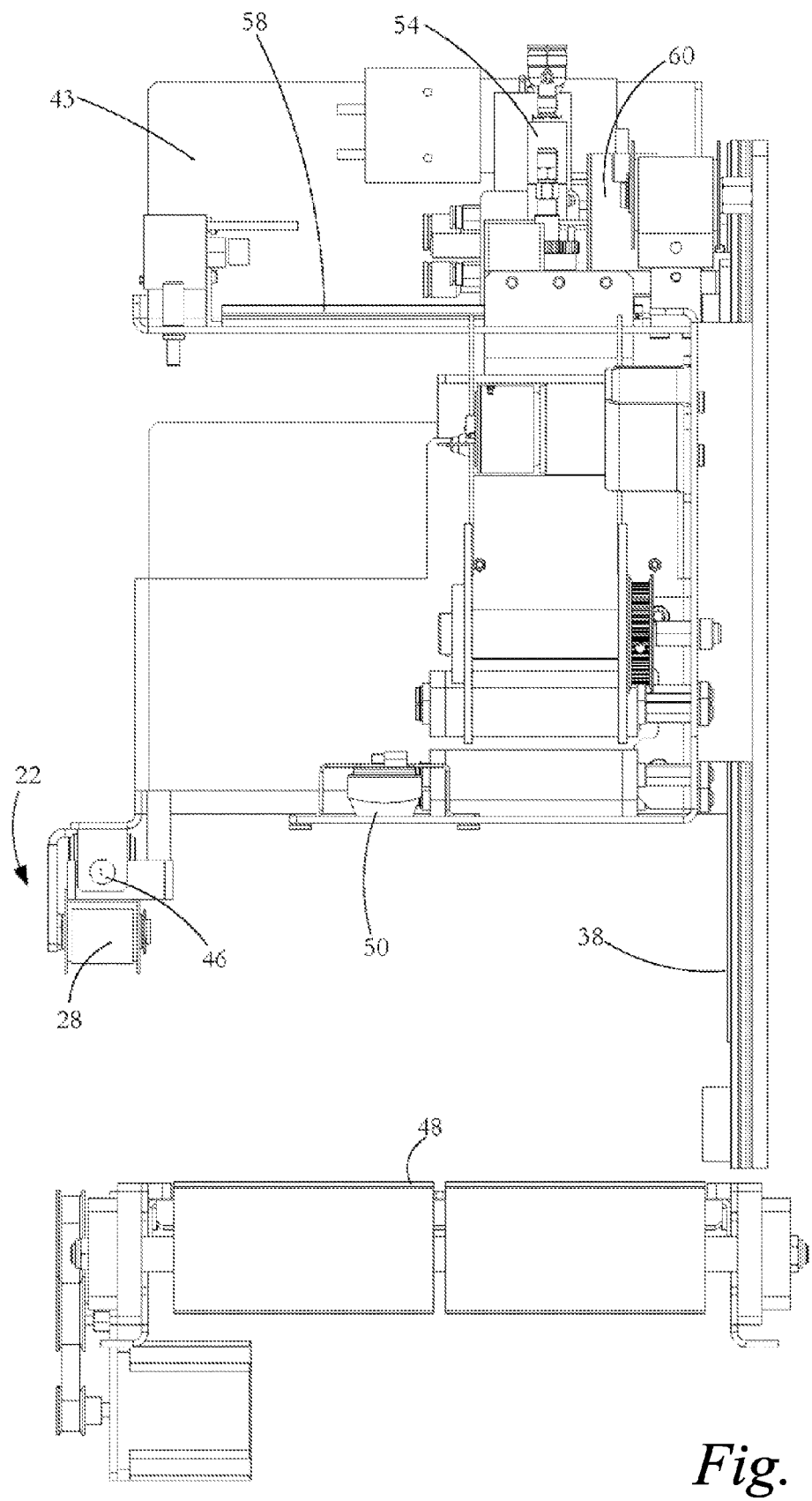
FIG. 69 is an end view of part of the labeling station of FIG. 67.
Figure 70:
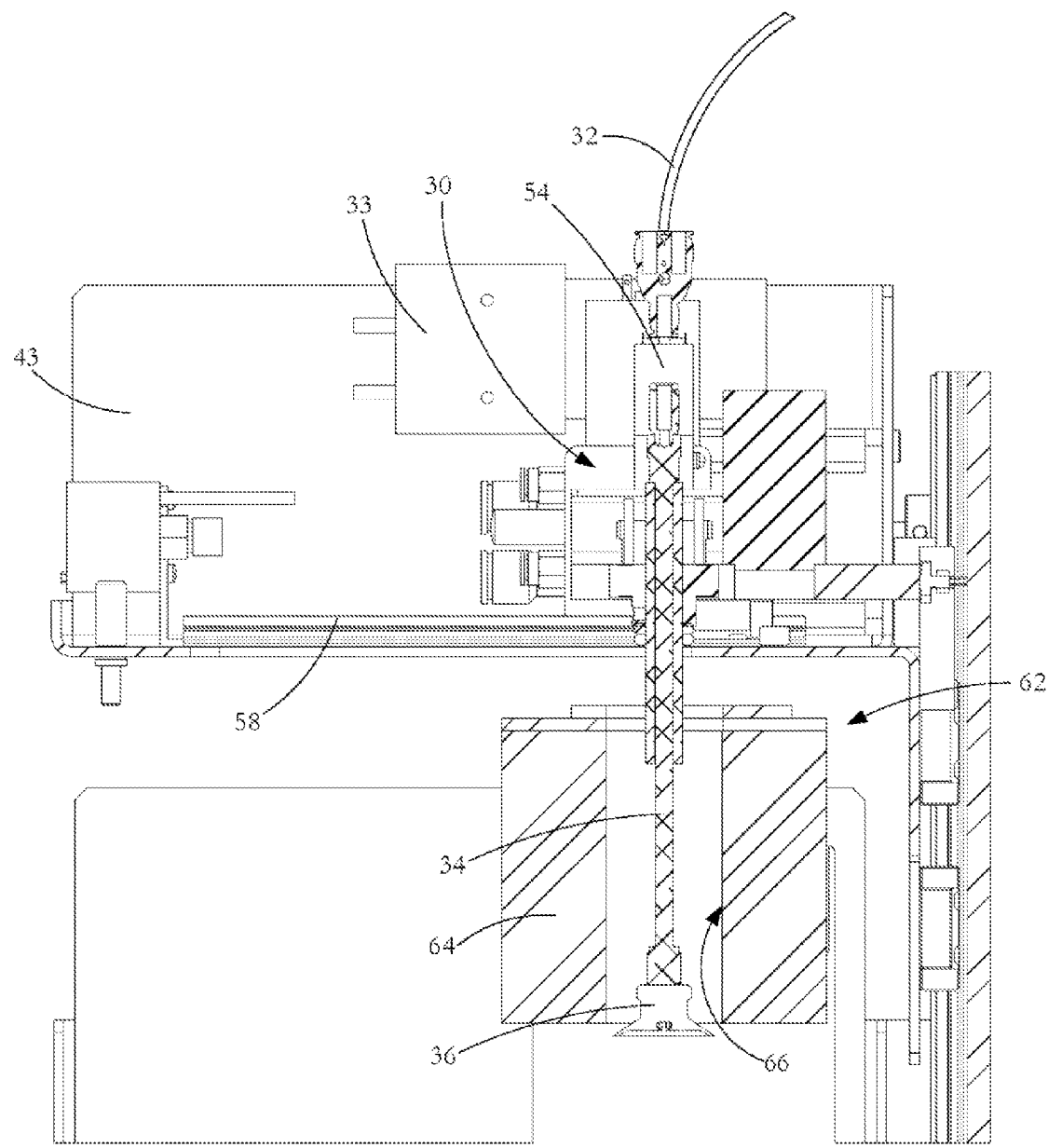
FIG. 70 is a sectional view on the line A-A of FIG. 68.

In yet another implementation, and referring in detail to FIGS. 67-74, a labeling module 10 is shown which is used to apply labels to medicament packages 12 as they are moved through a labeling station of a dispensing kiosk of the sort disclosed herein. The labeling module 10 has a printer 14, a supply reel 16 for supporting a roll of label stock, a take-up reel 18 driven by a motor 20, and a tensioner device 22. As shown in FIG. 68, the label stock is in the form of a web 24, the web consisting of a release backing, with a series of labels self-adhering to the backing along its length. The labeling module also includes a tamp assembly 62 and a suction device 30.

Figure 7:
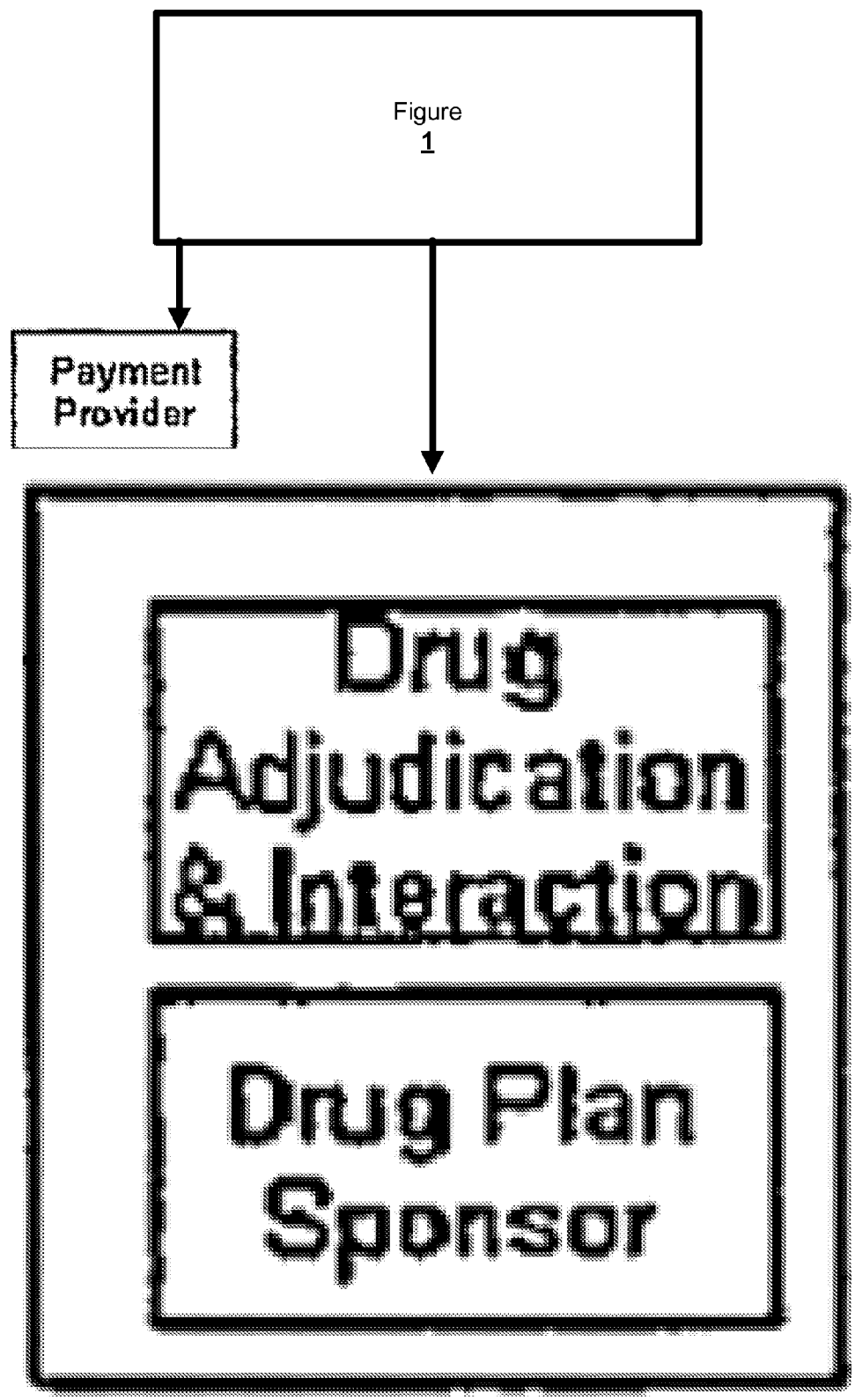
Figure 8:
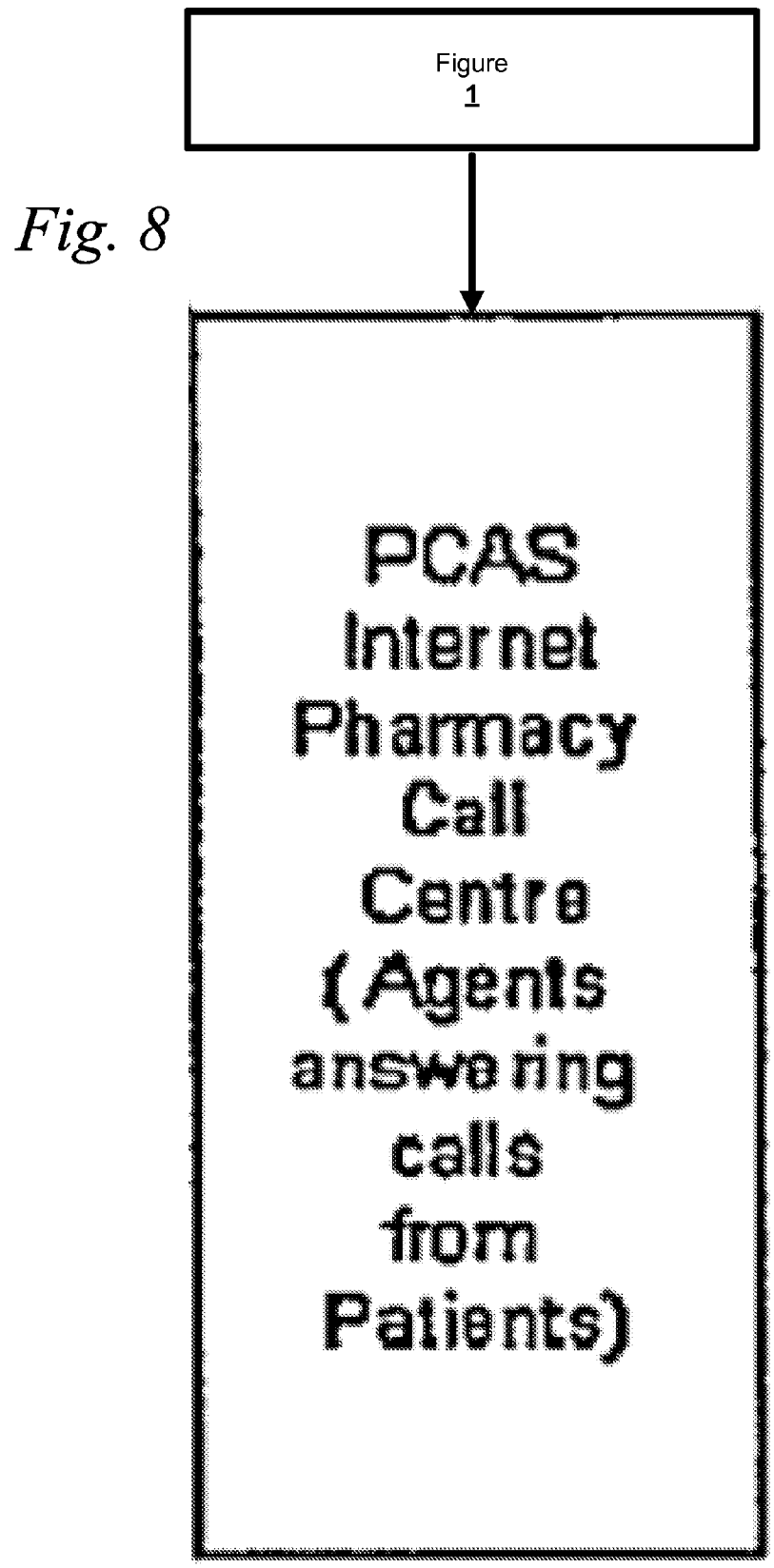
Figure 71:
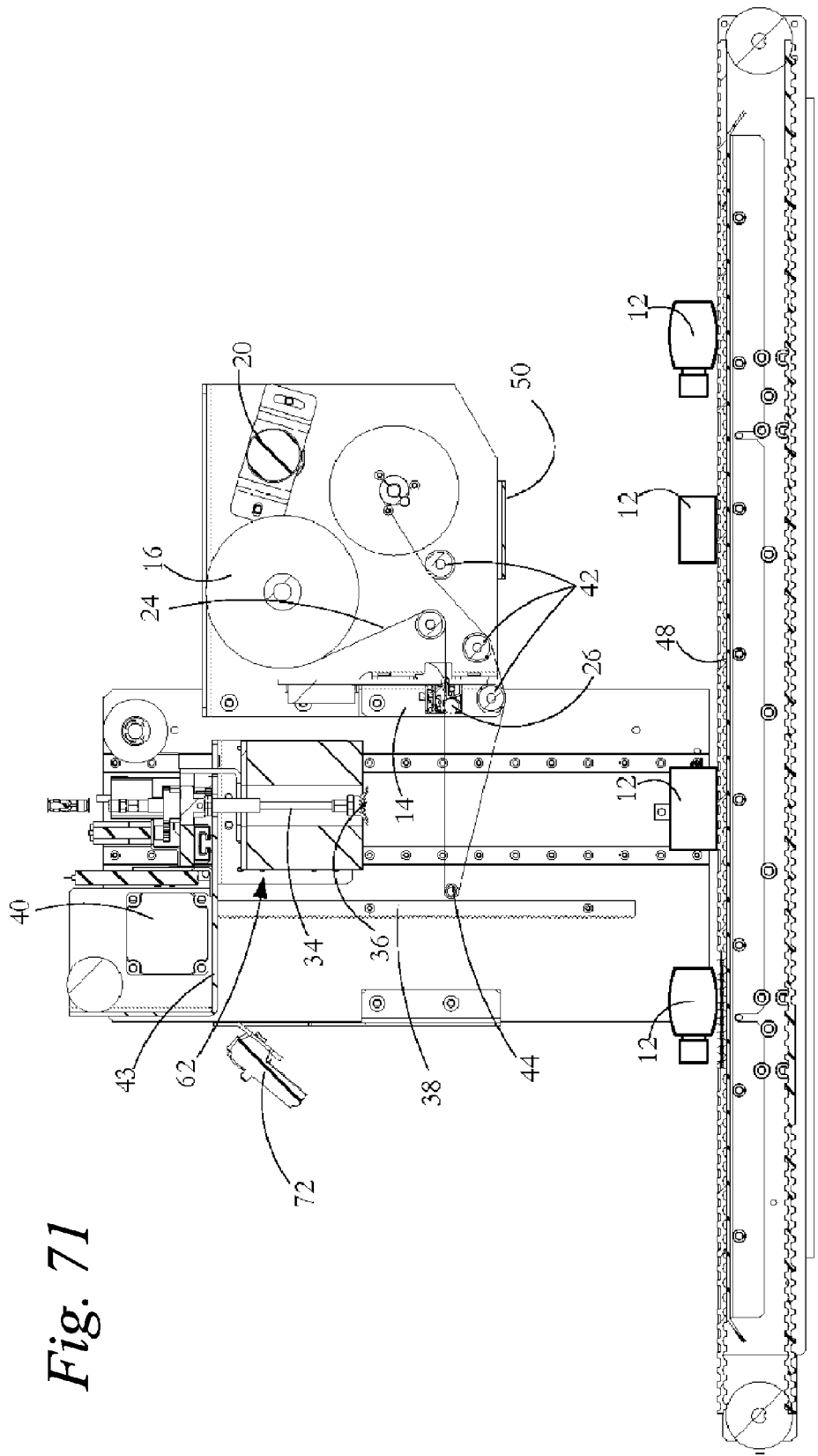
FIG. 71 is a side elevation corresponding to FIG. 68 and showing the position of elements of the labeling station in the course of a label printing process.
Figure 72:
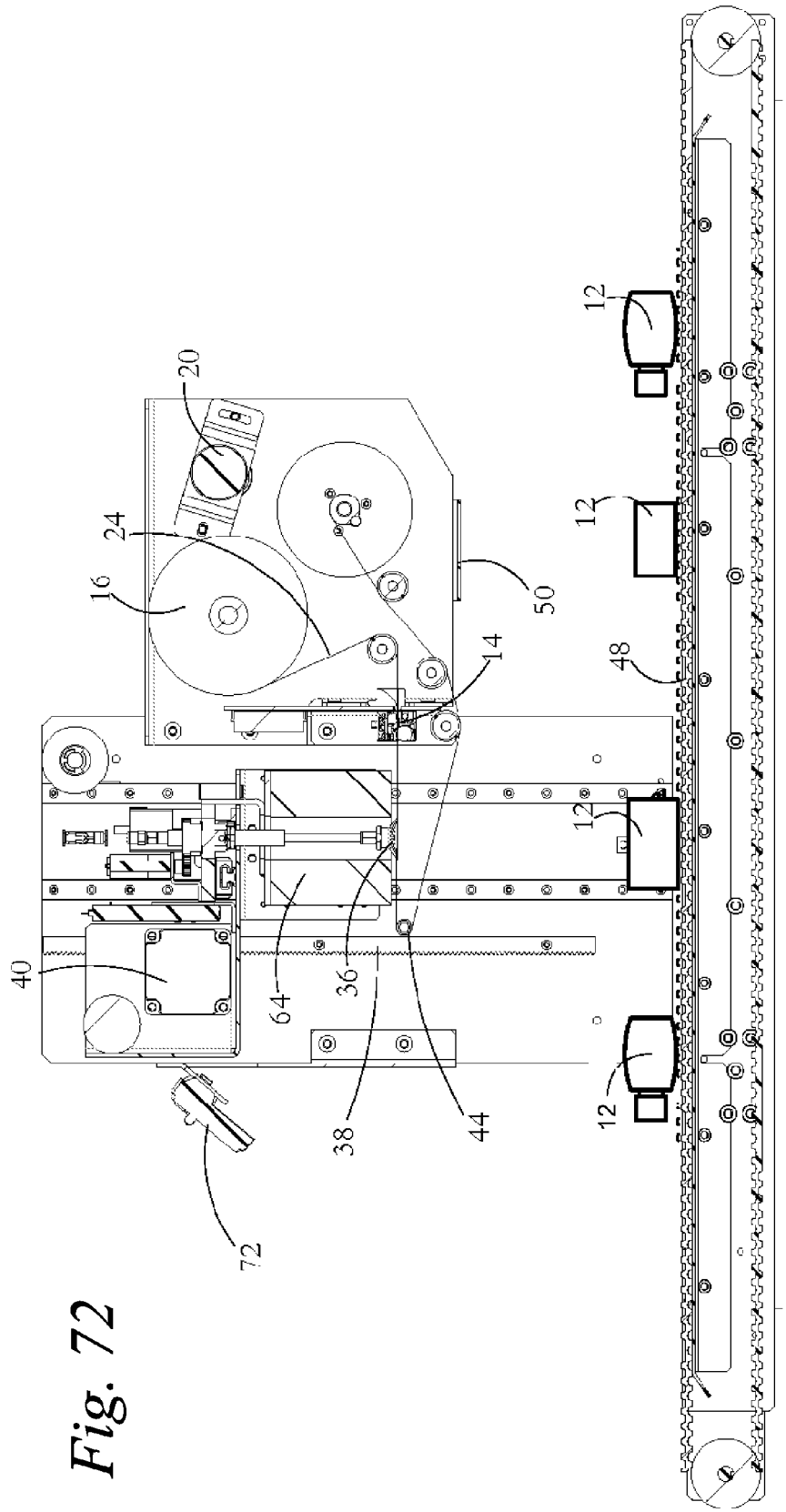
FIG. 72 is a side elevation corresponding to FIG. 68 and showing the position of elements of the labeling station in the course of a label pick-up process.

As shown in FIG. 71, the web 24 is pulled from the supply reel 16 by a drive wheel 26 forming part of a web advance mechanism in the printer 14. As the web passes through a slot in the printer, identifying data and other information related to the drug in a package to be labeled is printed on each presented label in preparation for the label being applied to the corresponding package 12. As shown in FIG. 68, as the web 24 exits the printer 14, a spring 28 forming part of the tensioner 22 retracts to pull the suspended part of the web towards the left as shown in FIG. 68. This brings the label that has just been printed to a position under a suction device 30 as shown in the part sectional view of FIG. 70. The suction device 30 includes a flexible tube 32 connected at one end to a vacuum pump 33 and at the other end to a rigid tube 34 which transmits a vacuum developed at the vacuum pump to a suction cup 36 mounted at the end of the tube 34. The tube 34 is mounted on a compound drive unit including a carriage 43 which is driven along a rail 58 (FIG. 70) by a stepper motor 60 to change the position of the tube along a first horizontal axis. Fixed to the tube 34 is a driven gear 52 (FIG. 7) which is driven from a DC motor 54 by a drive gear 56 (FIG. 7) to rotate the tube about its vertical axis. The drive unit also includes a rack 38 and a vertical position stepper motor 40 shown in FIG. 71 which are operable to effect vertical stepped movement of the carriage 43 and the tube 34 and tamp assembly 62 that are mounted on it. In use, when the label is suspended under the suction cup, the stepper motor is activated to lower the carriage until the suction cup at the end of the tube 34 reaches the tensioned web 24 as shown in FIG. 72, hereupon suction is developed at the web top surface to provide a suction grip to hold the web against the cup.

Figure 73:
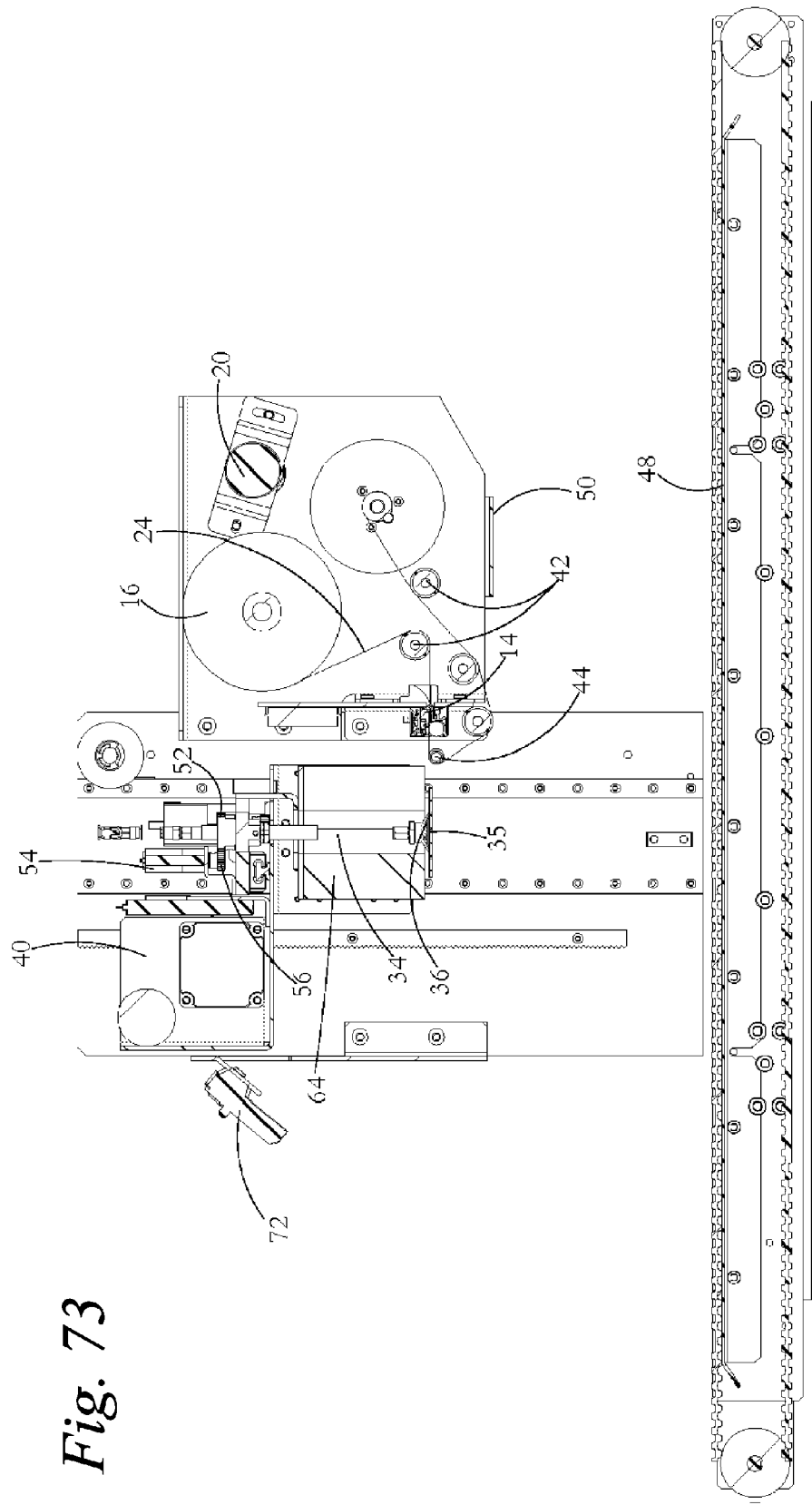
FIG. 73 is a side elevation corresponding to FIG. 68 and showing the position of elements of the labeling station in the course of a label stripping process.

When a required vacuum level is attained, a vacuum switch 41 is tripped to trigger drive of the take-up reel 18 to begin separation of the gripped label from its backing. As shown in FIG. 73, the web is driven around an assembly of rollers including guide rollers 42 and a retractable, small diameter, roller 44 forming part of the tensioner 22. As an advanced length of the web 24 is wound onto the take-up reel 18, the part of the web suspended at the tensioner roller moves to the right as the tensioner spring bias is overcome by the pulling force applied to the web 24 from the take-up reel. Label 35, because it is gripped at the suction cup 36, is prevented from moving with the suspended web and when the adhesive force between the gripped label and the backing is overcome, the label 35 is stripped from the backing.

To encourage separation, the labels 35 can be made from a paper or a plastic that is relatively stiffer than the backing to which they adhere. With such a structure, a label tends to separate progressively from the backing as the web 24 is fed around the tensioner roller 44 because the label is unable fully to conform to the shape of the roller.

Figure 74:
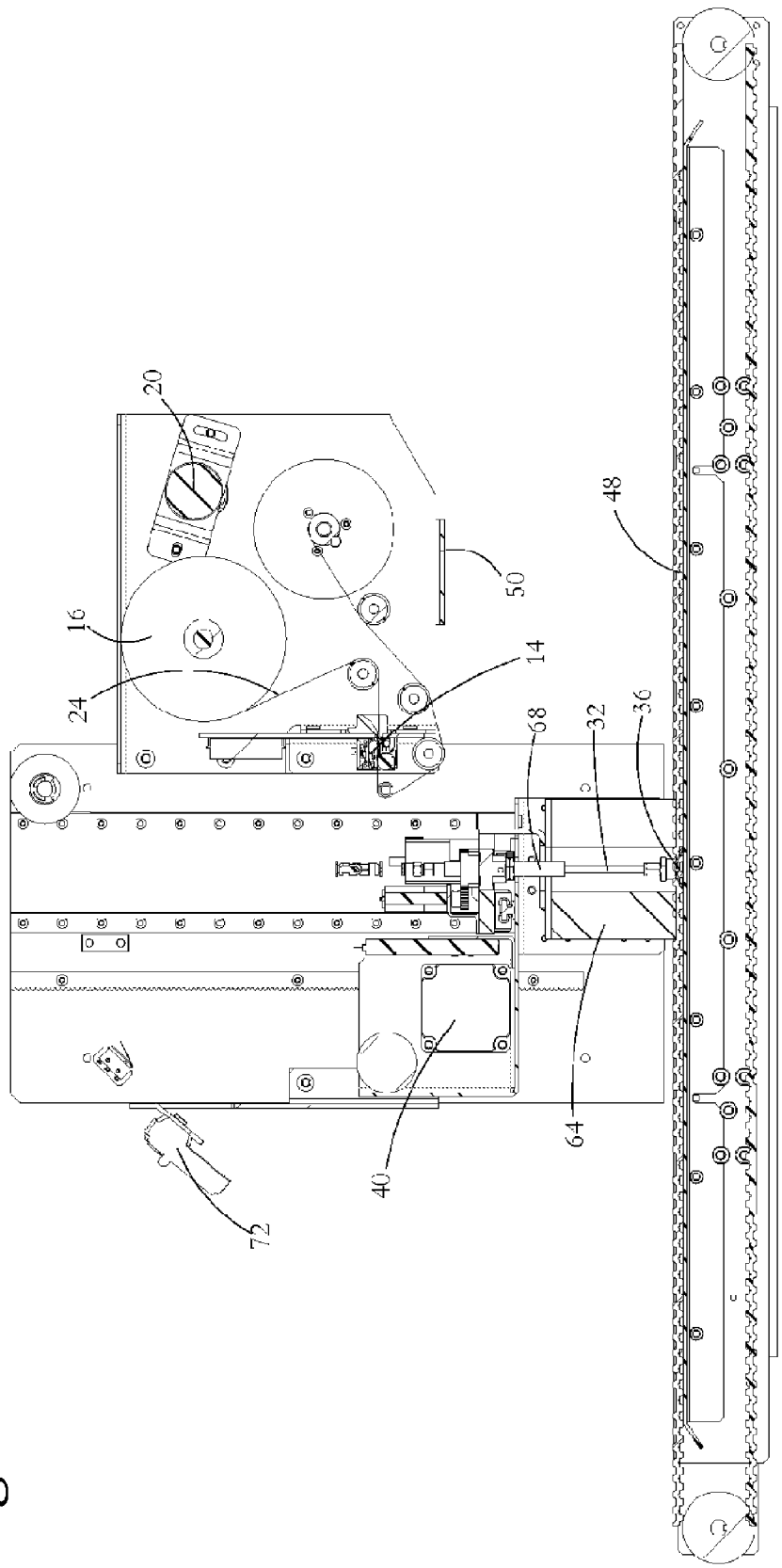
FIG. 74 is a side elevation corresponding to FIG. 68 and showing the position of elements of the labeling station in the course of a label tamping process.

With the suspended web fully withdrawn to the right as shown in FIGS. 73 and 74 and as monitored by a position switch 46 as shown in FIG. 68, a package 12 to which the suspended label is to be applied is exposed on a conveyor 48, the conveyor operating to move packages in the direction of arrow A synchronously with the operation of other elements of the labeling module.

The apparatus and method of implementations disclosed herein are adapted for labeling packages where a label 35 as applied to a package 12, must have a predetermined position and/or orientation. Proper placement of a label on a package is dependent on where the package 12 and the label 35 are at the instant of labeling. Consequently, the labeler includes a multi-element machine vision arrangement comprising several camera sub-systems and an image analysis module. The machine vision arrangement develops images of the package, the label and the packaged label at various stages of the labeling procedure and the analysis module is operable to derive and analyze the image data to enable proper completion of the labeling procedure. Some of the analysis may be performed automatically using OCR and position analysis software, while other analysis is performed by remote access by a human validation agent having access to the image data over a communications network.

The labeling module is adapted for use in medicament dispensing kiosks, as disclosed herein, in which medicament packages are stored in assigned slots of a storage rack. In such a kiosk, packages which are to be dispensed are picked from their storage slots by a pick head and brought to a function zone where they may be labeled or subjected to other functions such as discarding, reassignment to preferred slots, etc. The packages are moved between the storage rack and the function zone by a pick head mechanism of the sort as disclosed herein.

The machine vision arrangement includes a first camera sub-system associated with the pick head to ensure that a package delivered by the pick head to the conveyor 48 is the desired package based on a comparison of visible characteristics of the package with characteristics expected based on analysis of stored data for the package for which a pick instruction is issued. Each package must be examined in preparation for labeling. The package may have a number of parameters that can be recognized as a basis for determining the package identity. These include shape, size, and characterizing data previously applied to the package by the manufacture including, for example, the manufacturer's name and lot number. The characterizing data is usually sufficient to make an accurate identification of the package with relative certainty. If the package is not recognized, the labeling operation is either aborted with the unlabeled package being sent to a rejection zone, or a support request is automatically generated to a remote validation agent. The validation agent is able to view the package over a video link and to make a judgment as to the package identity provided the agent can see sufficient identifying data.

The analysis of the stored data for the package is also used to determine whether a label to be applied to the desired package must have a particular position and orientation and, if so, the particular details of the position and orientation.

The machine vision arrangement includes a second camera sub-system (not shown) for ensuring that the package delivered from the pick head to the conveyor 48 is in the correct position required for accurate labeling. If the package is not in the correct position, adjustment commands are generated from the analysis module for adjusting the conveyor forwardly or rearwardly and/or for adjusting the position of the label through altering the position of the suction cup as will be described presently. The machine vision arrangement includes a third camera sub-system including camera 72 for monitoring labels as they emerge from the printer 14 to ensure that they have been properly printed.

Following operation of the machine vision arrangement, if it is determined that a particular package must have a label applied at a certain position and orientation on the package, appropriate commands are generated for adjusting the relative positioning of the label and the package so that the label will be correctly applied to the package. The positioning criteria may be default criteria. The positioning criteria for the label to be applied may be based upon a determination that a portion of a surface of the particular package, has or does not have, visible indicia thereon as derived from image data received from one or more image capture devices (e.g., a camera). Alternatively, the positioning criteria may be criteria which are determined based on a precise label position placement requirement, for example, to meet specific regulation requirements. By way of example, a database accessible to the machine can be accessed to identify a specification for where a label is preferable to be applied to a package having a size and shape and containing a medicament to be dispensed from the machine. The identified specification can then be used to place the label on the corresponding portion of a surface of the particular package. In the latter case, the control logic determines whether the label 35 is in the right position to be driven downwardly against the package. If it is not, the relative positioning of the label and the package is adjusted within a plane perpendicular to the vertical drive direction. It will be appreciated that in alternative implementations, the direction in which the label is driven to apply it to the package may be other than vertically downward in which case other repositioning criteria must be met. The commands may factor in additional data necessary to ensure accurate placement of the label on the package including image data obtained by analyzing images from the first, second and third camera sub-systems.

In this implementation, independent adjustment of several position parameters of the label is permitted as the label is held by the suction cup 36. Firstly, as shown in FIG. 73, the tube 34 can be rotated by means of the gears 52, 56 (FIG. 7) about its vertical axis to change the angular orientation of the label in the label application plane. Secondly, the tube 34 can be driven along the rail 58 (FIG. 70) by the motor 60 to change the position of the suction gripped label along the first axis. And thirdly, the package conveyor 48 can be adjusted to move incrementally forward or backwards to change the relative positions of the label 35 and the package 12 along an axis orthogonal to the first axis. While the latter adjustments are translational adjustments along mutually perpendicular axes, it will be appreciated that any convenient combination of axes of rotation and translation can be used that provides the required degree of positional adjustment of the label relative to the package to which the label is to be applied. In one implementation, the permitted adjustments are two adjustments of the suction device and one adjustment of the package conveyor.

It will be appreciated that each type of adjustment can occur at either the label mounting arrangement or at the package supporting conveyor 48. Thus, for example, adjustment of the relative positions of the package and the label prior to labeling can be achieved by adjusting the position of the conveyor while the label is maintained in a fixed position by the suction grip.

Because the size, shape, position and orientation of the package are known from the imaging procedures, accurate label placement is possible with this method, with high reliability and repeatability. Once the label is in the desired position on the corresponding package, the suction grip is disabled, with a small burst of air pressure being developed in the tube 34 to encourage rapid release of the labeled package from the suction cup 36.

Cooperatively mounted with the vacuum assembly is the tamp assembly 62. The assembly includes a tamp block 64 with the tube 34 housed in a slot 66 in the tamp block to allow room for the positional adjustments of the tube and the suction cup as described previously. The tamp block 64 is of cubic form and is composed of a flexible closed-cell sponge or conformable polyurethane foam. After the relative positions of the label 35 and the package 12 to be labeled have been adjusted as required, the tamp assembly 62, including the tube 34 and the suction cup 36 from which a label is suspended, are driven downwards by the stepper motor 40 to drive the label against the package whereupon the adherent coating on the label causes the label to stick to the package. As the tamp block 64 is driven further downwardly against the package, the tamp block 64 applies pressure to the label to bend it to the shape of an upper part of the package.

The suction device mounting includes a buffer spring 68 which is normally uncompressed so as to maintain the mouth of the suction cup 36 projecting just below a bottom face of the tamp block 64. When the tamp block 64 is pressed down against the package, the buffer spring 68 undergoes compression allowing the suction cup 36 to move upwards into the tamp block 64 to allow the block 64 to wrap around the package. The tamp block 64 can be contoured at its lower face to permit accommodation of the suction cup as the buffer spring 68 is compressed so as to prevent the suction cup from adversely affecting the tamping effectiveness.

The packages may be any of a range of shapes and sizes and the tamp block 64 operates to wrap the label 35 over a contoured surface and around package corners. Whereas the nature of the deformation of the tamp block 64 to apply pressure against the sides of the package occurs by the tamp block 64 being squeezed between a mounting fixture at its top side and the medicament package at its bottom side, other external fixtures can be used to guide the deformation of the tamp block 64 to the shape and application of pressure required to effectively apply the label where required on the package. Depending on the particular dynamics desired in the tamping process, the tamp block can be of a more complex shape such as the inverted U-form described in co-pending U.S. patent application Ser. No. 12/551,470, filed on Aug. 31, 2009, titled "Method and Apparatus For Labelling," which is herein specifically incorporated by reference. Such a shape may be advantageous for bending a label around the corners of a medicament package. Dimensions and materials for the tamp assembly are selected so as to direct pressure to contact the label to all intended parts of the package and to apply sufficient pressure to activate the contact sensitive adhesive.

When the tamp procedure is completed, the tamp assembly 62 is vertically stepped upwardly back to its start position and the tensioner 22 is operated to draw a length of label web 24 from the supply reel 16 to start a new labeling operation. The conveyor 48 is advanced a predetermined distance to convey the labeled package to a position under a fourth camera sub-system 50 for monitoring whether the label has been correctly applied to the package. If the labeling has been properly effected, conveyor advance continues to send the labeled package for dispensing or other desired function. If the labeling is not satisfactory, the package is conveyed to a reject zone. The advancing conveyor also transports the next successive unlabeled package into the labeling station. It will be seen that as packages are successively labeled, the take-off reel 18 oscillates between a fixed mode where operation of the printer advance mechanism draws new web from the supply reel 16 and a driven mode to wind the backing from which labels 35 have been removed.

In another implementation, the conveyor 48 is brought towards the suction cup 36 to effect application of the label to the package 12 instead of or in addition to moving the suction cup and the tamp block 64 towards the conveyor. Also, in a further alternative, both the label and the package 12 are moved to effect the label application.

The machine vision arrangement may also include an optical sensor sub-system associated with the suction device to measure the height of a package as the conveyor comes to a halt immediately before application of the label. The optical sensor sub-system is valuable for determining a required travel of the tamp assembly, which should be greater for low packages than for high packages The function of the optical sensor sub-system is alternatively achieved by a detector mounted on the suction device to detect the instant that the suction cup with gripped label touches the package. The detector output forms an input to processing logic for computing the position of the suction cup, and therefore the top surface of the package at that instant.

It will be appreciated that accurate placement of a label on a medicament package 12 is a function of the position and orientation of the label and the position and orientation of the package when the label and the package are brought together. In the preceding description, emphasis is on adjusting the position and orientation of the suction cup 36 and the label gripped by it to match the position and orientation of the package 12. It is conceivable that as the label is separated from its backing or as the label is maneuvered prior to its application to the package, the label position and orientation may itself be inadvertently altered. In a modification, the machine vision system uses a further element (not shown) to monitor the position of the label as it is gripped by the suction cup. If it is determined by automatically analyzing the position data that the gripped label is not ideally positioned and that this would result in a skewed application to the package, notwithstanding perfect placement of the package, an output from this element of the machine vision system is used to make a further alteration of the label position and/or orientation, as necessary.

Variation and modifications will be apparent to those skilled in the art, and the embodiments of the invention described and illustrated are not intended to be limiting. The principles of the invention contemplate many alternatives having advantages and properties evident in the exemplary implementations.

The steps of a method, process, or algorithm described in connection with the implementations disclosed herein may be embodied directly in hardware, in a software module executed by a processor, or in a combination of the two. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes.

The above description of the disclosed implementations is provided to enable any person of ordinary skill in the art to make or use the disclosure. Various modifications to these implementations will be readily apparent to those of ordinary skill in the art, and the generic principles defined herein may be applied to other implementations without departing from the spirit or scope of the disclosure. Thus, the disclosure is not intended to be limited to the implementations shown herein but is to be accorded the widest scope consistent with the principles and novel features disclosed herein.

What is claimed is:

1. In a vending machine having storage for a plurality of containers, at least one image capture device, a picking device to move the containers within the vending machine, a label module to a position and apply a label to one said container containing a product, a user interface, and a delivery zone accessible to a user, a method comprising:
    receiving, at the user interface, a request from a user for the one said container containing the product;
    picking and moving, with the picking device, the one said container situated among the plurality of containers in an access location in the storage to a labeling zone in the label module, wherein the picking device includes a telescopic unit to drive the pick head into and out of then access location corresponding to the one said container situated among the plurality of containers to move the one said container to the labeling zone in the label module;
    receiving and analyzing image data from the at least one image capture device to derive therefrom a first position of the one said container in the labeling zone;
    sending data from the at least one image capture device to a remote station, wherein:
        the sent data comprises at least one image of the labeled one said container; and
        the delivery of the labeled one said container to the delivery zone is a subjective dispensing decision made by a human agent at the remote station who initiates the sending of the dispensing instruction for the requested product from the remote station based, at least in part, upon the at least one image of the labeled one said container;
    adjusting the first position of the one said container in the labeling zone, as a function of the received and analyzed image data, to a second position thereof;
    determining a portion of the surface of the one said container in the labeling zone over which the label is to be applied based upon one of:
        visible indicia within the portion as derived from the received and analyzed image data from the at least one image capture device;
        absence of visible indicia within the portion as derived from the received and analyzed image data from the at least one image capture device; and
        a corresponding database of respective specifications for where the label is to be applied to each of a plurality of unlabeled said containers of different sizes and shapes, and containing different products;
    applying the label to the one said container in second position thereof in the labeling zone;
    sending data from the at least one image capture device to the remote station that includes at least one image of the labeled one said container;
    receiving a dispensing instruction from the remote station; and
    delivering the labeled one said container to the delivery zone.

2. The method as defined in claim 1, further comprising receiving payment from the user for the requested product.

3. The method as defined in claim 1, further comprising printing on the label information corresponding to the product requested by the user at the vending machine.

4. In a vending machine having storage for a plurality of containers, at least one image capture device, a picking device to move the containers within the vending machine, a label module to a position and apply a label to one said container containing a product, a user interface, and a delivery zone accessible to a user, a method comprising:
receiving, at the user interface, a request from a user for the one said container containing the product;
sending, to a remote station, the request from the user at the vending machine for the one said container containing the product, wherein the request for the product is a prescription for a medicament;
receiving a dispensing instruction for the requested product from the remote station, wherein the dispensing instruction is for the prescription for the medicament;
picking and moving, with the picking device, the one said container situated among the plurality of containers from the storage to a labeling zone in the label module, wherein the picking device includes:
a pick head including a platform; and
a telescopic unit to drive the pick head to an access location corresponding to the one said container situated among the plurality of containers, wherein:
the telescopic unit has a spool of drive tape;
the drive tape has:
a free end fixed to the platform;
ready bendability in a first direction to permit storing at the spool upon platform exit; and
relative unbendability in an opposed direction, whereby:
the drive tape provides axial thrust and platform entry upon unwinding of the spool; and
the drive tape drives the platform by telescoping into and out of the access location;
the platform is moved progressively under the one said container at the access location; and
the telescopic unit drives the platform by telescoping out of the access location while the platform engages the one said container to move the one said container out of the access location;
receiving and analyzing image data from the at least one image capture device to derive therefrom a first position of the one said container in the labeling zone;
adjusting the first position of the one said container in the labeling zone, as a function of the received and analyzed image data, to a second position thereof;
applying the label to the one said container in second position thereof in the labeling zone;
sending data from the at least one image capture device to the remote station that includes at least one image of the labeled one said container; and
delivering the labeled one said container to the delivery zone which is accessible to the user.

5. The method as defined in claim 4, wherein receiving the dispensing instruction is initiated by a human agent at the remote station, whereby the delivery of the labeled one said container to the delivery zone is a subjective dispensing decision to dispense the prescription for the medicament from the vending machine to the user.

6. The method as defined in claim 4, further comprising sending data from the at least one image capture device to the remote station, wherein the sent data comprises at least one image of the labeled one said container, whereby the delivery of the labeled one said container to the delivery zone can be a subjective dispensing decision made by a human agent at the remote station who initiates the sending of the dispensing instruction for the requested product from the remote station based, at least in part, upon the at least one image of the labeled one said container.

7. The method as defined in claim 4, further comprising receiving payment from the user for the requested product.

8. The method as defined in claim 4, further comprising printing on the label information corresponding to the product requested by the user at the vending machine.

9. In a vending machine having storage for a plurality of containers, at least one image capture device, a picking device to move the containers within the vending machine, a label module to a position and apply a label to one said container containing a product, a user interface, and a delivery zone accessible to a user, a method comprising:
receiving, at the user interface, a request from a user for the one said container containing the product;
receiving payment from the user for the product requested by the user at the vending machine;
printing on the label information corresponding to the product requested by the user at the vending machine;
picking and moving, with the picking device, the one said container situated among the plurality of containers in an access location in the storage to a labeling zone in the label module, wherein the picking device includes a telescopic unit to drive the pick head into and out of then access location corresponding to the one said container situated among the plurality of containers to move the one said container to the labeling zone in the label module;
receiving and analyzing image data from the at least one image capture device to derive therefrom a first position of the one said container in the labeling zone;
sending data from the at least one image capture device to a remote station, wherein:
the sent data comprises at least one image of the labeled one said container; and
the delivery of the labeled one said container to the delivery zone is a subjective dispensing decision made by a human agent at the remote station who initiates the sending of the dispensing instruction for the requested product from the remote station based, at least in part, upon the at least one image of the labeled one said container;
adjusting the first position of the one said container in the labeling zone, as a function of the received and analyzed image data, to a second position thereof;
determining a portion of the surface of the one said container in the labeling zone over which the label is to be applied based upon one of:
visible indicia within the portion as derived from the received and analyzed image data from the at least one image capture device;
absence of visible indicia within the portion as derived from the received and analyzed image data from the at least one image capture device; and
a corresponding database of respective specifications for where the label is to be applied to each of a plurality of unlabeled said containers of different sizes and shapes, and containing different products;
applying the label to the one said container in second position thereof in the labeling zone;
sending data from the at least one image capture device to the remote station that includes at least one image of the labeled one said container;
receiving a dispensing instruction from the remote station; and
delivering the labeled one said container to the delivery zone.

10. The method as defined in claim 9, wherein the applying the label to the one said container in second position thereof in the labeling zone further comprises:
forcing the label to make a conforming contact between a deformable tamp block and the one said container such that the deformable tamp block is changed from a non-deformed shape to a deformed shape thereof; and
separating the one said container and the deformable tamp block such that the deformable tamp block is changed back to the non-deformed shape thereof.

11. The method as defined in claim 9, wherein the plurality of containers:
are each selected from the group consisting of a bottle, a box and a foil package; and
have different sizes and shapes and contain different products.

12. The method as defined in claim 9, further comprising, in response to sending to the remote station, receiving a dispensing instruction for the requested product from the remote station, wherein the dispensing instruction is for a prescription for a medicament.

13. The method as defined in claim 12, wherein receiving the dispensing instruction is initiated by a human agent at the remote station, whereby the delivery of the labeled one said container to the delivery zone is a subjective dispensing decision to dispense the prescription for the medicament from the vending machine to the user.

14. The method as defined in claim 9, wherein the picking device includes:
a pick head including a platform; and
a telescopic unit to drive the pick head to an access location corresponding to the one said container situated among the plurality of containers.

15. The method as defined in claim 14, wherein:
the telescopic unit has a spool of drive tape; and
the drive tape has:
a free end fixed to the platform;
ready bendability in a first direction to permit storing at the spool upon platform exit; and
relative unbendability in an opposed direction, whereby:
the drive tape provides axial thrust and platform entry upon unwinding of the spool; and
the drive tape drives the platform by telescoping into and out of the access location;
the platform is moved progressively under the one said container at the access location; and
the telescopic unit drives the platform by telescoping out of the access location while the platform engages the one said container to move the one said container out of the access location.

* * * * *